(12) United States Patent
Hedhammar

(10) Patent No.: US 10,662,230 B2
(45) Date of Patent: *May 26, 2020

(54) CYCLIC RGD CELL-BINDING MOTIF AND USES THEREOF

(71) Applicant: Spiber Technologies AB, Stockholm (SE)

(72) Inventor: My Hedhammar, Stockholm (SE)

(73) Assignee: SPIBER TECHNOLOGIES AB, Stockholm (SE)

(*) Notice: Subject to any disclaimer, the term of this patent is extended or adjusted under 35 U.S.C. 154(b) by 0 days.

This patent is subject to a terminal disclaimer.

(21) Appl. No.: 16/403,780

(22) Filed: May 6, 2019

(65) Prior Publication Data

US 2019/0322710 A1  Oct. 24, 2019

Related U.S. Application Data

(63) Continuation of application No. 15/739,057, filed as application No. PCT/EP2016/064543 on Jun. 23, 2016, now Pat. No. 10,316,069.

(30) Foreign Application Priority Data

Jun. 26, 2015 (EP) ..................................... 15174072

(51) Int. Cl.
| | |
|---|---|
| A61K 38/00 | (2006.01) |
| C07K 14/435 | (2006.01) |
| C08H 1/00 | (2006.01) |
| C12N 5/00 | (2006.01) |
| C12N 15/62 | (2006.01) |
| C07K 16/28 | (2006.01) |

(52) U.S. Cl.
CPC ......... C07K 14/43518 (2013.01); C08H 1/00 (2013.01); C12N 5/0068 (2013.01); C12N 15/62 (2013.01); *C07K 16/2839* (2013.01); *C07K 2319/70* (2013.01); *C12N 2533/50* (2013.01)

(58) Field of Classification Search
None
See application file for complete search history.

(56) References Cited

FOREIGN PATENT DOCUMENTS

| WO | WO 2007/078239 A2 | 7/2007 |
| WO | WO 2013/185027 A2 | 12/2013 |
| WO | WO-2013185027 A2 * | 12/2013 |
| WO | WO 2014/027042 A2 | 2/2014 |
| WO | WO 2015/036619 A1 | 3/2015 |

OTHER PUBLICATIONS

Bini et al., "RGD-Functionalized Bioengineered Spider Dragline Silk Biomaterial", Biomacromolecules, vol. 7, No. 11, 2006, pp. 3139-3145.
European Search Report for EP 15 17 4072, dated Oct. 15, 2015.
International Search Report issued in PCT/EP2016/064543 (PCT/ISA/210), dated Oct. 21, 2016.
Ivanov et al., "Synthesis and Use of a New Bromoacetyl-Derivatized Heterotrifunctional Amino Acid for Conjugation of Cyclic RGD-Containing Peptides Derived from Human Bone Sialoprotein", Bioconjugate Chemistry, vol. 6, No. 3, 1995, pp. 269-277.
Koivunen et al., "Phage Libraries Displaying Cyclic Peptides with Different Ring Sizes: Ligand Specificities of the RGD-Directed Integrins", BioTechnology, vol. 13, Mar. 1995, pp. 265-270.
Shalaly et al., "Silk matrices promote formation of insulin-secreting islet-like clusters", Biomaterials, vol. 90, 2016, pp. 50-61.
Widhe et al., "A fibronectin mimetic motif improves integrin mediated cell biding to recombinant spider silk matrices", Biomaterials, vol. 74, 2016, pp. 256-266.
Written Opinion of the International Searching Authority issued in PCT/EP2016/064543 (PCT/ISA/237), dated Oct. 21, 2016.

* cited by examiner

*Primary Examiner* — Jeanette M Lieb
(74) *Attorney, Agent, or Firm* — Birch, Stewart, Kolasch & Birch, LLP

(57) ABSTRACT

A recombinant fusion protein is comprising a spider silk fragment and a cyclic RGD cell-binding motif with selectivity for integrins, such as for α5β1 integrins. The fusion protein is useful as a cell scaffold material and for the cultivation of cells displaying integrins on their cell surface.

19 Claims, 11 Drawing Sheets

Specification includes a Sequence Listing.

| | |
|---|---|
| CThyb_Esp | SRLSSPEASS RVSSAVSNLV SSG-PTNSAA LSSTISNVVS QIGASNPGLS |
| CTnat_Eau | SRLSSPSAVS RVSSAVSSLV SNG-QVNMAA LPNIISNISS SVSASAPGAS |
| AF350266_At1 | SRLSSPGAAS RVSSAVTSLV SSGGPTNSAA LSNTISNVVS QISSSNPGLS |
| AY666062_Cm1 | SHLSSPEASS RVSSAVSNLV SSG-STNSAA LPNTISNVVS QISSSNPGLS |
| AF350273_Lg1 | SALAAPATSA RISSHASTLL SNG-PTNPAS ISNVISNAVS QISSSNPGAS |
| AY953074_Lh1 | SALSAPATSA RISSHASALL SSG-PTNPAS ISNVISNAVS QISSSNPGAS |
| AY666068_Mh1 | SHLSSPEASS RVSSAVSNLV SGG-STNSAA LPNTISNVVS QISSSNPGLS |
| U20329_Nc1 | SRLSSPQASS RVSSAVSNLV ASG-PTNSAA LSSTISNVVS QIGASNPGLS |
| AY666076_Np1 | SRLSSPEASS RVSSAVSNLV SSG-PTNSAA LSNTISNVVS QISSSNPGLS |
| AF350277_Nm1 | SRLSSPQASS RVSSAVSNLV ASG-PTNSAA LSSTISNAVS QIGASNPGLS |
| AF350279_Ns1 | SRLSSPEASS RVSSAVSNLV SSG-PTNSAA LSSTISNVVS QIGASNPGLS |
| AY666057_Ov1 | SRLSSPEASS RVSSAVSNLV SSG-PTNSAA LSNTISNVVS QISSSNPGLS |
| AY666064_Ps1 | SRLSSPEASS RVSSAVSNLV SSG-PTNSAA LPNTISNVVS QISSSNPGLS |
| AF350285_Tk1 | SLLSSPASNA RISSAVSALA SGA-ASGPGY LSSVISNVVS QVSSNSGGLV |
| AF350286_Tv1 | SRLSSPASNA RISSAVSALA SGG-ASSPGY LSSIISNVVS QVSSNDGLS |
| ABU20328_Ab2 | SRLSSSAASS RVSSAVSSLV SSG-PTTPAA LSNTISSAVS QISASNPGLS |
| AY365016_Aam2 | -RLSSPQASS RVSSAVSTLV SSG-PTNPAS LSNAIGSVVS QVSASNPGLP |
| AF350263_Aau2 | SRLSSPQASS RVSSAVSTLV SSG-PTNPAA LSNAISSVVS QVSASNPGLS |
| AF350267_At2 | SRLSSPQASS RVSSAVSTLV SSG-PTNPAS LSNAISSVVS QVSSSNPGLS |
| AF350272_Gm2 | SRLSSPQAGA RVSSAVSALV ASG-PTSPAA VSSAISNVAS QISASNPGLS |
| AF350275_Lg2 | SALSSPTTHA RISSHASTLL SSG-PTNSAA ISNVISNAVS QVSASNPGSS |
| AY953075_Lh2 | SALSSPTTHA RISSHASTLL SSG-PTNAAA LSNVISNAVS QVSASNPGSS |
| AY654293_Nc2 | SRLASPDSGA RVASAVSNLV SSG-PTSSAA LSSVISNAVS QIGASNPGLS |
| AF350278_Nm2 | SRLASPDSGA RVASAVSNLV SSG-PTSSAA LSSVISNAVS QIGASNPGLS |
| AF350280_Ns2 | SRLASPDSGA RVASAVSNLV SSG-PTSSAA LSSVIXNAVS QIGASNPGLS |
| AF350269_DtFb1 | SRLSSPEAAS RVSSAVSSLV SNG-QVNVDA LPSIISNLSS SISASATTAS |
| AF350270_DtFb2 | SRLSSPQAAS RVSSAVSSLV SNG-QVNVAA LPSIISSLSS SISASSTAAS |
| U47853_ADF1 | NRLSSAGAAS RVSSNVAAIA SAG----AAA LPNVISNIYS GVLSS--GVS |
| U47854_ADF2 | SRLSSPSAAA RVSSAVS-LV SNGGPTSPAA LSSSISNVVS QISASNPGLS |
| U47855_ADF3 | SRLSSPAASS RVSSAVSSLV SSG-PTKHAA LSNTISSVVS QVSASNPGLS |
| U47856_ADF4 | SVYLRLQPRL EVSSAVSSLV SSG-PTNGAA VSGALNSLVS QISASNPGLS |
| | |
| Consensus | SRLSSPQASS RVSSAVSNLV SSG-PTNSAA LSNTISNVVS QISASNPGLS |

Fig 9

```
CThyb_Esp      GCDVLVQALL EVVSALIHIL GSSSIGQVNY GSAGQATQLV GQSVYQALGE F
CTnat_Eau      GCEVIVQALL EVITALVQIV SSSSVGYINP SAVNQITNVV ANAMAQVMG- -
AF350266_At1   GCDVLVQALL EIVSALVHIL GSANIGQVNS SGVGRSASIV GQSINQAFS- -
AY666062_Cm1   GCDVLVQALL EVVSALIHIL GSSSIGQVNY GSAGQATQIV ---------- -
AF350273_Lg1   SCDVLVQALL ELVTALLTII GSSNVGNVNY DSSGQYAQVV SQSVQNAFV- -
AY953074_Lh1   ACDVLVQALL ELVTALLTII GSSNIGSVNY DSSGQYAQVV TQSVQNVFG- -
AY666068_Mh1   GCDVLVQALL EVVSALIHIL GSSSIGQVDY GSAGQATQIV GQSA------ -
U20329_Nc1     GCDVLIQALL EVVSALIQIL GSSSIGQVNY GSAGQATQIV GQSVYQALG- -
AY666076_Np1   GCDVLVQALL EVVSALIHIL GSSSIGQVNY GSAGQATQIV ---------- -
AF350277_Nm1   GCDVLIQALL EVVSALIHIL GSSSIGQVNY GSAGQATQ-- ---------- -
AF350279_Ns1   GCDVLIQALL EVVSALVHIL GSSSIGQVNY GSAGQATQ-- ---------- -
AY666057_Ov1   GCDVLVQALL EVVSAPIHIL GSSSIGQVNY GSAGQATQIV ---------- -
AY666064_Ps1   GCDVLVQALL EVVSALIHIL GSSSIGQVNY GSAGQATQIV ---------- -
AF350285_Tk1   GCDTLVQALL EAAAALVHVL ASSSGGQVNL NTAGYTSQL- ---------- -
AF350286_Tv1   GCDTVVQALL EVAAALVHVL ASSNIGQVNL NTAGYTSQL- ---------- -
ABU20328_Ab2   GCDVLVQALL EVVSALVHIL GSSSVGQINY GASAQYAQMV ---------- -
AY365016_Aam2  SCDVLVQALL EIVSALVHIL GSSSIGQINY SASSQYARLV GQSIAQALG- -
AF350263_Aau2  GCDVLVQALL ELVSALVHIL GSSSIGQINY AAS------- ---------- -
AF350267_At2   GCDVLVQALL EIVSALVHIL GSSSIGQINY AASSQYAQLV GQSLTQALG- -
AF350272_Gm2   GCDVLVQALL EIVSALVSIL SSASIGQINY GASGQYAAMI ---------- -
AF350275_Lg2   SCDVLVQALL ELITALISIV DSSNIGQVNY GSSGQYAQMV G--------- -
AY953075_Lh2   SCDVLVQALL EIITALISIL DSSSVGQVNY GSSGQYAQIV GQSMQQAMG- -
AY654293_Nc2   GCDVLIQALL EIVSACVTIL SSSSIGQVNY GAASQFAQVV GQSVLSAF-- -
AF350278_Nm2   GCDVLIQALL EIVSACVTIL SSSSIGQVNY GAA------- ---------- -
AF350280_Ns2   GCDVLIXALL EIVSACVTIL SSSSIGQVNY GAA------- ---------- -
AF350269_DtFb1 DCEVLVQVLL EVVSALVQIV CS-------- ---------- ---------- -
AF350270_DtFb2 DCEVLVQVLL EIVSALVQIV SSANVGYINP EASGSLN-AV GSALAAAMG- -
U47853_ADF1    SSEALIQALL EVISALIHVL GSASIGNVSS VGVNSALNAV QNAVGAYAG- -
U47854_ADF2    GCDILVQALL EIISALVHIL GSANIGPVNS SSAGQSASIV GQSVYRALS- -
U47855_ADF3    GCDVLVQALL EVVSALVSIL GSSSIGQINY GASAQYTQMV GQSVAQALA- -
U47856_ADF4    GCDALVQALL ELVSALVAIL SSASIGQVNV SSVSQSTQMI SQALS----- -

Consensus      GCDVLVQALL EVVSALVHIL GSSSIGQVNY GSAGQATQIV GQSVAQALGE F
```

Fig 9 (continued)

CYCLIC RGD CELL-BINDING MOTIF AND USES THEREOF

CROSS REFERENCE TO RELATED APPLICATIONS

This application is a Continuation of co-pending application Ser. No. 15/739,057 filed on Dec. 21, 2017, which is the National Phase under 35 U.S.C. § 371 of International Application No. PCT/EP2016/064543, filed on Jun. 23, 2016, which claims the benefit under 35 U.S.C. § 119(a) to patent application Ser. No. 15/174,072.7, filed in Europe on Jun. 26, 2015, all of which are hereby expressly incorporated by reference into the present application.

TECHNICAL FIELD OF THE INVENTION

The present invention relates to the fields of eukaryotic cell culture and tissue engineering. The invention provides new proteins, a cell scaffold material comprising the proteins, and a method for cultivation of cells wherein polymers of the new proteins are used as a cell scaffold material.

BACKGROUND TO THE INVENTION

The phenotype of a cell is largely influenced by its display of integrins. By expressing several types of integrins on its surface, the cell is able to bind multiple kinds of ligands and thereby interpret parallel signals from the surrounding extracellular matrix (ECM). Cells cultured in vitro often express a different kind of integrin pattern than corresponding cells in vivo. In order to maintain the original phenotype of cells, or to accomplish a specific cellular response (e.g. differentiation, proliferation), it is important to enable integrin binding also during in vitro culture. This is most commonly done by coating cell culture plastics with ECM proteins like laminin, fibronectin, collagen or vitronectin, or mimics thereof. The ECM coatings will provide ligands for various integrins, with activation of different cellular pathways as a result. However, within several cell culture disciplines it is desirable to find ways to accomplish this on a defined matrix without the use of animal derived substrates.

WO 2011/129756 discloses methods and a cell scaffold material based on a miniature spider silk protein for eukaryotic cell culture. The protein may contain various short (3-5 amino acid residues) cell-binding peptides.

WO 2012/055854 discloses polymers consisting of a fusion protein containing a miniature spider silk protein and a large non-spidroin protein fragment of more than 30 amino acid residues which provides affinity to another molecule. The fusion protein may additionally contain various cell-binding peptides.

WO 2015/036619 discloses polymers consisting of a fusion protein containing a miniature spider silk protein and a cell-binding peptide comprising the amino acid residues RGD. The fusion protein is useful for cultivation of human pluripotent stem cells (hPSCs).

Several strategies have been attempted in order to accomplish ligands with high affinity and selectivity for specific integrins. For instance, phage libraries expressing RGD-containing peptides have been used in panning experiments. The outcome of such experiments is however dependent on limitations of the sequence coverage in the phage library. Moreover, epitopes that promote cell adherence might be missed when using a selection method that is based on inhibition of binding to coated integrins by peptides in solution. The interaction between a cell and the surrounding ECM is a cross-talk where initial binding causes intracellular signaling resulting in integrin activation and conformational changes that affects the affinity to the ligand. Thus, a cell-free system with coated integrins might miss the peptides with highest affinity to the activated form of the integrin. Ivanov, B. et al., Bioconjugate Chem. 6: 269-277 (1995) and Koivunen E. et al., Biotechnology 13(3): 265-270 (1995) disclose various RGD-containing peptides.

Several peptidomimetics and non-peptidic small molecules have been designed and synthesized with the purpose to find potent and selective integrin ligands. Rational design of ligands for certain integrins has been hampered by the lack of determined structures.

In most previous studies the goal has been to obtain a potent inhibitor of a specific integrin binding, for example with the purpose to hinder tumor cell invasion or unwanted angiogenesis. In those cases, a functional integrin binding is not required; rather the goal is a soluble molecule that is a potent integrin antagonist. WO 2013/185027 discloses soluble variants of human fibronectin with integrin antagonist activity, i.e. blocking or reducing activities of integrin, such as cell adhesion.

Despite these advances in the field, there is still a need for new cell scaffolds in the field, in particular since various cell types may have preference for different scaffolds and since there is a need for efficient cell scaffolds for wound healing.

SUMMARY OF THE INVENTION

It is an object of the present invention to provide proteins and a cell scaffold that promotes proliferation, differentiation and migration of cells, in particular primary cells.

It is in particular an object of the present invention to provide proteins and a cell scaffold which support proliferation, differentiation and migration of keratinocytes.

It is a further object of the present invention to achieve increased cell adhesion efficacy to a cell scaffold.

It is in particular an object of the present invention to provide proteins and a cell scaffold which provides early attachment of adherent cells.

It is also an object of the present invention to provide proteins and a cell scaffold that are useful for efficient expansion of adherent cells in vitro.

It is also an object of the present invention to provide proteins and a cell scaffold that are useful for transferring cells as a cell sheet, e.g. to a wound area in vivo.

Is it an object of the present invention to provide proteins and a cell scaffold that attract inherent cells for migration into a wound area, e.g. from the wound edges from where dermal keratinocytes are usually recruited during wound healing.

For these and other objects that will be evident from the following disclosure, the present invention provides a cyclic RGD cell-binding motif comprising the amino acid sequence $$C^1X^1X^2RGDX^3X^4X^5C^2$$

wherein
each of $X^1$, $X^2$, $X^3$, $X^4$ and $X^5$ are independently selected from natural amino acid residues other than cysteine; and $C^1$ and $C^2$ are connected via a disulphide bond. The cell-binding motif has selectivity for integrins, such as for α5β1 integrins.

It has surprisingly been found that recombinant proteins containing this cyclic RGD cell-binding motif are useful for the cultivation of cells displaying integrins on their cell surface.

Without limitation thereto, preferred cells are selected from skeletal muscle cells, endothelial cells, stem cells, fibroblasts, keratinocytes and cell lines.

Without wishing to be bound to any specific theory, it is contemplated that the cell-binding motif presented herein imitates the α5β1-specific RGD loop motif of fibronectin by positioning cysteines adjacent to the RGD sequence to allow formation of a disulphide-bridge to constrain the chain into a similar type of turn loop. This cyclic RGD cell-binding motif increases the cell adhesion efficacy to a matrix made of a protein containing the cell-binding motif, such as a recombinantly produced spider silk protein.

The present invention provides according to an aspect a recombinant protein comprising said cell-binding motif with selectivity for integrins, such as for α5β1 integrins. This recombinant protein is surprisingly useful for the cultivation of cells displaying integrins on their cell surface.

The present invention provides according to a one aspect a recombinant fusion protein comprising a spidroin fragment and said cell-binding motif with selectivity for integrins, such as for α5β1 integrins. This recombinant fusion protein is surprisingly useful for the cultivation of cells displaying integrins on their cell surface.

In preferred embodiments of the invention, each of $X^1$, $X^2$, $X^3$, $X^4$ and $X^5$ are independently selected from the group of amino acid residues consisting of: G, A, V, S, T, D, E, M, P, N and Q.

In other preferred embodiments of the invention, each of $X^1$ and $X^3$ are independently selected from the group of amino acid residues consisting of: G, S, T, M, N and Q; and each of $X^2$, $X^4$ and $X^5$ are independently selected from the group of amino acid residues consisting of: G, A, V, S, T, P, N and Q.

In certain preferred embodiments of the invention, $X^1$ is selected from the group of amino acid residues consisting of: G, S, T, N and Q; $X^3$ is selected from the group of amino acid residues consisting of: S, T and Q; and each of $X^2$, $X^4$ and $X^5$ are independently selected from the group of amino acid residues consisting of: G, A, V, S, T, P and N.

In some embodiments of the invention, $X^1$ is S or T; $X^2$ is G, A or V; preferably G or A; more preferably G; $X^3$ is S or T; preferably S; $X^4$ is G, A, V or P; preferably G or P; more preferably P; and $X^5$ is G, A or V; preferably G or A; more preferably A.

In certain preferred embodiments of the invention, the cell-binding motif is comprising the amino acid sequence CTGRGDSPAC (SEQ ID NO: 10).

Further preferred cyclic RGD cell-binding motifs according to the invention display at least 60%, such as at least 70%, such as at least 80%, such as at least 90% identity to CTGRGDSPAC (SEQ ID NO: 10), with the proviso that position 1 and 10 are always C; position 4 is always R; position 5 is always G; position 6 is always D; and positions 2-3 and 7-9 are never cysteine. It is understood that the non-identical positions among positions 2-3 and 7-9 can be freely selected as set out above.

In some preferred fusion proteins according to the invention, the cell-binding motif is arranged N-terminally of the spidroin fragment.

In certain preferred fusion proteins according to the invention, the spidroin fragment is comprising the protein moieties REP and CT, wherein REP is a repetitive fragment of from 70 to 300 amino acid residues, selected from the group consisting of $L(AG)_nL$, $L(AG)_nAL$, $L(GA)_nL$, and $L(GA)_nGL$, wherein n is an integer from 2 to 10;

each individual A segment is an amino acid sequence of from 8 to 18 amino acid residues, wherein from 0 to 3 of the amino acid residues are not Ala, and the remaining amino acid residues are Ala;

each individual G segment is an amino acid sequence of from 12 to 30 amino acid residues, wherein at least 40% of the amino acid residues are Gly; and each individual L segment is a linker amino acid sequence of from 0 to 30 amino acid residues; and CT is a fragment of from 70 to 120 amino acid residues, having at least 70% identity to SEQ ID NO: 3.

In some preferred fusion proteins according to the invention, the spidroin fragment has at least 70% identity to SQ ID NO: 2 or to amino acid residues 18-277 of SEQ ID NO: 13.

According to a further aspect, the present invention provides a cell scaffold material comprising a protein polymer which as a repeating unit is containing the recombinant fusion protein according to the invention.

In a preferred embodiment of the cell scaffold material according to the invention, the protein polymer is in a physical form selected from the group consisting of film, coating, foam, fiber and fiber-mesh.

In one preferred embodiment of the cell scaffold material according to the invention, the protein polymer is in a physical form of a free-standing matrix.

According to a related aspect, the present invention provides a method for the cultivation of cells, comprising the steps of providing a sample of cells;

applying the sample to a cell scaffold material; and maintaining the cell scaffold material having the cells applied thereto under conditions suitable for cell culture;

wherein the cell scaffold material comprises a protein polymer, which is containing the recombinant protein, such as the recombinant fusion protein, according to the invention as a repeating structural unit.

It has surprisingly been found that recombinant proteins containing this cyclic RGD cell-binding motif are useful for the cultivation of cells displaying integrins on their cell surface. Without limitation thereto, preferred cells are selected from skeletal muscle cells, endothelial cells, stem cells, fibroblasts, keratinocytes and cell lines.

According to a further aspect, the present invention provides use of the recombinant fusion protein according to the invention, the cell scaffold material according to the invention, or the recombinant protein according to the invention for the cultivation of cells displaying integrins on their cell surface.

It has surprisingly been found that recombinant proteins, such as recombinant fusion proteins, containing this cyclic RGD cell-binding motif are useful for the cultivation of cells displaying integrins on their cell surface. The immobilized (i.e. not in solution) cell-binding motif promotes integrin activation and cell binding.

Without limitation thereto, preferred cells are selected from skeletal muscle cells, endothelial cells, stem cells, fibroblasts, keratinocytes and cell lines.

In preferred embodiments of the method or the use according to the invention, the cells are displaying α5β1 integrins on their cell surface; and the cell-binding motif of the recombinant fusion protein has selectivity for α5β1 integrins.

BRIEF DESCRIPTION OF THE DRAWINGS

FIG. 9 shows a sequence alignment of spidroin C-terminal domains.

LIST OF APPENDED SEQUENCES

Figure 1:
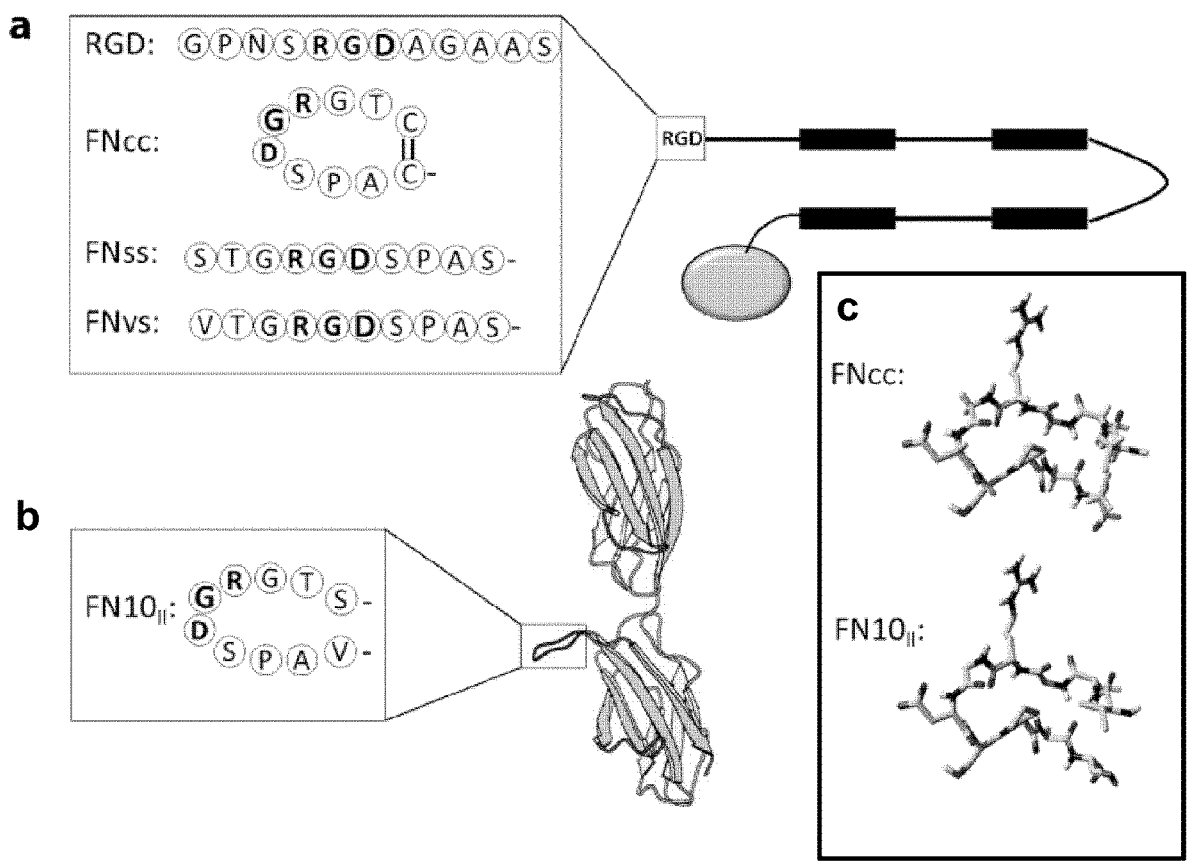
FIG. 1 illustrates silk constructs with cell binding motifs derived from fibronectin.

| SEQ ID NO: | |
|---|---|
| 1 | RepCT (4RepCT, WT) (DNA) |
| 2 | RepCT (4RepCT, WT) |
| 3 | CT |
| 4 | consensus CT sequence |
| 5 | repetitive sequence from Euprosthenops australis MaSp1 |
| 6 | consensus G segment sequence 1 |
| 7 | consensus G segment sequence 2 |
| 8 | consensus G segment sequence 3 |
| 9 | $FN_{VS}$, native fibronectin RGD cell-binding motif |
| 10 | $FN_{CC}$ |
| 11 | $FN_{SS}$ |
| 12 | linear RGD cell-binding motif, Widhe et al. (2013)* |
| 13 | $FN_{CC}$-4RepCT |
| 14 | $FN_{SS}$-4RepCT |
| 15 | $FN_{VS}$-4RepCT |
| 16 | RGD-4RepCT, Widhe et al. (2013)* |
| 17 | $FN_{CC}$-4RepCT (DNA) |
| 18 | $FN_{SS}$-4RepCT (DNA) |
| 19 | $FN_{VS}$-4RepCT(DNA) |
| 20 | RGD-4RepCT, Widhe et al. (2013) (DNA)* |
| 21-24 | RGD peptides with glycine spacer |
| 25-28 | Linker peptides |
| 29 | CT *Euprosthenops* sp MaSp1 |
| 30 | CT *Euprosthenops australis* MaSp1 |
| 31 | CT *Argiope trifasciata* MaSp1 |
| 32 | CT *Cyrtophora moluccensis* Sp1 |
| 33 | CT *Latrodectus geometricus* MaSp1 |
| 34 | CT *Latrodectus hesperus* MaSp1 |
| 35 | CT *Macrothele holsti* Sp1 |
| 36 | CT *Nephila clavipes* MaSp1 |
| 37 | CT *Nephila pilipes* MaSp1 |
| 38 | CT *Nephila madagascariensis* MaSp1 |
| 39 | CT *Nephila senegalensis* MaSp1 |
| 40 | CT *Octonoba varians* Sp1 |
| 41 | CT *Psechrus sinensis* Sp1 |
| 42 | CT *Tetragnatha kauaiensis* MaSp1 |
| 43 | CT *Tetragnatha versicolor* MaSp1 |
| 44 | CT *Araneus bicentenarius* Sp2 |
| 45 | CT *Argiope amoena* MaSp2 |
| 46 | CT *Argiope aurantia* MaSp2 |
| 47 | CT *Argiope trifasciata* MaSp2 |
| 48 | CT *Gasteracantha mammosa* MaSp2 |
| 49 | CT *Latrodectus geometricus* MaSp2 |
| 50 | CT *Latrodectus hesperus* MaSp2 |
| 51 | CT *Nephila clavipes* MaSp2 |
| 52 | CT *Nephila madagascariensis* MaSp2 |
| 53 | CT *Nephila senegalensis* MaSp2 |
| 54 | CT *Dolomedes tenebrosus* Fb1 |
| 55 | CT *Dolomedes tenebrosus* Fb2 |
| 56 | CT *Araneus diadematus* ADF-1 |
| 57 | CT *Araneus diadematus* ADF-2 |
| 58 | CT *Araneus diadematus* ADF-3 |
| 59 | CT *Araneus diadematus* ADF-4 |
| 60 | STGRGDSPAV ($FN10_{II}$) |

*Widhe M et al., Biomaterials 34(33): 8223-8234 (2013)

DETAILED DESCRIPTION OF THE INVENTION

Recombinantly produced spider silk and numerous other materials are useful as matrices for culture of mammalian cells. The inclusion of cell adhesion motifs derived from the extracellular matrix (ECM) into such materials increases cell attachment and proliferation by interaction with integrins on the cell surface. The integrins do not just confer the physical connection between cells and the surrounding, but also mediate signals controlling for example cell growth, polarity, proliferation and survival. Moreover, the integrins are essential for cell migration by acting as the cells' "feet".

The most widely characterized cell adhesion motif is the RGD peptide, first discovered in fibronectin. The RGD motif is found also in many other molecules of the natural ECM, for example in vitronectin, fibrinogen and in cryptic sites of both collagen I and several of the laminin a chains. Almost half of the known integrins, including α3β1, α5β1, α8β1, αvβ1, αIIbβ3, αvβ3, αvβ5, αvβ6a and αvβ8, have been shown to bind ECM in a RGD-dependent manner. However, after initial proofs of RGD as general cell adhesion motif, it soon became clear that integrins in general bind with magnitudes higher affinity to larger RGD containing proteins than to short RGD peptides. The preferred conditions for binding also seem to vary between different integrins.

The present invention is based on a designed cell-binding motif. Without wishing to be bound to any specific theory, it is contemplated that the cell-binding motif presented herein imitates the α5β1-specific RGD loop motif of fibronectin by positioning cysteines in precise positions adjacent to the RGD sequence to allow formation of a disulphide-bridge to constrain the chain into a similar type of turn loop. This cyclic RGD cell-binding motif increases the cell adhesion efficacy to a matrix made of a protein containing the cell-binding motif, such as a recombinantly produced spider silk protein or a synthetic peptide.

The term "cyclic" as used herein refers to a peptide wherein two amino acid residues are covalently bonded via their side chains, more specifically through a disulfide bond between two cysteine residues.

It is shown herein that the cell adhesive properties of a material is significantly enhanced by introducing the cyclic RGD cell-binding motif on a cysteine linked loop compared to when a linear RGD peptide is added. In addition, the cyclic RGD cell-binding motif presented herein promotes both proliferation of and migration by primary cells. Human primary cells cultured on a cell scaffold material containing the cyclic RGD cell-binding motif showed increased attachment, spreading, stress fiber formation and focal adhesions compared to the same material containing a linear RGD peptide.

The cyclic RGD cell-binding motif presented herein is also suitable for preparing free-standing matrices, in particular matrices containing spider silk, on which cells could readily form a monolayer culture. Such free-standing matrices are useful for cell sheet transfer. Thus, a material containing the cyclic RGD cell-binding motif presented herein, such as a spider silk material, is useful for both an in vitro setting, where adherent cells need to be expanded efficiently, and in an in vivo situation where cells need to be transferred as a cell sheet to e.g. a wound area. The results also support that a material containing the cyclic RGD cell-binding motif presented herein, such as a spider silk material, can efficiently attract inherent cells for migration into a wound area, e.g. from the wound edges from where dermal keratinocytes are usually recruited during wound healing. Cell binding to a cell scaffold containing the cyclic RGD cell-binding motif presented herein is demonstrated to involve the α5β1 integrin, and to support proliferation and migration of keratinocytes.

The present inventor used DNA technology to modify the cell-binding motif of fibronectin, where the RGD motif is presented on a turn loop. This was accomplished with the amino acid sequence flanking RGD in the tenth type III domain of fibronectin as base (FIG. 1b). Firstly, the same decapeptide (VTGRGDSPAS; SEQ ID NO: 9) as in the turn loop of fibronectin was introduced N-terminally to a protein to yield a construct denoted $FN_{VS}$ (FIG. 1a). Without wishing to be bound to any specific theory, it was hypothesized that the cell-binding motif could be made more efficient by positioning the valine and serine residue situated 3 positions before and 4 positions after the RGD motif respectively, spatially very close to each other. The present inventor therefore mutated these two residues to cysteines (FIG. 1a, c), so that the RGD containing motif is flanked by one cysteine on each side. The cysteines are spatially less than 2 Å apart, and thus connect the peptide chain into a disulphide bridged loop (denoted $FN_{CC}$; SEQ ID NO: 10). As control, a variant with the two cysteines exchanged to serines was also constructed (denoted $FN_{SS}$; SEQ ID NO: 11). The present inventor investigated the effect of these FN motifs, when introduced into protein matrices, on various mechanisms of early attachment (including spreading, stress fiber formation, focal adhesions and integrin binding) in primary adherent cells of human origin. It was found that the $FN_{CC}$ variant containing a cyclic RGD cell-binding motif increases the cell adhesion efficacy to a matrix made of a protein containing the cell-binding motif as compared to the controls $FN_{VS}$ and $FN_{SS}$.

It can be seen from the crystal structure of the ninth and tenth domain of fibronectin determined by Leahy D J et al., Cell 84(1): 155-164 (1996), that the valine and serine residue situated 3 positions before and 4 positions after the RGD motif respectively, are located spatially very close to each other (FIG. 1c). Again without wishing to be bound to any specific theory, it is therefore considered that the cell-binding motif presented herein imitates the α5β1-specific RGD loop motif of fibronectin by positioning cysteines adjacent to the RGD sequence to allow formation of a disulphide-bridge to constrain the chain into a similar type of turn loop. As a consequence, it is concluded that the cell-binding motif presented herein is in particular selective for α5β1 integrins.

Thus, the relevant silk constructs with cell binding motifs derived from fibronectin are illustrated in FIG. 1. FIG. 1a schematically shows the silk protein 4RepCT with different RGD motifs genetically introduced to its N-terminus. "RGD" in FIG. 1a denotes the RGD containing peptide (SEQ ID NO 12) used in Widhe M et al., Biomaterials 34(33): 8223-8234 (2013). "$FN_{VS}$" denotes the RGD-containing decapeptide from fibronectin (SEQ ID NO: 9). "$FN_{CC}$" denotes the same peptide with V and S exchanged to C (SEQ ID NO: 10). "$FN_{SS}$" denotes the same peptide with V and S exchanged to S (SEQ ID NO: 11). FIG. 1b shows the structure of the 9th and 10th domain of fibronectin, displaying the turn loop containing the RGD motif (SEQ ID NO: 60). FIG. 1c shows a structure model of the RGD loop taken from fibronectin, with the residues V and S mutated to C (adapted from 1FNF.pdb).

The cell-binding motif presented herein is selective for binding to integrins presented on the cell surface, such as and preferably to α5β1 integrins. In the context of the present invention, "specific" or "selective" interaction of the cell-binding motif with its target integrin means that the interaction is such that a distinction between specific and non-specific, or between selective and non-selective, interaction becomes meaningful. The interaction between two proteins is sometimes measured by the dissociation constant. The dissociation constant describes the strength of binding (or affinity) between two molecules. Typically the dissociation constant between an antibody and its antigen is from $10^{-7}$ to $10^{-11}$ M. However, high specificity does not necessarily require high affinity. Molecules with low affinity (in the molar range) for its counterpart have been shown to be as specific as molecules with much higher affinity. In the case of the present invention, a specific or selective interaction refers to the extent to which a particular method can be used to preferentially bind to a specific protein or cell type, displaying the target integrin or a fragment thereof, under given conditions in the presence of other proteins or cells in a sample of a naturally occurring or processed biological or biochemical fluid. In other words, specificity or selectivity is the capacity to distinguish between related proteins and cell types displaying the related proteins. Specific and selective are sometimes used interchangeably in the present description.

The cyclic RGD cell-binding motif is comprising, or consisting of, the amino acid sequence

$C^1X^1X^2RGDX^3X^4X^5C^2$ wherein
each of $X^1$, $X^2$, $X^3$, $X^4$ and $X^5$ are independently selected from natural amino acid residues other than cysteine; and $C^1$ and $C^2$ are connected via a disulphide bond.

It is preferred that each of $X^1$, $X^2$, $X^3$, $X^4$ and $X^5$ are independently selected from the group of amino acid residues consisting of: G, A, V, S, T, D, E, M, P, N and Q.

It is more preferred that each of $X^1$ and $X^3$ are independently selected from the group of amino acid residues consisting of: G, S, T, M, N and Q; and that each of $X^2$, $X^4$ and $X^5$ are independently selected from the group of amino acid residues consisting of: G, A, V, S, T, P, N and Q. The resulting cell-binding motif does not contain any charged or bulky residues which could be disadvantageous for the cell-binding efficacy.

It is in particular preferred that:
X$^1$ is selected from the group of amino acid residues consisting of: G, S, T, N and Q;
X$^3$ is selected from the group of amino acid residues consisting of: S, T and Q; and
each of X$^2$, X$^4$ and X$^5$ are independently selected from the group of amino acid residues consisting of: G, A, V, S, T, P and N.

It is more preferred that
X$^1$ is S or T;
X$^2$ is G, A or V; preferably G or A; more preferably G;
X$^3$ is S or T; preferably S;
X$^4$ is G, A, V or P; preferably G or P; more preferably P; and
X$^5$ is G, A or V; preferably G or A; more preferably A.

A particularly preferred cyclic RGD cell-binding motif is comprising, or consisting of, the amino acid sequence CTGRGDSPAC (FN$_{CC}$; SEQ ID NO: 10).

Further preferred cyclic RGD cell-binding motifs according to the invention display at least 60%, such as at least 70%, such as at least 80%, such as at least 90% identity to CTGRGDSPAC (FN$_{CC}$; SEQ ID NO: 10), with the proviso that position 1 and 10 are always C; position 4 is always R; position 5 is always G; position 6 is always D; and positions 2-3 and 7-9 are never cysteine. It is understood that the non-identical positions among positions 2-3 and 7-9 can be freely selected as set out above.

The thus identified cyclic RGD cell-binding motif is useful in any recombinant or synthetic protein or peptide so as to provide selective binding to integrins, in particular α5β1 integrins. Thus, there is provided a recombinant protein comprising the cell-binding motif with selectivity for integrins, such as for α5β1 integrins. The recombinant protein is useful for the cultivation of cells, e.g. mammalian cells, displaying integrins, in particular α5β1 integrins, on their cell surface.

Without limitation thereto, preferred cells are selected from skeletal muscle cells, endothelial cells, stem cells, fibroblasts, keratinocytes and cell lines.

Fibronectin is recognized by at least ten of the cell surface receptors of the integrin family, among which five (α3β1, α4β1, α5β1, α8β1, αvβ1) include the β1 subunit. The α5 subunit is found only in combination with β1 and the α5β1 integrin is unique since it is specialized for binding of fibronectin only, and therefore originally denoted the fibronectin receptor. The specific interaction between α5β1 and fibronectin seem to be fundamental for vertebrate development since lack of either α5β1 or fibronectin results in early embryonic lethality. Fibronectin and α5β1 has also been shown important in the wound repair process of airway epithelium, where both have been observed to be exclusively expressed by the migratory cells in the wounded area, and to play a critical role in endothelial cell migration in vitro and angiogenesis in vivo.

There is provided a recombinant or synthetic protein or peptide comprising a cell-binding motif with selectivity for integrins, such as for α5β1 integrins, wherein the cell-binding motif is as set out above.

A preferred recombinant protein is comprising a cell-binding motif with selectivity for integrins, such as for α5β1 integrins, wherein the cell-binding motif has the amino acid sequence

C$^1$X$^1$X$^2$RGDX$^3$X$^4$X$^5$C$^2$ wherein
X$^1$ is selected from the group of amino acid residues consisting of: G, S, T, N and Q;
X$^3$ is selected from the group of amino acid residues consisting of: S, T and Q; and
each of X$^2$, X$^4$ and X$^5$ are independently selected from the group of amino acid residues consisting of: G, A, V, S, T, P and N; and
C$^1$ and C$^2$ are connected via a disulphide bond.

Preferred embodiments of the cell-binding motif is presented herein. In particular, it is preferred that:
X$^1$ is S or T; preferably T;
X$^2$ is G, A or V; preferably G or A; more preferably G;
X$^3$ is S or T; preferably S
X$^4$ is G, A, V or P; preferably G or P; more preferably P;
X$^5$ is G, A or V; preferably G or A; more preferably A.

A specific preferred cell-binding motif is comprising the amino acid sequence CTGRGDSPAC (FN$_{CC}$; SEQ ID NO: 10).

The recombinant protein is useful in cell scaffold materials. It is also useful for the cultivation of cells displaying integrins on their cell surface, in particular, wherein the cells are displaying α5β1 integrins on their cell surface.

Without limitation thereto, preferred cells are selected from skeletal muscle cells, endothelial cells, stem cells, fibroblasts, keratinocytes and cell lines.

The recombinant or synthetic protein may also be constituted by a shorter peptide comprising or even consisting of the cell-binding motif, e.g. containing 10-50, or 10-30 amino acid residues. These peptides may be chemically coupled or immobilized to a surface as is well-known in the art. Advantageously, the peptide contains or is coupled to a spacer which allows greater accessibility to the cell-binding motif. The thus immobilized (i.e. not in solution) recombinant protein is surprisingly useful for the cultivation of cells displaying integrins on their cell surface, in particular, wherein the cells are displaying α5β1 integrins on their cell surface.

The cell-binding motif is advantageously presented as part of a fusion protein together with a spider silk protein, in particular a miniature spider silk protein. The terms "spidroins" and "spider silk proteins" are used interchangeably throughout the description and encompass all known spider silk proteins, including major ampullate spider silk proteins which typically are abbreviated "MaSp", or "ADF" in the case of *Araneus diadematus*. These major ampullate spider silk proteins are generally of two types, 1 and 2. These terms furthermore include non-natural proteins with a high degree of identity and/or similarity to the known spider silk proteins.

There is provided a recombinant fusion protein comprising a spidroin fragment and the cell-binding motif with selectivity for integrins, such as for α5β1 integrins, set out above. The spidroin fragment is preferably comprising, or consisting of, the protein moieties REP and CT, wherein
REP is a repetitive fragment of from 70 to 300 amino acid residues, selected from the group consisting of L(AG)$_n$L, L(AG)$_n$AL, L(GA)$_n$L, and L(GA)$_n$GL, wherein
n is an integer from 2 to 10;
each individual A segment is an amino acid sequence of from 8 to 18 amino acid residues, wherein from 0 to 3 of the amino acid residues are not Ala, and the remaining amino acid residues are Ala;
each individual G segment is an amino acid sequence of from 12 to 30 amino acid residues, wherein at least 40% of the amino acid residues are Gly; and
each individual L segment is a linker amino acid sequence of from 0 to 30 amino acid residues; and
CT is a fragment of from 70 to 120 amino acid residues, having at least 70% identity to SEQ ID NO: 3.

The fusion protein according to the invention harbors both a desired selective cell-binding activity in the cell-binding motif and an internal solid support activity in the spidroin fragment. The binding activity of the fusion protein is maintained when it is structurally rearranged to form polymeric, solid structures. These protein structures, or protein polymers, also provides a high and predictable density of the cell-binding motif with selective interaction activity towards integrins, e.g. α5β1 integrins. The thus immobilized cell-binding motif promotes integrin activation and cell binding. The way biomaterials functionalized with RGD stimulate different cell responses is not only affected by the type of RGD motif used, but also the resulting surface concentrations of ligands. Since the rather small silk proteins used in the present study self-assemble into multilayers where each molecule carries an RGD motif, a dense surface presentation is expected. However, if a more sparse surface concentration is desired, any possible surface density can be achieved simply by mixing silk proteins with and without the cyclic RGD cell-binding motif disclosed herein at different ratios, thereby directing the cellular response of interest.

In most of the proteins that have been engineered to contain RGD, the motif has been added as a linear extension either to the N- or C-terminus, thus with a high possibility of exposure and flexibility due to minimal constrain of the chain from the rest of the protein. Several constructs with the RGD motif placed within a protein fold have been made to reduce the flexibility of the RGD motif, but at the same time also reducing its exposure. The cyclic RGD cell-binding motif disclosed herein can advantageously be presented as a linear extension either to the N- or C-terminus, thus with a high possibility of exposure. At the same time, its cyclic properties limit the flexibility and is believed to contribute to highly useful cell binding properties. Furthermore, the covalent incorporation of the peptide into a folded protein chain might have contributed to the apparently efficient integrin-mediated cell binding, involving α5β1.

The term "fusion protein" implies here a protein that is made by expression from a recombinant nucleic acid, i.e. DNA or RNA that is created artificially by combining two or more nucleic acid sequences that would not normally occur together (genetic engineering). The fusion proteins according to the invention are recombinant proteins, and they are therefore not identical to naturally occurring proteins. In particular, wildtype spidroins are not fusion proteins according to the invention, because they are not expressed from a recombinant nucleic acid as set out above. The combined nucleic acid sequences encode different proteins, partial proteins or polypeptides with certain functional properties. The resulting fusion protein, or recombinant fusion protein, is a single protein with functional properties derived from each of the original proteins, partial proteins or polypeptides. Furthermore, the fusion protein according to the invention and the corresponding genes are chimeric, i.e. the protein/gene moieties are derived from at least two different species.

The fusion protein typically consists of from 170 to 2000 amino acid residues, such as from 170 to 1000 amino acid residues, such as from 170 to 600 amino acid residues, preferably from 170 to 500 amino acid residues, such as from 170 to 400 amino acid residues. The small size is advantageous because longer proteins containing spider silk protein fragments may form amorphous aggregates, which require use of harsh solvents for solubilisation and polymerisation.

The fusion protein may contain one or more linker peptides, or L segments. The linker peptide(s) may be arranged between any moieties of the fusion protein, e.g. between the REP and CT moieties, at either terminal end of the fusion protein or between the spidroin fragment and the cell-binding motif. The linker(s) may provide a spacer between the functional units of the fusion protein, but may also constitute a handle for identification and purification of the fusion protein, e.g. a His and/or a Trx tag. If the fusion protein contains two or more linker peptides for identification and purification of the fusion protein, it is preferred that they are separated by a spacer sequence, e.g. His6-spacer-His6-. The linker may also constitute a signal peptide, such as a signal recognition particle, which directs the fusion protein to the membrane and/or causes secretion of the fusion protein from the host cell into the surrounding medium. The fusion protein may also include a cleavage site in its amino acid sequence, which allows for cleavage and removal of the linker(s) and/or other relevant moieties. Various cleavage sites are known to the person skilled in the art, e.g. cleavage sites for chemical agents, such as CNBr after Met residues and hydroxylamine between Asn-Gly residues, cleavage sites for proteases, such as thrombin or protease 3C, and self-splicing sequences, such as intein self-splicing sequences.

The spidroin fragment and the cell-binding motif are linked directly or indirectly to one another. A direct linkage implies a direct covalent binding between the moieties without intervening sequences, such as linkers. An indirect linkage also implies that the moieties are linked by covalent bonds, but that there are intervening sequences, such as linkers and/or one or more further moieties, e.g. 1-2 NT moieties.

The cell-binding motif may be arranged internally or at either end of the fusion protein, i.e. C-terminally arranged or N-terminally arranged. It is preferred that the cell-binding motif is arranged at the N-terminal end of the fusion protein. If the fusion protein contains one or more linker peptide(s) for identification and purification of the fusion protein, e.g. a His or Trx tag(s), it is preferred that it is arranged at the N-terminal end of the fusion protein.

A preferred fusion protein has the form of an N-terminally arranged cell-bonding motif, coupled by a linker peptide of 0-30 amino acid residues, such as 0-10 amino acid residues, to a REP moiety. Optionally, the fusion protein has an N-terminal or C-terminal linker peptide, which may contain a purification tag, such as a His tag, and a cleavage site.

The recombinant protein is useful in cell scaffold materials. It is also useful for the cultivation of cells displaying integrins on their cell surface, in particular wherein the cells are displaying α5β1 integrins on their cell surface.

Without limitation thereto, preferred cells are selected from skeletal muscle cells, endothelial cells, stem cells, fibroblasts, keratinocytes and cell lines.

Without wishing to be bound to any specific theory, it is contemplated that the cell-binding motif is functionally displayed on the surface of the resulting cell scaffold material, which is herein surprisingly shown to be advantageous for the binding capacity with respect to mammalian cells, c.f. Examples 6-9.

The prominent positive effect of the cell scaffold material containing the cyclic RGD cell-binding motif presented herein is evident already at initial attachment (within 0.5-3 h) of primary cells. Strong and rapid attachment of cells onto a material has been suggested to be of considerable importance when it comes to various clinical applications, where the present environment for cells is far from optimal, and fast establishment is necessary for cell survival. One example is the stressful milieu of a chronic wound, often with high bacterial load and necrosis. Here, migrating keratinocytes might benefit from the support of a suitably designed biomaterial constituting containing the cyclic RGD cell-binding motif, such as as a spider silk fusion protein. Also in clinical settings where the close surroundings imply physical stress, like velocity of passing fluids, e.g. blood passing the stent in a heart or a vessel implant, a material that facilitates for the endothelial cells to rapidly and firmly attach to an implant could be critical, and thus even decisive for a successful outcome.

A scaffold intended for tissue engineering will obviously be subjected to harsher handling and environments than in a cell culture setting, why the observed improved stability of the spider silk material containing the cyclic RGD cell-binding motif is valuable. This increase in stability compared to the wild type silk allows preparation of transferable scaffolds, e.g. free-standing films as demonstrated herein.

The protein moiety REP is fragment with a repetitive character, alternating between alanine-rich stretches and glycine-rich stretches. The REP fragment generally contains more than 70, such as more than 140, and less than 300, preferably less than 240, such as less than 200, amino acid residues, and can itself be divided into several L (linker) segments, A (alanine-rich) segments and G (glycine-rich) segments, as will be explained in more detail below. Typically, said linker segments, which are optional, are located at the REP fragment terminals, while the remaining segments are in turn alanine-rich and glycine-rich. Thus, the REP fragment can generally have either of the following structures, wherein n is an integer:

$L(AG)_nL$, such as $LA_1G_1A_2G_2A_3G_3A_4G_4A_5G_5L$;
$L(AG)_nAL$, such as $LA_1G_1A_2G_2A_3G_3A_4G_4A_5G_5A_6L$;
$L(GA)_nL$, such as $LG_1A_1G_2A_2G_3A_3G_4A_4G_5A_5L$; or
$L(GA)_nGL$, such as $LG_1A_1G_2A_2G_3A_3G_4A_4G_5A_5G_6L$.

It follows that it is not critical whether an alanine-rich or a glycine-rich segment is adjacent to the N-terminal or C-terminal linker segments. It is preferred that n is an integer from 2 to 10, preferably from 2 to 8, also preferably from 4 to 8, more preferred from 4 to 6, i.e. n=4, n=5 or n=6.

In some embodiments, the alanine content of the REP fragment is above 20%, preferably above 25%, more preferably above 30%, and below 50%, preferably below 40%, more preferably below 35%. It is contemplated that a higher alanine content provides a stiffer and/or stronger and/or less extendible fiber.

In certain embodiments, the REP fragment is void of proline residues, i.e. there are no Pro residues in the REP fragment.

Turning now to the segments that constitute the REP fragment, it is emphasized that each segment is individual, i.e. any two A segments, any two G segments or any two L segments of a specific REP fragment may be identical or may not be identical. Thus, it is not a general feature of the spidroin that each type of segment is identical within a specific REP fragment. Rather, the following disclosure provides the skilled person with guidelines how to design individual segments and gather them into a REP fragment, which is a part of a functional spider silk protein useful in a cell scaffold material.

Each individual A segment is an amino acid sequence having from 8 to 18 amino acid residues. It is preferred that each individual A segment contains from 13 to 15 amino acid residues. It is also possible that a majority, or more than two, of the A segments contain from 13 to 15 amino acid residues, and that a minority, such as one or two, of the A segments contain from 8 to 18 amino acid residues, such as 8-12 or 16-18 amino acid residues. A vast majority of these amino acid residues are alanine residues. More specifically, from 0 to 3 of the amino acid residues are not alanine residues, and the remaining amino acid residues are alanine residues. Thus, all amino acid residues in each individual A segment are alanine residues, with no exception or with the exception of one, two or three amino acid residues, which can be any amino acid. It is preferred that the alanine-replacing amino acid(s) is (are) natural amino acids, preferably individually selected from the group of serine, glutamic acid, cysteine and glycine, more preferably serine. Of course, it is possible that one or more of the A segments are all-alanine segments, while the remaining A segments contain 1-3 non-alanine residues, such as serine, glutamic acid, cysteine or glycine.

In an embodiment, each A segment contains 13-15 amino acid residues, including 10-15 alanine residues and 0-3 non-alanine residues as described above. In a more preferred embodiment, each A segment contains 13-15 amino acid residues, including 12-15 alanine residues and 0-1 non-alanine residues as described above.

It is preferred that each individual A segment has at least 80%, preferably at least 90%, more preferably 95%, most preferably 100% identity to an amino acid sequence selected from the group of amino acid residues 7-19, 43-56, 71-83, 107-120, 135-147, 171-183, 198-211, 235-248, 266-279, 294-306, 330-342, 357-370, 394-406, 421-434, 458-470, 489-502, 517-529, 553-566, 581-594, 618-630, 648-661, 676-688, 712-725, 740-752, 776-789, 804-816, 840-853, 868-880, 904-917, 932-945, 969-981, 999-1013, 1028-1042 and 1060-1073 of SEQ ID NO: 5. Each sequence of this group corresponds to a segment of the naturally occurring sequence of *Euprosthenops australis* MaSp1 protein, which is deduced from cloning of the corresponding cDNA, see WO2007/078239. Alternatively, each individual A segment has at least 80%, preferably at least 90%, more preferably 95%, most preferably 100% identity to an amino acid sequence selected from the group of amino acid residues 25-36, 55-69, 84-98, 116-129 and 149-158 of SEQ ID NO: 2. Each sequence of this group corresponds to a segment of expressed, non-natural spider silk proteins, which proteins have the capacity to form silk fibers under appropriate conditions. Thus, in certain embodiments of the spidroin, each individual A segment is identical to an amino acid sequence selected from the above-mentioned amino acid segments. Without wishing to be bound by any particular theory, it is envisaged that A segments according to the invention form helical structures or beta sheets.

Furthermore, it has been concluded from experimental data that each individual G segment is an amino acid sequence of from 12 to 30 amino acid residues. It is preferred that each individual G segment consists of from 14 to 23 amino acid residues. At least 40% of the amino acid residues of each G segment are glycine residues. Typically the glycine content of each individual G segment is in the range of 40-60%.

It is preferred that each individual G segment has at least 80%, preferably at least 90%, more preferably 95%, most preferably 100% identity to an amino acid sequence selected from the group of amino acid residues 20-42, 57-70, 84-106, 121-134, 148-170, 184-197, 212-234, 249-265, 280-293, 307-329, 343-356, 371-393, 407-420, 435-457, 471-488, 503-516, 530-552, 567-580, 595-617, 631-647, 662-675, 689-711, 726-739, 753-775, 790-803, 817-839, 854-867, 881-903, 918-931, 946-968, 982-998, 1014-1027, 1043-1059 and 1074-1092 of SEQ ID NO: 5. Each sequence of this group corresponds to a segment of the naturally occurring sequence of *Euprosthenops australis* MaSp1 protein, which is deduced from cloning of the corresponding cDNA, see WO2007/078239. Alternatively, each individual G segment has at least 80%, preferably at least 90%, more preferably 95%, most preferably 100% identity to an amino acid sequence selected from the group of amino acid residues 1-24, 37-54, 70-83, 99-115 and 130-148 of SEQ ID NO: 2. Each sequence of this group corresponds to a segment of expressed, non-natural spider silk proteins, which proteins have the capacity to form silk fibers under appropriate conditions. Thus, in certain embodiments of the spidroin in the cell scaffold material, each individual G segment is identical to an amino acid sequence selected from the above-mentioned amino acid segments.

In certain embodiments, the first two amino acid residues of each G segment are not -Gln-Gln-.

There are three subtypes of the G segment. This classification is based upon careful analysis of the *Euprosthenops australis* MaSp1 protein sequence (see WO2007/078239), and the information has been employed and verified in the construction of novel, non-natural spider silk proteins.

The first subtype of the G segment is represented by the amino acid one letter consensus sequence GQG(G/S)QGG (Q/Y)GG (L/Q)GQGGYGQGA GSS (SEQ ID NO: 6). This first, and generally the longest, G segment subtype typically contains 23 amino acid residues, but may contain as little as 17 amino acid residues, and lacks charged residues or contain one charged residue. Thus, it is preferred that this first G segment subtype contains 17-23 amino acid residues, but it is contemplated that it may contain as few as 12 or as many as 30 amino acid residues. Without wishing to be bound by any particular theory, it is envisaged that this subtype forms coil structures or $3_1$-helix structures. Representative G segments of this first subtype are amino acid residues 20-42, 84-106, 148-170, 212-234, 307-329, 371-393, 435-457, 530-552, 595-617, 689-711, 753-775, 817-839, 881-903, 946-968, 1043-1059 and 1074-1092 of SEQ ID NO: 5. In certain embodiments, the first two amino acid residues of each G segment of this first subtype according to the invention are not -Gln-Gln-.

The second subtype of the G segment is represented by the amino acid one letter consensus sequence GQGGQGQG (G/R)Y GQG(A/S)G(S/G)S (SEQ ID NO: 7). This second, generally mid-sized, G segment subtype typically contains 17 amino acid residues and lacks charged residues or contain one charged residue. It is preferred that this second G segment subtype contains 14-20 amino acid residues, but it is contemplated that it may contain as few as 12 or as many as 30 amino acid residues. Without wishing to be bound by any particular theory, it is envisaged that this subtype forms coil structures. Representative G segments of this second subtype are amino acid residues 249-265, 471-488, 631-647 and 982-998 of SEQ ID NO: 5.

The third subtype of the G segment is represented by the amino acid one letter consensus sequence G(R/Q)GQG(G/R)YGQG (A/S/V)GGN (SEQ ID NO: 8). This third G segment subtype typically contains 14 amino acid residues, and is generally the shortest of the G segment subtypes. It is preferred that this third G segment subtype contains 12-17 amino acid residues, but it is contemplated that it may contain as many as 23 amino acid residues. Without wishing to be bound by any particular theory, it is envisaged that this subtype forms turn structures. Representative G segments of this third subtype are amino acid residues 57-70, 121-134, 184-197, 280-293, 343-356, 407-420, 503-516, 567-580, 662-675, 726-739, 790-803, 854-867, 918-931, 1014-1027 of SEQ ID NO: 5.

Thus, in preferred embodiments of the spidroin in the cell scaffold material, each individual G segment has at least 80%, preferably 90%, more preferably 95%, identity to an amino acid sequence selected from SEQ ID NO: 6, SEQ ID NO: 7 and SEQ ID NO: 8.

In an embodiment of the alternating sequence of A and G segments of the REP fragment, every second G segment is of the first subtype, while the remaining G segments are of the third subtype, e.g. . . . $A_1G_{short}A_2G_{long}A_3G_{short}A_4G_{long}A_5G_{short}$ . . . . In another embodiment of the REP fragment, one G segment of the second subtype interrupts the G segment regularity via an insertion, e.g. . . . $A_1G_{short}A_2G_{long}A_3G_{mid}A_4G_{short}A_5G_{long}$ . . . .

Each individual L segment represents an optional linker amino acid sequence, which may contain from 0 to 30 amino acid residues, such as from 0 to 20 amino acid residues. While this segment is optional and not critical for the function of the spider silk protein, its presence still allows for fully functional spider silk proteins and polymers thereof which form fibers, films, foams and other structures. There are also linker amino acid sequences present in the repetitive part (SEQ ID NO: 5) of the deduced amino acid sequence of the MaSp1 protein from *Euprosthenops australis*. In particular, the amino acid sequence of a linker segment may resemble any of the described A or G segments, but usually not sufficiently to meet their criteria as defined herein.

As shown in WO 2007/078239, a linker segment arranged at the C-terminal part of the REP fragment can be represented by the amino acid one letter consensus sequences ASASAAASAA STVANSVS (SEQ ID NO: 22) and ASAASAAA (SEQ ID NO: 23), which are rich in alanine. In fact, the second sequence can be considered to be an A segment according to the definition herein, whereas the first sequence has a high degree of similarity to A segments according to this definition. Another example of a linker segment has the one letter amino acid sequence GSAMGQGS (SEQ ID NO: 24), which is rich in glycine and has a high degree of similarity to G segments according to the definition herein. Another example of a linker segment is SASAG (SEQ ID NO: 25).

Representative L segments are amino acid residues 1-6 and 1093-1110 of SEQ ID NO: 5; and amino acid residues 159-165 of SEQ ID NO: 2, but the skilled person will readily recognize that there are many suitable alternative amino acid sequences for these segments. In one embodiment of the REP fragment, one of the L segments contains 0 amino acids, i.e. one of the L segments is void. In another embodiment of the REP fragment, both L segments contain 0 amino acids, i.e. both L segments are void. Thus, these embodiments of the REP fragments according to the invention may be schematically represented as follows: $(AG)_nL$, $(AG)_nAL$, $(GA)_nL$, $(GA)_nGL$; $L(AG)_n$, $L(AG)_nA$, $L(GA)_n$, $L(GA)_nG$; and $(AG)_n$, $(AG)_nA$, $(GA)_n$, $(GA)_nG$. Any of these REP fragments are suitable for use with any CT fragment as defined below.

The CT fragment of the spidroin in the cell scaffold material has a high degree of similarity to the C-terminal amino acid sequence of spider silk proteins. As shown in WO2007/078239, this amino acid sequence is well conserved among various species and spider silk proteins, including MaSp1 and MaSp2. A consensus sequence of the C-terminal regions of MaSp1 and MaSp2 is provided as SEQ ID NO: 4. In FIG. 9, the following MaSp proteins are aligned, denoted with GenBank accession entries where applicable:

TABLE 1

Spidroin CT fragments

| Species and spidroin | Entry |
|---|---|
| *Euprosthenops* sp MaSp1 (Pouchkina-Stantcheva*) | Cthyb_Esp |
| *Euprosthenops australis* MaSp1 (SEQ ID NO: 3) | CTnat_Eau |
| *Argiope trifasciata* MaSp1 | AF350266_At1 |
| *Cyrtophora moluccensis* Sp1 | AY666062_Cm1 |
| *Latrodectus geometricus* MaSp1 | AF350273_Lg1 |
| *Latrodectus hesperus* MaSp1 | AY953074_Lh1 |
| *Macrothele holsti* Sp1 | AY666068_Mh1 |
| *Nephila clavipes* MaSp1 | U20329_Nc1 |
| *Nephila pilipes* MaSp1 | AY666076_Np1 |
| *Nephila madagascariensis* MaSp1 | AF350277_Nm1 |
| *Nephila senegalensis* MaSp1 | AF350279_Ns1 |
| *Octonoba varians* Sp1 | AY666057_Ov1 |
| *Psechrus sinensis* Sp1 | AY666064_Ps1 |
| *Tetragnatha kauaiensis* MaSp1 | AF350285_Tk1 |
| *Tetragnatha versicolor* MaSp1 | AF350286_Tv1 |
| *Araneus bicentenarius* Sp2 | ABU20328_Ab2 |
| *Argiope amoena* MaSp2 | AY365016_Aam2 |
| *Argiope aurantia* MaSp2 | AF350263_Aau2 |
| *Argiope trifasciata* MaSp2 | AF350267_At2 |
| *Gasteracantha mammosa* MaSp2 | AF350272_Gm2 |
| *Latrodectus geometricus* MaSp2 | AF350275_Lg2 |
| *Latrodectus hesperus* MaSp2 | AY953075_Lh2 |
| *Nephila clavipes* MaSp2 | AY654293_Nc2 |
| *Nephila madagascariensis* MaSp2 | AF350278_Nm2 |
| *Nephila senegalensis* MaSp2 | AF350280_Ns2 |
| *Dolomedes tenebrosus* Fb1 | AF350269_DtFb1 |
| *Dolomedes tenebrosus* Fb2 | AF350270_DtFb2 |
| *Araneus diadematus* ADF-1 | U47853_ADF1 |
| *Araneus diadematus* ADF-2 | U47854_ADF2 |
| *Araneus diadematus* ADF-3 | U47855_ADF3 |
| *Araneus diadematus* ADF-4 | U47856_ADF4 |

*Comparative Biochemistry and Physiology, Part B 138: 371-376 (2004)

It is not critical which specific CT fragment is present in the spider silk protein in the cell scaffold material. Thus, the CT fragment can be selected from any of the amino acid sequences shown in FIG. 9 and Table 1 or sequences with a high degree of similarity. A wide variety of C-terminal sequences can be used in the spider silk protein.

The sequence of the CT fragment has at least 50% identity, preferably at least 60%, more preferably at least 65% identity, or even at least 70% identity, to the consensus amino acid sequence SEQ ID NO: 4, which is based on the amino acid sequences of FIG. 9.

A representative CT fragment is the *Euprosthenops australis* sequence SEQ ID NO: 3 or amino acid residues 180-277 of SEQ ID NO: 13. Thus, in one embodiment, the CT fragment has at least 70%, such as at least 80%, such as at least 85%, preferably at least 90%, such as at least 95%, identity to SEQ ID NO: 3, amino acid residues 180-277 of SEQ ID NO: 13, or any individual amino acid sequence of FIG. 9 and Table 1. For example, the CT fragment may be identical to SEQ ID NO: 3, amino acid residues 180-277 of SEQ ID NO: 13, or any individual amino acid sequence of FIG. 9 and Table 1.

The CT fragment typically consists of from 70 to 120 amino acid residues. It is preferred that the CT fragment contains at least 70, or more than 80, preferably more than 90, amino acid residues. It is also preferred that the CT fragment contains at most 120, or less than 110 amino acid residues. A typical CT fragment contains approximately 100 amino acid residues.

The term "% identity", as used herein, is calculated as follows. The query sequence is aligned to the target sequence using the CLUSTAL W algorithm (Thompson et al, Nucleic Acids Research, 22:4673-4680 (1994)). A comparison is made over the window corresponding to the shortest of the aligned sequences. The amino acid residues at each position are compared, and the percentage of positions in the query sequence that have identical correspondences in the target sequence is reported as % identity.

The term "% similarity", as used herein, is calculated as described above for "% identity", with the exception that the hydrophobic residues Ala, Val, Phe, Pro, Leu, Ile, Trp, Met and Cys are similar; the basic residues Lys, Arg and His are similar; the acidic residues Glu and Asp are similar; and the hydrophilic, uncharged residues Gln, Asn, Ser, Thr and Tyr are similar. The remaining natural amino acid Gly is not similar to any other amino acid in this context.

Throughout this description, alternative embodiments according to the invention fulfill, instead of the specified percentage of identity, the corresponding percentage of similarity. Other alternative embodiments fulfill the specified percentage of identity as well as another, higher percentage of similarity, selected from the group of preferred percentages of identity for each sequence. For example, a sequence may be 70% similar to another sequence; or it may be 70% identical to another sequence; or it may be 70% identical and 90% similar to another sequence.

In a preferred fusion protein according to the invention, the REP-CT fragment has at least 70%, such as at least 80%, such as at least 85%, preferably at least 90%, such as at least 95%, identity to SEQ ID NO: 2 or to amino acid residues 18-277 of SEQ ID NO: 13.

In one preferred fusion protein according to the invention, the protein has at least 70%, such as at least 80%, such as at least 85%, preferably at least 90%, such as at least 95%, identity to SEQ ID NO: 13. In a particularly preferred embodiment, the fusion protein according to the invention is SEQ ID NO: 13.

The cell scaffold material according to the invention comprises a protein or peptide according to the invention displaying the cyclic RGD cell-binding motif. The cyclic RGD cell-binding motif may be exposed from short synthetic peptides or longer synthetic or recombinant proteins, which may in turn be attached to or associated with a matrix or support.

The cell scaffold material preferably comprises a protein polymer, which protein polymer in turn is containing the recombinant fusion protein according to the invention as a repeating structural unit, i.e. the protein polymer contains or consists of a polymer of the recombinant fusion protein according to the invention. This implies that the protein polymer contains or consists of an ordered plurality of fusion proteins according to the invention, typically well above 100 fusion protein units, e.g. 1000 fusion protein units or more. In a preferred embodiment, the cell scaffold material according to the invention consists of the protein polymer.

The magnitude of fusion protein units in the polymer implies that the protein polymer obtains a significant size. In a preferred embodiment, the protein polymer has a size of at least 0.01 µm in at least two dimensions. Thus, the term "protein polymer" as used herein relates to fusion protein polymers having a thickness of at least 0.01 µm, preferably macroscopic polymers that are visible to the human eye, i.e. having a thickness of at least 1 µm. The term "protein polymer" does not encompass unstructured aggregates or precipitates. While monomers/dimers of the fusion protein are water soluble, it is understood that the protein polymers according to the invention are solid structures, i.e. not soluble in water. The protein polymers are comprising monomers of the recombinant fusion proteins according to the invention as a repeating structural unit.

The protein polymer according to the invention is typically provided in a physical form selected from the group consisting of fiber, film, coating, foam, net, fiber-mesh, sphere and capsule. According to one embodiment, it is preferable that the protein polymer according to the invention is a fiber, film or fiber-mesh. According to certain embodiments, it is preferable that the protein polymer has a three-dimensional form, such as a foam or a fiber-mesh. One preferred embodiment involves thin (typically 0.01-0.1 µm thickness) coatings made of the protein polymer, which are useful for coating of stents and other medical devices. The term "foam" is comprising a porous foam with channels connecting the bubbles of the foam, sometimes to the extent that it can even be regarded as a three-dimensional net or mesh of fibers.

In a preferred embodiment, the protein polymer is in a physical form of a free-standing matrix, such as a free-standing film. This is highly useful as it allows for transfer of a cell sheet where needed, e.g. in an in vivo situation where cells need to be transferred as a cell sheet to e.g. a wound area.

The fiber, film or fiber-mesh typically has a thickness of at least 0.1 µm, preferably at least 1 µm. It is preferred that the fiber, film or fiber-mesh has a thickness in the range of 1-400 µm, preferably 60-120 µm. It is preferred that fibers have a length in the range of 0.5-300 cm, preferably 1-100 cm. Other preferred ranges are 0.5-30 cm and 1-20 cm. The fiber has the capacity to remain intact during physical manipulation, i.e. can be used for spinning, weaving, twisting, crocheting and similar procedures. The film is advantageous in that it is coherent and adheres to solid structures, e.g. the plastics in microtiter plates. This property of the film facilitates washing and regeneration procedures and is very useful for separation purposes.

The fusion protein according to the invention harbors both the desired cell-binding activity in the cyclic RGD cell-binding motif and an internal solid support activity in the REP-CT moieties, and these activities are employed in the cell scaffold material. The cell scaffold material provides a high and predictable density of the selective interaction activity towards an organic target. Losses of valuable protein moieties with selective interaction activity are minimized, since all expressed protein moieties are associated with the cell scaffold material.

The polymers which are formed from the fusion proteins according to the invention are solid structures and are useful for their physical properties, especially the useful combination of high strength, elasticity and light weight. A particularly useful feature is that the REP-CT moieties of the fusion protein are biochemically robust and suitable for regeneration, e.g. with acid, base or chaotropic agents, and suitable for heat sterilization, e.g. autoclaving at 120° C. for 20 min. The polymers are also useful for their ability to support cell adherence and growth.

The properties derived from the REP-CT moities are attractive in development of new materials for medical or technical purposes. In particular, the cell scaffold materials according to the invention are useful as scaffolds for cell immobilization, cell culture, cell differentiation, tissue engineering and guided cell regeneration. They are also useful in preparative and analytical separation procedures, such as chromatography, cell capture, selection and culture, active filters, and diagnostics. The cell scaffold materials according to the invention are also useful as in medical devices, such as implants and stents, e.g. as coatings.

In a preferred embodiment, the cell scaffold material comprises a protein polymer, which is consisting of a recombinant fusion protein according to the invention as a repeating structural unit. And in a further preferred embodiment, the cell scaffold material is a protein polymer, which is consisting of a recombinant fusion protein according to the invention as a repeating structural unit.

According to a further aspect, the present invention provides a method for the cultivation of cells, comprising the steps of
  providing a sample of cells;
  applying the sample to a cell scaffold material; and
  maintaining the cell scaffold material having the cells applied thereto under conditions suitable for cell culture;
wherein
the cell scaffold material comprises a protein polymer, which is containing a recombinant protein, such as recombinant fusion protein, according to the invention as a repeating structural unit.

In a preferred embodiment, the cells are displaying $\alpha5\beta1$ integrins on their cell surface; and the cell-binding motif of the recombinant fusion protein has selectivity for $\alpha5\beta1$ integrins.

In preferred embodiments, the recombinant protein containing this cyclic RGD cell-binding motif is immobilized, such as to a solid support (i.e. not in solution), e.g. to the surface of a cell cultivation device or any type of surface where cell binding and growth is desirable. The resulting exposure of the thus immobilized cyclic RGD cell-binding motif surprisingly promotes integrin activation and cell binding to the immobilized recombinant protein containing this cyclic RGD cell-binding motif.

Recombinant fusion proteins containing this cyclic RGD cell-binding motif are particularly useful for the cultivation of cells displaying integrins on their cell surface, since the internal spidroin fragment allows the fusion protein to be brought into ordered polymers and thereby provides an internal solid support to the immobilized (i.e. not in solution) cell-binding motif. The resulting exposure of the immobilized cyclic RGD cell-binding motif surprisingly promotes integrin activation and cell binding to polymers of the recombinant fusion proteins.

Without limitation thereto, preferred cells are selected from skeletal muscle cells, endothelial cells, stem cells, fibroblasts, keratinocytes and cell lines, in particular of human origin.

Without being limited thereto, the method is useful for cultivation of endothelial cells, human mesenchymal stem cells and keratinocytes, in particular of human origin. It is particularly useful for cultivation of keratinocytes.

The cell cultivation method may advantageously be performed both in vitro and in vivo.

The present invention will in the following be further illustrated by the following non-limiting examples.

EXAMPLES

Statistics
  One-way ANOVA followed by Tukey's multiple comparisons test was performed using GraphPad Prism version 6.05 for Windows, GraphPad Software, La Jolla Calif. USA, www.graphpad.com.

Example 1—Genetic Incorporation of Fibronectin-Derived Cell-Binding Motifs into Recombinant Spider Silk The recombinant spider silk protein 4RepCT (SEQ ID NO: 2, herein denoted WT) was genetically functionalized with the RGD containing cell binding motif from the fibronectin type III module 10, in four slightly different versions (FIG. 1). In the first (FN$_{CC}$-4RepCT; SEQ ID NO: 13), two amino acids flanking the RGD sequence were substituted for cysteines to enable loop formation of the motif (CTGRGDSPAC; SEQ ID NO: 10). In the second (FN$_{SS}$-4RepCT; SEQ ID NO: 14), the introduced cysteines were substituted for serines to create a linear control (STGRGDSPAS; SEQ ID NO: 11). Here the amino acid serine was selected due to its resemblance to cysteine, while lacking the ability to form disulfide bonds. In the third (FN$_{VS}$-4RepCT; SEQ ID NO: 15), the original sequence of the fibronectin motif (VTGRGDSPAS; SEQ ID NO: 9) was used as a linear, native control. In the fourth (RGD-4RepCT; SEQ ID NO: 16), the RGD containing peptide (SEQ ID NO 12) used in Widhe M et al., Biomaterials 34(33): 8223-8234 (2013) was used as a further linear control.

The genes encoding the functionalized variants (FN$_{CC}$-4RepCT DNA—SEQ ID NO: 17; FN$_{SS}$-4RepCT DNA—SEQ ID NO: 18; FN$_{VS}$-4RepCT DNA—SEQ ID NO: 19; and RGD-4RepCT DNA—SEQ ID NO: 20) were made by cloning of oligos encoding the different motifs into the vector encoding 4RepCT (4RepCT DNA—SEQ ID NO: 1) and using restriction enzymes. The new sequences were introduced N-terminally to 4RepCT and confirmed by sequencing.

Example 2—Expression of Fusion Proteins Containing Fibronectin-Derived Cell-Binding Motifs Protein production in *E. coli* of the genetic constructs obtained in Example 1 and the following purification were done essentially as described in Hedhammar M et al., Biochemistry 47(11):3407-3417 (2008) and Hedhammar M et al., Biomacromolecules 11: 953-959 (2010).

Briefly, *Escherichia coli* BL21(DE3) cells (Merck Biosciences) with the expression vector for the target protein were grown at 30° C. in Luria-Bertani medium containing kanamycin to an OD$_{600}$ of 0.8-1 and then induced with isopropyl β-D-thiogalactopyranoside and further incubated for at least 2 h. Thereafter, cells were harvested and resuspended in 20 mM Tris-HCl (pH 8.0) supplemented with lysozyme and DNase I. After complete lysis, the supernatants from centrifugation at 15,000 g were loaded onto a column packed with Ni Sepharose (GE Healthcare, Uppsala, Sweden). The column was washed extensively before elution of bound proteins with 300 mM imidazole. Fractions containing the target proteins were pooled and dialyzed against 20 mM Tris-HCl (pH 8.0). The target protein was released from the tags by proteolytic cleavage. To remove the released HisTrxHis tag, the cleavage mixture was loaded onto a second Ni Sepharose column and the flowthrough was collected. The protein content was determined from the absorbance at 280 nm.

The protein solutions obtained were purified from lipopolysaccharides (lps) as described in Hedhammar et al., Biomacromolecules 11:953-959 (2010). The protein solutions were sterile filtered (0.22 µm) before being used to prepare scaffolds (film, foam, coatings or fibers).

The recombinant spider silk proteins were successfully expressed in *E coli* and purified with similar yield and purity as the original 4RepCT (WT; SEQ ID NO: 2).

Example 3—Fabrication of Cell Culture Matrices

After purification, the protein solutions obtained in Example 2 were filter sterilized (0.22 µm) and concentrated by centrifugal filtration (Amicon Ultra, Millipore) before preparation of films, as described in Widhe M et al., Biomaterials 31(36): 9575-9585 (2010) and Widhe M et al., Biomaterials 34(33): 8223-8234 (2013).

Briefly, petri dishes were coated at room temperature with recombinant spider silk solution at a concentration of 0.3 mg/ml to generate films. Foams were made by rapid pipetting of the silk solution, and fibers were formed by gentle wagging in 15 ml tube followed by cutting into smaller pieces.

For studies of early attachment and repopulation, solutions of a protein concentration of 0.3 mg/ml were casted into films in 96- and 24 well cell culture plates respectively (Sarstedt, suspension cells) precoated with 1% pluronic to limit cell adhesion to the plastic surface. In control experiments, a reducing agent (either 5 mM Dithiothreitol, 20 mM β-mercaptoethanol or 10 mM Tris(2-carboxyethyl)phosphine HCl) were added to the protein solutions directly before films were prepared.

For microscopic studies, the proteins were casted as films in chamber glass slides (LabTekII). For Alamar blue experiments, where whole well coverage is desired, the cell culture wells were coated with a covering protein solution of 0.3 mg/ml for 2 h before the liquid was removed. Films and coated surfaces were allowed to dry over night at 25° C. and 30% rh under sterile conditions, then washed twice with sterile 20 mM phosphate buffer, pH 7.4, and pre-incubated with complete cell culture medium for 1 h at 37° C. with 5% CO$_2$ before cell seeding.

Free-standing films were prepared by applying of a droplet of protein solution (3 mg/ml) onto a ~3 mm wide frame of metal wire hanging hooked up in a well of a 96-well plate and allowed to dry over night at 25° C. and 30% rh under sterile conditions.

The control Bovine Fibronectin (Sigma-Aldrich F1137) was coated at recommended concentration (5 µg/cm$^2$) overnight at 37° C.

It was observed that a spider silk protein functionalized with a disulfide-looped RGD motif self-assembles into stable matrices. As shown by the micrographs in FIG. 2a, the FN$_{CC}$-4RepCT (SEQ ID NO: 13) protein could be presented as matrices in the format of fiber (upper), film (middle) and free standing film (lower). Scale bars in FIG. 2a indicate 500 µm (upper & middle) and 1000 µm (lower). Surprisingly, the FN$_{CC}$-4RepCT protein could form fibers, film and foam with appeared higher stability and integrity than noted for linear RGD silk proteins (RGD-4RepCT, SEQ ID NO: 16) and WT silk proteins (4RepCT, SEQ ID NO: 2). With the FN$_{CC}$-4RepCT protein, it was even possible to form free-standing films. The smooth film formats (casted and free-standing) were used in the subsequent cell adhesion experiments to rule out the effects of matrix morphology.

Example 4—Structural Analysis of Matrices

Fourier Transform Infrared Spectroscopy (FTIR) spectra of the fibers, casted films and free-standing films obtained in Example 3 were recorded on a FTIR spectrometer (Bruker). The films were placed on a crystal for measuring IR spectra by attenuated total reflection. For each spectrum 100 scans were averaged. The amide I region was further analyzed to compare the peak height of α-helical (1654 cm$^{-1}$) and β-sheet (1629 cm$^{-1}$) structures, respectively.

Figure 2:
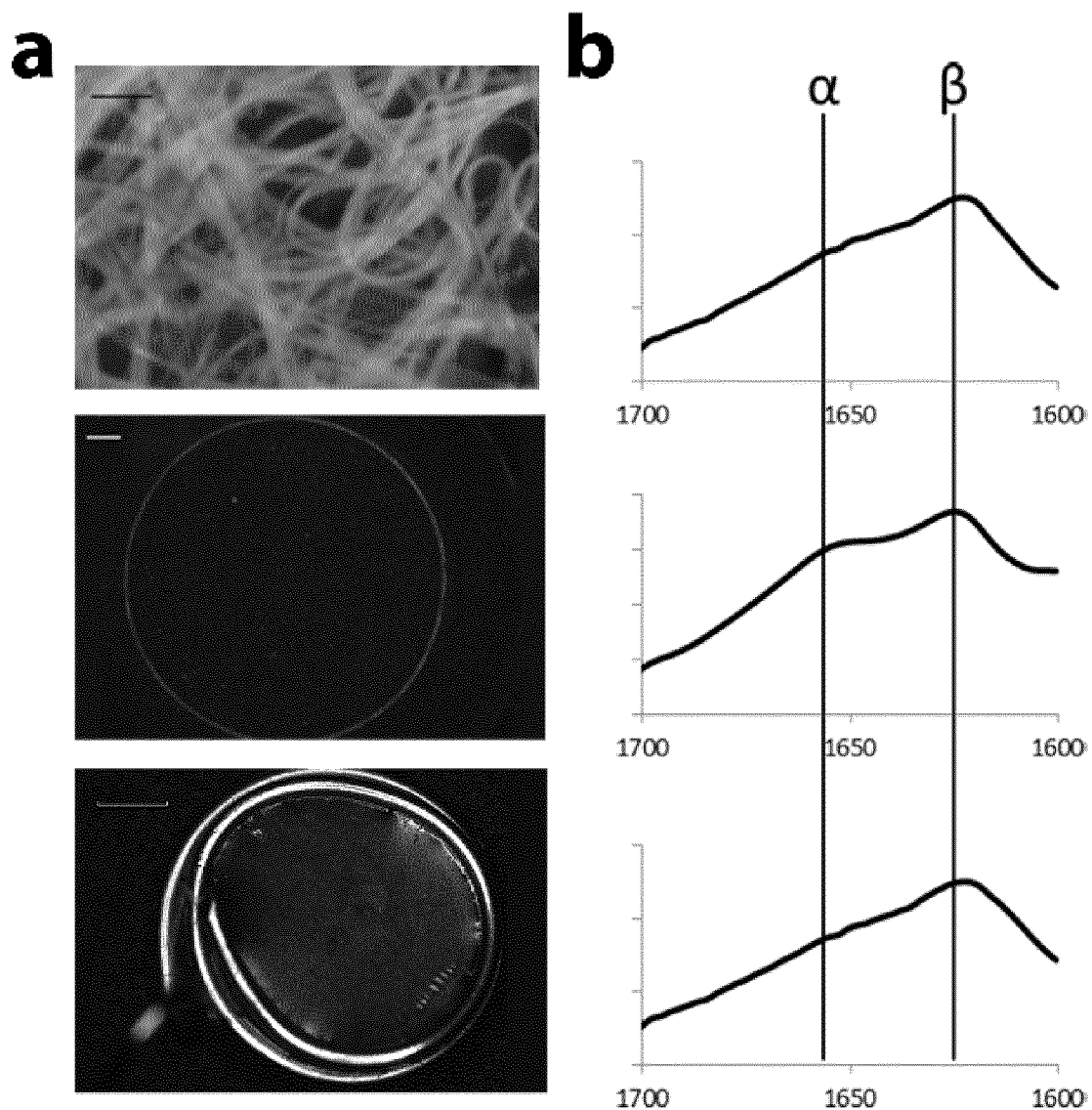
FIG. 2 shows micrographs and FTIR spectra of $FN_{CC}$ silk (SEQ ID NO: 13) matrices.

FIG. 2b shows FTIR spectra of FN$_{CC}$-4RepCT (SEQ ID NO: 13) silk matrices in the format of fiber (upper), film (middle) and free standing film (lower). Peaks for typical signal of α-helix and β-sheet respectively are indicated by lines. Interestingly, the FTIR data in FIG. 2b show that the free-standing films have, oppositely to the casted films, completely converted to β-sheet structure.

Example 5—Cell Culture

Human dermal microvascular endothelial cells (EC), (HDMEC, PromoCell GmbH, Germany) isolated from dermis from adult donor were grown in culture flasks coated with gelatin (Sigma Aldrich) in complete endothelial cell media MV, containing 5% fetal bovine serum (PromoCell GmbH, Germany).

Human mesenchymal stem cells (hMSC, Gibco) from bone marrow were grown in culture flasks coated with CELLstart (Gibco) in complete StemPro MSC serum free medium CTS (Gibco) containing 25 ng/µl fibroblast growth factor 13 (Gibco) and 2 mM Glutamax (Gibco).

Normal human epidermal keratinocytes from adult skin (NHEK-ad) were purchased from Lonza. Subculture, proliferation and migration experiments were done in KGM-Gold (Lonza), containing bovine pituitary extract, whereas adhesion experiments were performed in KGM-CD (chemically defined), supplemented with $CaCl_2$) to give 1.2 mM $Ca^{2+}$.

Keratinocyte and mesenchymal stem cell cultures, as well as experiments, were performed under serum-free conditions to avoid possible interactions between the matrices and serum proteins that potentially could give rise to increased cell adherence.

Medium was changed every 2-3 days. Cells were harvested with TrypLE (Life Technologies) when reaching a confluency of 80% for subculture or experiments. All experiments were performed at 37° C. with 5% CO2 and 95% humidity.

Example 6—Effect of Matrices on Early Attachment of Adherent Cells

A. Early Attachment Assay

Cells were harvested at passage 3-8, seeded at 20 000/cm² and allowed to adhere to the films or controls for 1 h in a cell incubator before gentle washing twice with pre-warmed phosphate buffered saline (PBS) followed by 10 min fixation with 96% ethanol. After three washings in water, cells were stained for 30 min with 0.1% Crystal Violet in $H_2O$. Plates were dried after extensive washing in water.

Attachment and morphology of cells bound to the films obtained in Example 3 were documented by taking micrographs at 2× and 10× magnification in an inverted bright field microscope. The color was then dissolved in 40 µL 20% acetic acid for 10 min, and 35 µL of the solution was transferred to a 384-well plate for optical density measurement at 595 nm (TECAN Infinite M200). Wells with cells fixed without pre-washing was used as positive control. Wells with no cells were used as blank. Experiments were run in hexaplicates and repeated three times.

Determination of cell coverage area within a defined region (9.12 mm²) of the micrographs (at 2× magnification) was done using the software NIS elements BR (Nikon).

B. Cellular Stainings

Cells were harvested at passage 3-8, seeded at 3500/cm² and allowed to adhere onto films for 20 min, 1 or 3 hours in chamber slides. After gentle washing, cells were fixed with 4% paraformaldehyde, permeabilized with 0.1% Triton X-100 in PBS, and blocked with 1% bovine serum albumin (BSA, AppliChem) in PBS.

Primary antibody were used at the following concentrations in 1% BSA: mouse anti human vinculin (Sigma V9131) at 9.5 µg/ml, mouse-anti human beta1-integrin (activated conformation, clone HUTS-4) at 3.3 µg/mL, or mouse-anti human alpha5-integrin (ligand bound conformation, clone SNAKA-51) at 2.5 µg/mL, both Millipore.

Secondary antibody was AlexaFlour488 goat anti mouse IgG (H+L), cross adsorbed (Invitrogen), used at 1:500. Phalloidin-AlexaFluor594 (Life Technologies) were used at 1:40 to detect filamentous actin. DAPI was used for nuclear staining. Slides were mounted in Fluorescence mounting medium (Dako, Copenhagen).

The stained cells were analyzed using an inverted microscope (Nikon Eclipse Ti) at 4× and 10× magnification. Excitation at 563/45 nm and detection at 625/50 nm was used for red fluorescence, whereas excitation with 387/11 nm and detection at 447/60 nm was used to monitor blue fluorescence.

For microscopic analysis of cell adhesion (formation of focal adhesions and stress fibers), a confocal microscope was used (Carl Zeiss LSM 710) at 10× and 63× magnification.

Presence of stress fibers were defined as strongly stained prominent and thick f-actin filaments, and graded from 0-4, where 0=none, 1=few-some, 2=many, 3=most, and 4=all cells exhibit stress fibers.

Presence of focal adhesions were estimated as percent of cells exhibiting focal adhesions. Quality of focal adhesions were graded from 1-4 regarding presence of small and dim focal adhesion (=1p), small and distinct focal adhesions (=2p), abundant focal adhesions (=3p) and large and bright focal adhesions (=4p), and multiplied with the portion of positive cells expressing this specific type of focal adhesions (0-4, where 0≈none of, 1≈one fourth of, 2≈half of, 3≈three fourths of, and 4≈all of the focal adhesion-positive cells.)

C. $FN_{CC}$-Silk Promotes Early Attachment of Adherent Cells

First, we wanted to investigate how well adherent cells attach and spread on the $FN_{CC}$-silk ($FN_{CC}$-4RepCT, SEQ ID NO: 13) compared to linear RGD proteins (RGD-4RepCT, SEQ ID NO: 16) and WT silk proteins (4RepCT, SEQ ID NO: 2) obtained in Example 3. Silk films of the three different variants were prepared in cell culture plates, and human primary endothelial cells (EC), mesenchymal stem cells (MSC) or keratinocytes (KC) were allowed to adhere for 1 h before fixation and staining.

Figure 3A:
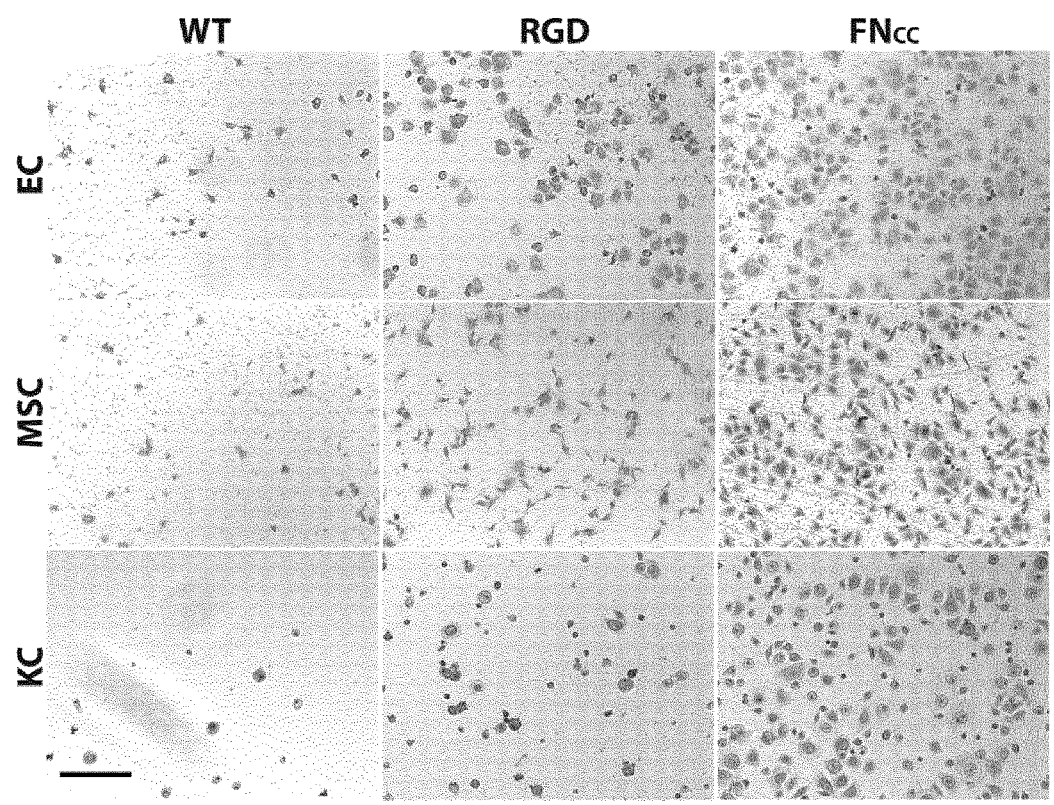
FIG. 3a and FIG. 3b show micrographs and coverage density of endothelial cells (EC), mesenchymal stem cells (MSC) and keratinocytes (KC) after 1 h adhesion to film of WT silk (SEQ ID NO: 2) or silk functionalized with RGD (SEQ ID NO: 16) or $FN_{CC}$ (SEQ ID NO: 13).

FIG. 3a shows micrographs of EC, MSC and KC after 1 h adhesion to a film of WT silk (SEQ ID NO: 2) or silk functionalized with RGD (SEQ ID NO: 16) or $FN_{CC}$ (SEQ ID NO: 13), followed by staining with crystal violet (10× magnification). Scale bar 50 µm.

Figure 3B:
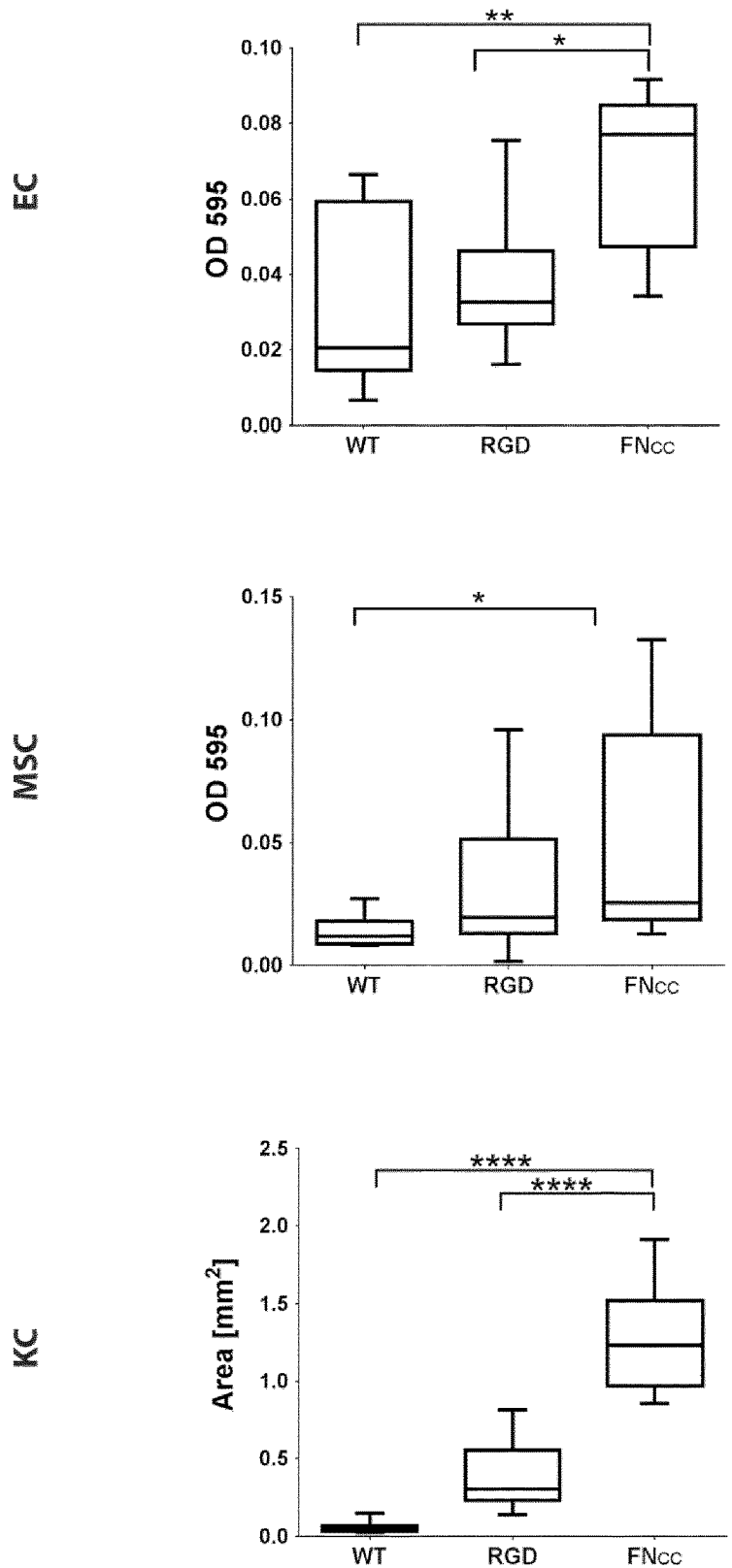

FIG. 3b shows the OD of crystal violet dissolved from cells adhered to different silk variants for EC (upper panel), and MSC (middle panel), and cell coverage area by KC (lower panel) within a defined region (9.12 mm²). EC and MSC: triplicates or duplicates, KC: quadruplicates. All cell types n=3. Seeding density 20 000/cm2. Boxplot: line=median, box: 25%-75%, whiskers=mean and max. Statistics: *P<0.05, P<0.01, **P<0.0001.

From the micrographs shown in FIG. 3a, a clear improvement of attachment is seen on the $FN_{CC}$ films compared to both RGD and WT for all three cell types. After imaging, the color trapped by the EC and MSC respectively was dissolved and OD was captured and used as a measure of the number of bound cells (FIG. 3b, upper and middle panel). For both cell types significantly more cells had bound to the $FN_{CC}$-silk after 1 h compared to WT silk (P<0.01 for EC and P<0.05 for MSC). Significantly more EC had attached to $FN_{CC}$ also compared to RGD silk (p<0.01). This colorimetric method was less suitable for KC since with this cell type, some cells also attached outside the film surface, thus contributing to the OD value although not bound to the silk film. Instead, the area of cells bound to the film was measured by image analysis at 2× magnification, as shown in FIG. 3b (lower panel). The area of KC bound to $FN_{CC}$ was significantly larger than on both WT- and RGD-silk (P<0.0001).

D. Primary KC Adhere Equally Well to $FN_{CC}$-Silk and Bovine Fibronectin

After seeing this positive effect of the introduced $FN_{CC}$ motif, we wanted to find out how well the $FN_{CC}$-silk would compare to native, full length fibronectin, where the RGD is presented on a turn loop constrained by the structure. We therefore used fibronectin from bovine plasma (BFN) to coat cell culture wells, as well as naked cell culture treated plastic (TCT), on which KC can be cultured, as a control. Serum-free experimental conditions was chosen to avoid possible interactions between the matrices and serum proteins that potentially could give rise to increased cell adherence.

Figure 4A:
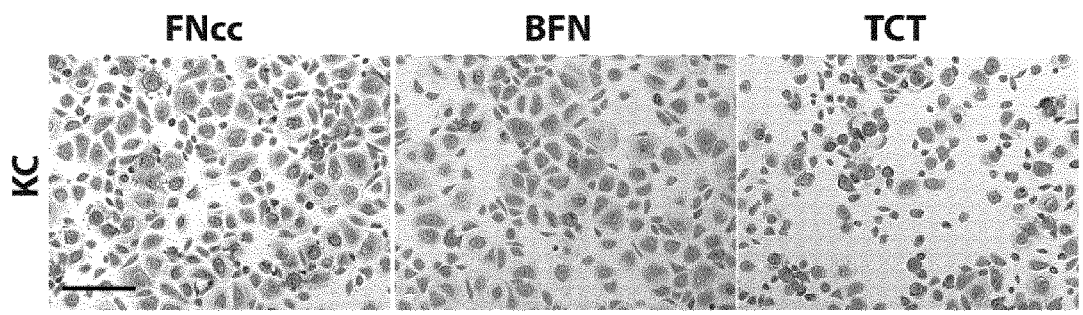
FIG. 4a and FIG. 4b show micrographs and cell coverage area of keratinocytes (KC) after 1 h adhesion to either silk functionalized with $FN_{CC}$ (SEQ ID NO: 13), a bovine fibronectin coated surface (BFN) or tissue culture treated cell plastic (TCT).
Figure 4B:
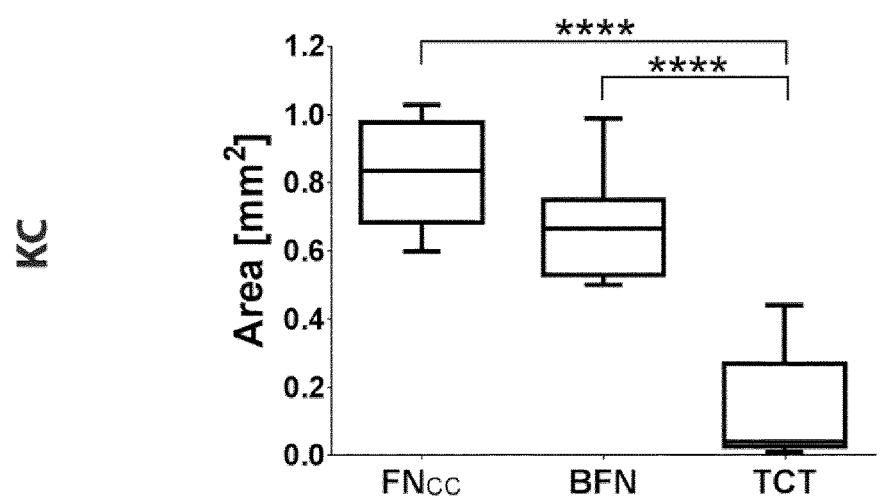

The results for KC after 1 h adhesion to either silk functionalized with $FN_{CC}$, a bovine fibronectin coated surface (BFN) or tissue culture treated cell plastic (TCT) are presented in FIG. 4. FIG. 4a shows micrographs at 10× magnification after staining with crystal violet. Seeding density 40 000/cm². Scale bar 50 µm. FIG. 4b shows cell coverage area within a defined region (9.12 mm²), (Quadruplicates, n=3). Seeding density 20 000/cm2. Boxplot: line=median, box: 25%-75%, whiskers=mean and max. Statistics (vs TCT): ****P<0.0001.

When comparing cell coverage area, it was evident that KC bound equally well to the BFN and the $FN_{CC}$-silk after 1 h adherence, and importantly both significantly better than TCT (P<0.0001) (FIG. 4).

Example 7—Impact of a Cysteine-Looped Conformation for RGD Presentation in $FN_{CC}$-Silk Encouraged by these results, we wanted to go further and look into the mechanism by which $FN_{CC}$-silk (SEQ ID NO: 13) creates an attractive surface for the cells. For this purpose, we used two FN-silk variants where a linear RGD presentation is expected (FIG. 1a). The first variant ($FN_{VS}$; SEQ ID NO: 15), contains the original sequence of the RGD-containing motif in fibronectin, to show the effect of the native flanking amino acids without influence of the loop conformation. In the second variant ($FN_{SS}$; SEQ ID NO: 14), the two flanking cysteines in $FN_{CC}$ were substituted for serine, which resembles cysteine but lacks the —SH-group and is therefore unable to form disulfide bridges. The different FN-silk variants, as well as RGD-silk (SEQ ID NO: 16) and WT-silk (SEQ ID NO: 2), were evaluated with primary KC. Cells were analyzed both for early attachment (FIG. 5), spreading and formation of stress fibers (FIG. 6), and focal adhesions (FIG. 7). Early attachment assay and cellular stainings were performed as detailed in Example 6.

A. Early Attachment

Figure 5A:
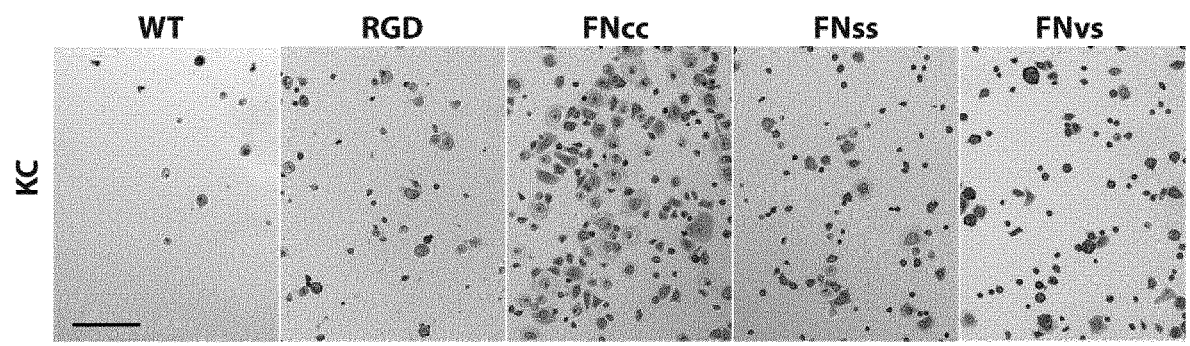
FIG. 5a and FIG. 5b show micrographs and cell coverage area of keratinocytes (KC) after 1 h adhesion to WT-silk (SEQ ID NO: 2) or silk functionalized with $FN_{CC}$ (SEQ ID NO: 13), $FN_{VS}$ (SEQ ID NO: 15), $FN_{SS}$ (SEQ ID NO: 14) or RGD (SEQ ID NO: 16).
Figure 5B:
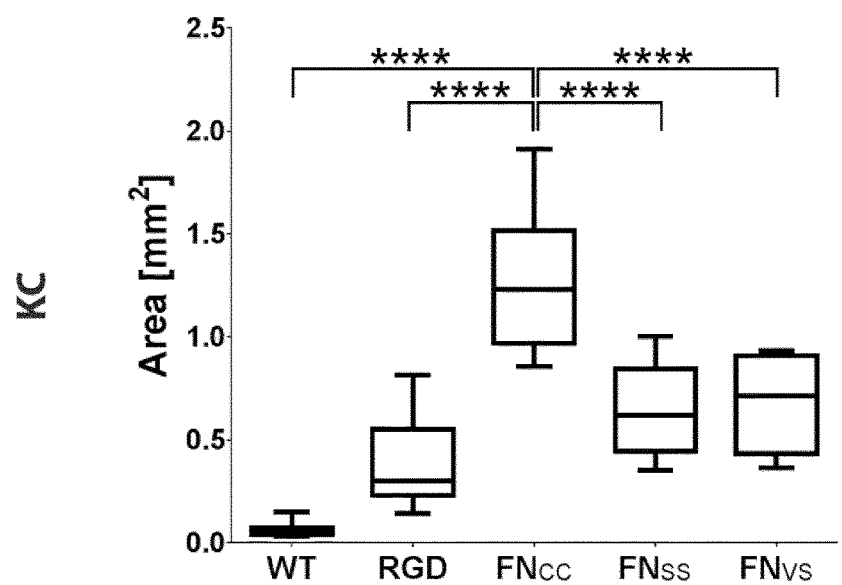

The results for KC after 1 h adhesion to films of WT-silk (SEQ ID NO: 2) or silk functionalized with $FN_{CC}$ (SEQ ID NO: 13), $FN_{VS}$ (SEQ ID NO: 15), $FN_{SS}$ (SEQ ID NO: 14) or RGD (SEQ ID NO: 16) are presented in FIG. 5. FIG. 5a shows micrographs at 10× magnification after staining with crystal violet. Seeding density 20 000/cm². FIG. 5b shows cell coverage area within a defined region (9.12 mm²), (Quadruplicates, n=3). Boxplot: line=median, box: 25%-75%, whiskers=mean and max. Statistics: ****P<0.0001.

In initial experiments, KC were allowed to adhere for 1 h onto films of WT, RGD- and FN-silk variants, and stained with crystal violet for detection and morphology (FIG. 5a). When pooling data from image analysis of 3 experiments (hexaplicates), $FN_{CC}$-silk showed increased attachment (i.e. area covered by cells) compared to both $FN_{SS}$ and $FN_{VS}$ (P<0.0001, FIG. 5b). $FN_{CC}$-silk also gave significantly higher adhesion of KC compared to RGD-silk (P<0.0001). All FN-silk variants showed significantly increased adhesion compared to WT-silk (P<0.0001).

Moreover, pooled data from 8 experiments, where the crystal violet was dissolved from the cells and the OD thereof measured in a plate reader, showed very similar results (FNCC versus FN-controls, P<0.0001), despite that cells in these experiments to some degree also adhered to the cell plastic outside the silk-films (data not shown).

B. Cell Spreading and Formation of Stress-Fibers

Figure 6:
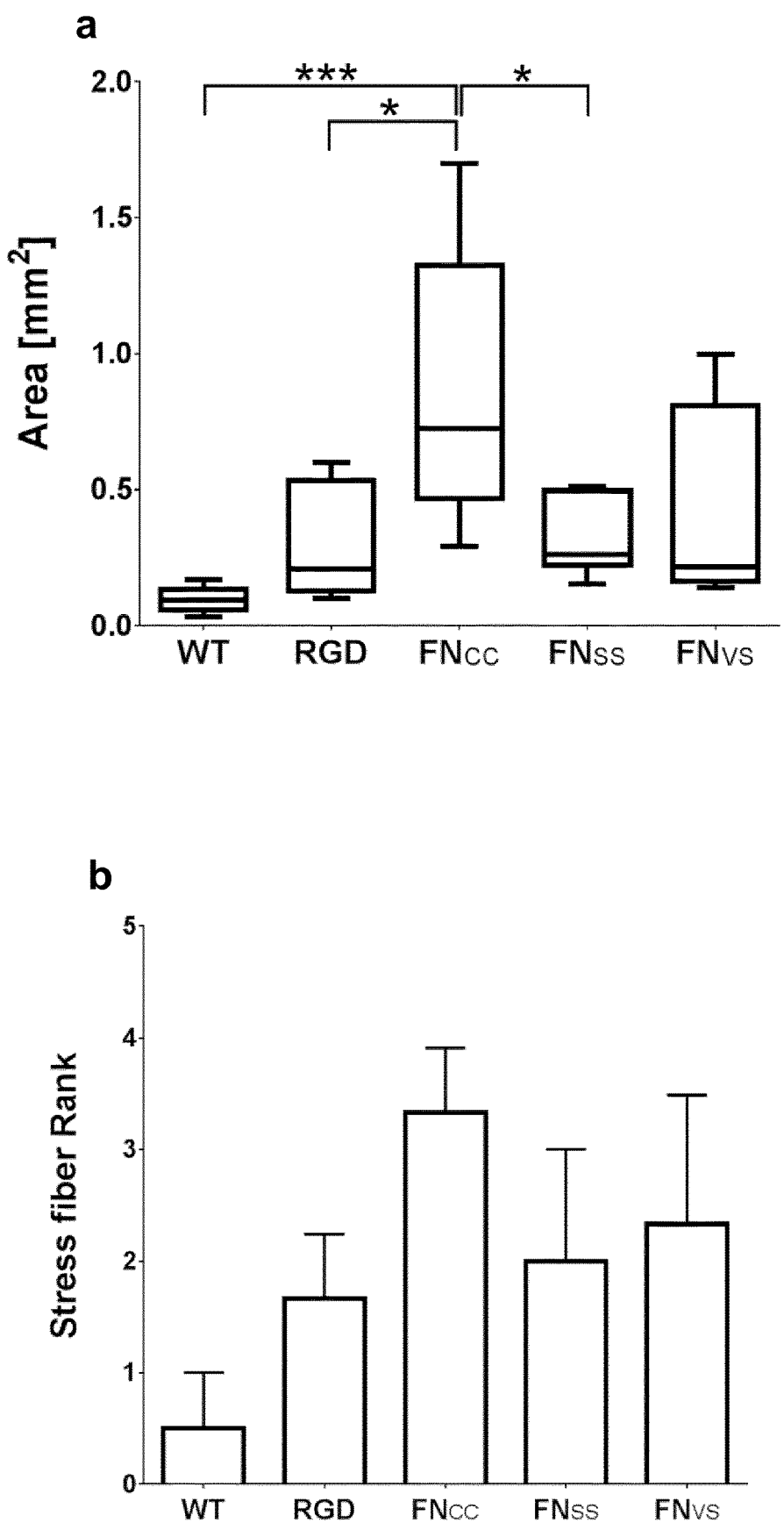
FIG. 6 shows cell coverage area and stress fiber ranking of keratinocytes (KC) after 3 h adhesion to WT-silk (SEQ ID NO: 2) or silk functionalized with $FN_{CC}$ (SEQ ID NO: 13), $FN_{VS}$ (SEQ ID NO: 15), $FN_{SS}$ (SEQ ID NO: 14) or RGD (SEQ ID NO: 16).
Figure 7:
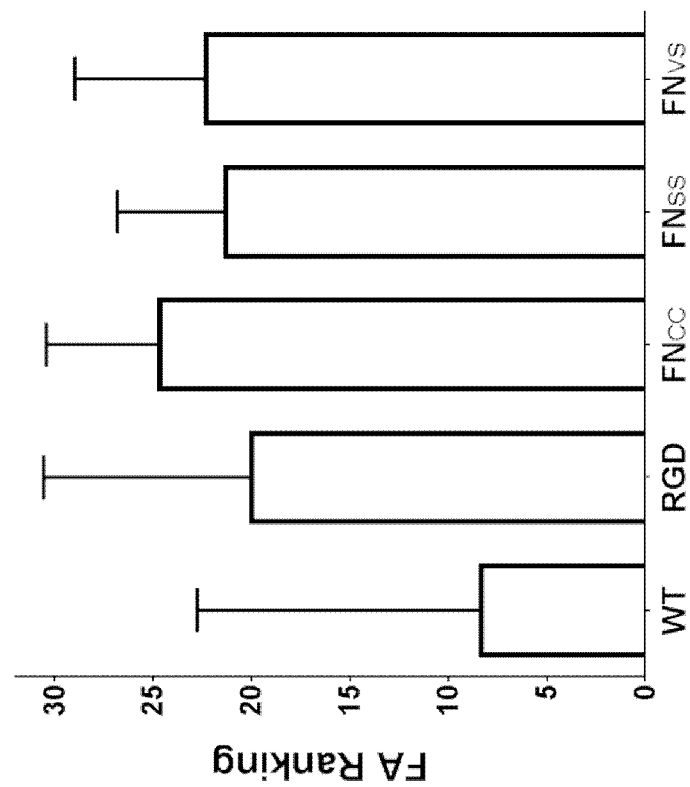
FIG. 7 shows graphs of formation of focal adhesions in keratinocytes after adherence for 3 h onto films of WT-silk (SEQ ID NO: 2) or silk functionalized with $FN_{CC}$ (SEQ ID NO: 13), $FN_{VS}$ (SEQ ID NO: 15), $FN_{SS}$ (SEQ ID NO: 14) or RGD (SEQ ID NO: 16).
Figure 7:
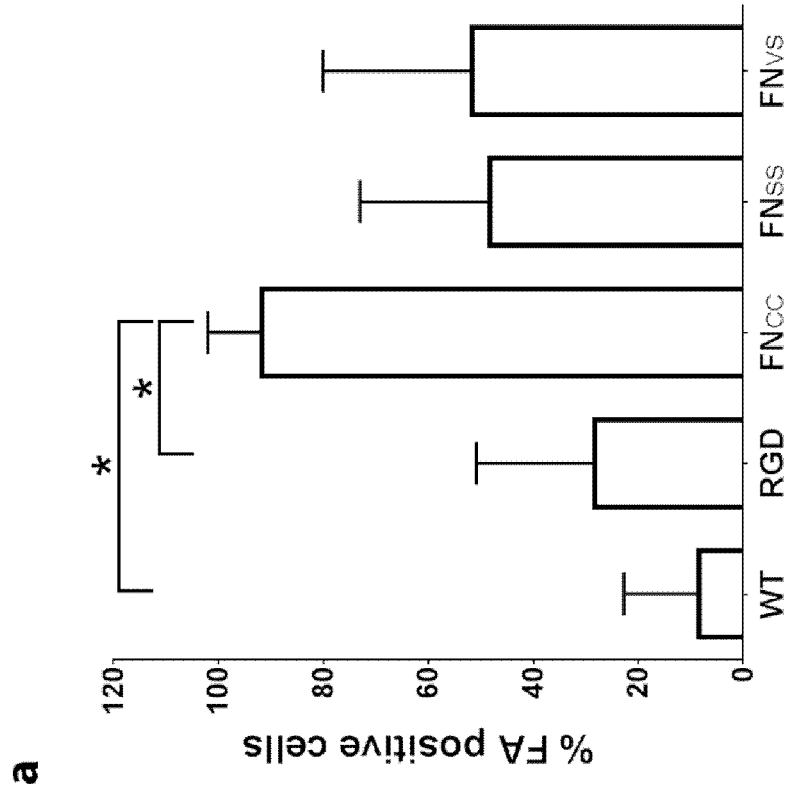

The results for KC after 3 h adhesion to films of WT-silk (SEQ ID NO: 2) or silk functionalized with $FN_{CC}$ (SEQ ID NO: 13), $FN_{VS}$ (SEQ ID NO: 15), $FN_{SS}$ (SEQ ID NO: 14) or RGD (SEQ ID NO: 16) are presented in FIG. 6. FIG. 6a shows cell coverage area, duplicates, n=4. Boxplot: line=median, box: 25%-75%, whiskers=mean and max. FIG. 6b shows stress fiber ranking (mean and standard deviation, single wells, n=3). Seeding density 3 500/cm². Statistics: ***P<0.001, *P<0.05.

By staining for F-actin, cell spreading and formation of stress fibers in KC after 3 h adhesion were investigated (FIG. 6). The results show that $FN_{CC}$ film, but not $FN_{SS}$ or $FN_{VS}$ films, gave a significantly increased spreading of KC compared to RGD-film (p<0.05) and WT-film (p<0.001), when measuring total cell area in 4× micrographs (n=4, duplicates), (FIG. 6a). The spreading of KC on $FN_{CC}$-silk was also significantly increased compared to $FN_{SS}$-silk (p<0.05). The KC on RGD, $FN_{SS}$- and $FN_{VS}$-silk showed a higher proportion of cells with a rounded appearance, whereas on $FN_{CC}$-silk most cells had a nice spread-out morphology with distinct actin filaments.

KC stained for F-actin were also analyzed for the presence of stress fibers, as an indicator of established attachment (FIG. 6b). Presence of stress fibers was defined as thick and brightly stained actin filaments (bundles), and the analysis was done by inspection at 63× magnification (n=3). This analysis showed similar results as the area measurement, but no statistically significant differences were found.

C. Formation of Focal Adhesions

Formation of focal adhesions within the cells was analyzed after 3 h by staining for F-actin in combination with vinculin, which is one of the major components of the focal adhesion complex. Co-staining of F-actin and vinculin is thus a sign of integrin-involved, well established binding of cells to the underlying substrate. Focal adhesions appear as yellow-greenish elongations of the F-actin filaments, often situated close to the cell membrane.

The results from the analysis of formation and characterization of focal adhesions in KC after adherence for 3 h onto films of WT-silk (SEQ ID NO: 2) or silk functionalized with $FN_{CC}$ (SEQ ID NO: 13), $FN_{VS}$ (SEQ ID NO: 15), $FN_{SS}$ (SEQ ID NO: 14) or RGD (SEQ ID NO: 16) is presented in FIG. 7. Slides were scanned with a confocal microscope at 10× for overview (FIG. 7a) and at 63× for details (FIG. 7b). Two types of grading of the focal adhesions in the cells were performed.

Firstly, the percentage of cells exhibiting focal adhesions was assessed by visual examination of the entire film in each well at 10× magnification. Pooled data from three experiments showed a significant increase in percentage of cells expressing focal adhesions on $FN_{CC}$-silk, compared to RGD and WT (p<0.05), (FIG. 7a). FIG. 7a is a graph showing percentage of cells exhibiting focal adhesions (mean and standard deviation). Experiments were run in duplicates, n=3. Statistics: *P<0.05. Secondly, since not only the abundance of cells exhibiting focal adhesions, but also the characteristics of the focal adhesions seen in the cells appeared to differ between the different silk variants, we decided to examine this further. The appearance of the focal adhesions within each positive cell was therefore evaluated according to a grading system. Briefly, grading spanned from small and dim, appearing sparsely within the cell ("subtle"), to large and bright, appearing abundantly within the cell ("prominent"). In this way we could judge the quality of the focal adhesions independently of how many of the cells on the film that exhibited these structures. The outcome of this analysis showed a tendency of more prominent focal adhesions in cells attached to $FN_{CC}$-silk compared to the other silk types. FIG. 7b is a graph showing grading of the focal adhesions, independently of total number of positive cells found, (mean and standard deviation). Grading was done in single wells, n=3.

The results show that the variation of focal adhesion quality is larger in cells on RGD, $FN_{SS}$ and $FN_{VS}$ than on $FN_{CC}$-silk, reflecting the presence of both prominent and subtle focal adhesions in cells on $FN_{SS}$ and $FN_{VS}$, but almost only prominent focal adhesions on $FN_{CC}$-silk. Interestingly, such prominent focal adhesions appeared as early as 20 minutes after seeding onto $FN_{CC}$.

In each individual experiment, $FN_{CC}$-silk, without exception, gave the most efficient adhesion of the tested films. In contrast, the attachment onto $FN_{SS}$- and $FN_{VS}$-silk varied from being similar to RGD-silk to being only somewhat lower than on $FN_{CC}$-silk.

With the aim to further elucidate the role of the cysteine linked loop for presentation of the RGD motif, we performed experiments where reducing agents were added to the $FN_{CC}$-silk solution directly before films were casted. The idea was to prevent disulphide formation in these films, generating a linear, non-looped motif. However, no differences compared to non-reduced $FN_{CC}$ film were detected. When considering that the films are completely dried during the production process, one can assume that the reducing agent, in the lack of buffer, can no longer prevent disulfide formation to occur. We therefore consider $FN_{SS}$ the most proper non-looped control accomplishable.

Example 8—Engagement of Integrin α5β1 in KC Adhering to $FN_{CC}$-Silk

Since the integrin α5β1 is known to selectively bind to fibronectin, we decided to investigate if this integrin is involved in the binding of KC to $FN_{CC}$-silk (SEQ ID NO: 13). To do this, we selected two monoclonal antibodies, developed to specifically recognize the ligand bound conformation of α5 integrin (SNAKA-51) and the activated conformation of β1 integrin (HUTS-4), respectively, and used them in combination for staining of KC adhering to $FN_{CC}$-silk for 3 h, in combination with staining with phalloidin for F-actin, as set out in Examples 6-7. Analysis of the cells revealed a week but distinct staining pattern resembling the pattern seen when staining for vinculin.

Example 9—Applications of $FN_{CC}$-Silk

Intrigued by the findings of such excellent binding properties of $FN_{CC}$-silk regarding early attachment of adherent cells, we performed a few pilot studies to get a picture of its ability to support various cell culture applications. Firstly, we wanted to evaluate the effect of the $FN_{CC}$ motif on cell proliferation.

A. Cell Viability Analysis with Alamar Blue

Figure 8:
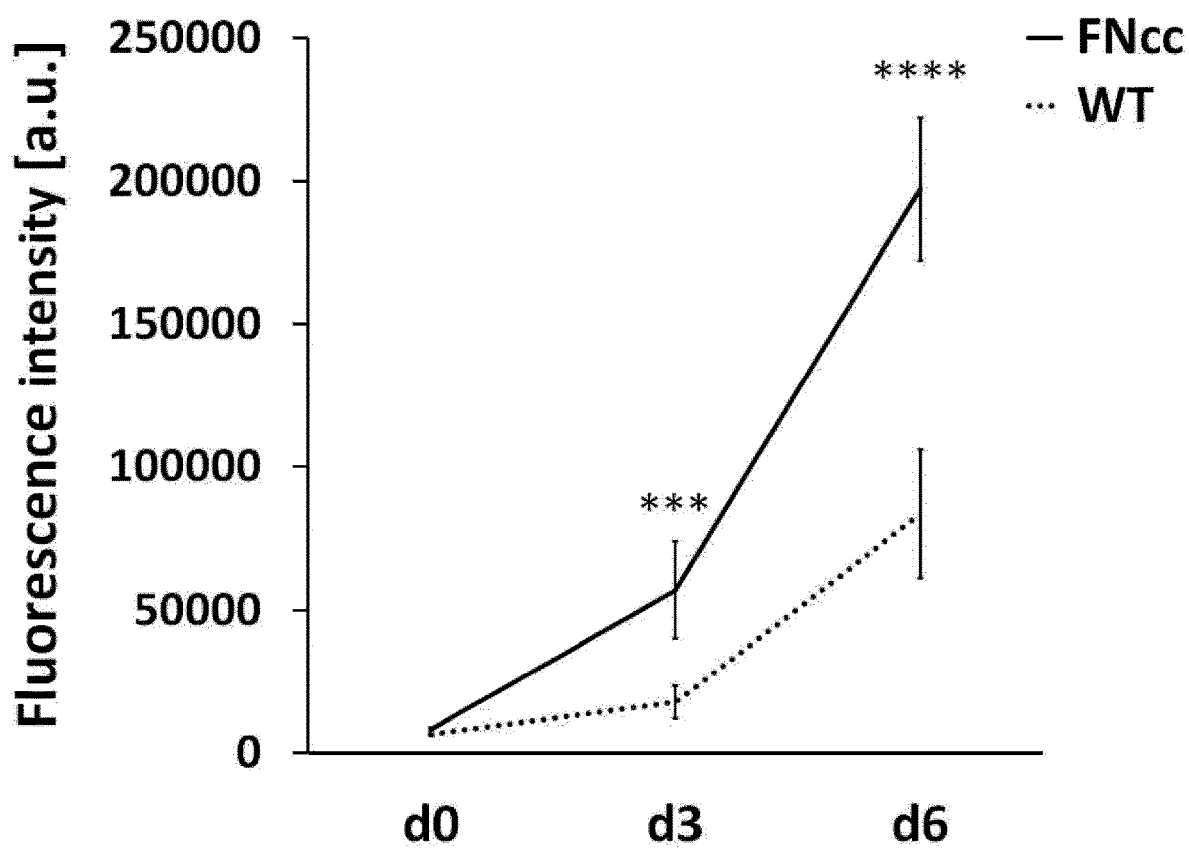
FIG. 8 shows a graph of an Alamar blue viability assay of keratinocytes seeded on films of WT-silk (SEQ ID NO: 2) or $FN_{CC}$ silk (SEQ ID NO: 13).

Cell growth of primary keratinocytes (NHEK) after initial low seeding density 3 500 cells/cm² on wells coated with films of WT-silk (SEQ ID NO: 2) or $FN_{CC}$-silk (SEQ ID NO: 13) in 96-well plates was monitored with Alamar Blue cell viability assay (Molecular Probes) every third day during the culture period. After 4 h incubation with Alamar blue (diluted 1:10 in cell culture medium), fluorescence intensity of 90 μL supernatants from the cultures was measured with a fluorescence plate reader (CLARIOstar, BMG Labtech) using excitation at 544 nm and emission at 595 nm. Two independent experiments were performed where films were analysed in hexaplicates. Fluorescence intensities, correlating the number of living cells in each well, were plotted over time to yield growth profiles of cells seeded on silk with different cell binding motifs. The results presented in FIG. 8 show an increased level of viable cells on $FN_{CC}$-silk compared to WT-silk (P<0.001 day 3 and P<0.0001 day 6; **P<0.0001, *P<0.001), indicating an improved ability to support cell proliferation conveyed by the $FN_{CC}$ motif.

B. Repopulation Assay

To evaluate the ability of the different silk variants to support repopulation of an open would field, dermal keratinocytes (NHEK) were stained with Oregon green cell trace (Life Technologies) before seeded onto films of $FN_{CC}$-silk (SEQ ID NO: 13) and WT-silk (SEQ ID NO: 2) at 20 000 cells/cm² in 24 well plates. Wound field inserts (CytoSelect™ Wound healing assay, Cell Biolabs) were added into the wells before cell seeding to generate a 0.9 mm wide open would field in the cell monolayer, while keeping the film intact. After 16 h the inserts were removed, and the repopulation process were followed each day and documented by inverted fluorescence microscopy at day 0 (insert removal), day 2 and 4. At day 6 cells were fixed and stained according to the assay protocol, and imaged by inverted bright field microscopy.

Thus, green-traced cells were seeded at high density into wells with inserts preventing cells to reach a defined part of the silk-film, the "wound field". After monolayer formation outside the wound field, the insert was removed, and repopulation of the gap was documented during 6 days of culture, thus allowing both migration and proliferation of cells. Keratinocytes efficiently repopulated the wound field on $FN_{CC}$-silk, which was almost completely covered with cells at the end of the experiment.

C. Transferable Cell Monolayers

NHEK were harvested and traced with AMCA orange cell tracker (Life Technologies) before seeded onto free-standing films of $FN_{CC}$-silk silk (SEQ ID NO: 13) mounted on metal frames at 20 000 cells/cm2. The formed monolayer was documented by inverted fluorescence microscopy.

Primary keratinocytes seeded onto such free-standing films formed a monolayer that could easily be transferred between culture wells.

Example 10—Cell Adherence to Surfaces with Immobilized Peptides

A silicon (SiO) surface is activated using an organosilane (e.g. 3-aminopropyltriethoxysilane APTES) to thereafter immobilize aminoreactive peptides (via their N-terminus) using e.g. EDC/NHS chemistry.

The peptides used for immobilization are designed with a glycine spacer, as follows:

1. GGGGGCTG<u>RGD</u>SPAC (SEQ ID NO: 21)

2. GGGGGVTG<u>RGD</u>SPAS (SEQ ID NO: 22)

3. GGGGGSTG<u>RGD</u>SPAS (SEQ ID NO: 23)

4. GGGGGCDW<u>RGD</u>NQFC (SEQ ID NO: 24)

Early attachment to the surfaces with immobilized peptides is analyzed using human keratinocytes (HaCAT) seeded at 20 000/cm². The cells are then allowed to adhere for 1 h in a cell incubator before gentle washing twice with pre-warmed phosphate buffered saline (PBS) followed by 10 min fixation with 96% ethanol. After three washings in water, cells are stained for 30 min with 0.1% Crystal Violet in $H_2O$.

Attachment and morphology of cells are documented by taking micrographs at 2× and 10× magnification in an inverted bright field microscope. The Crystal violet color is then dissolved in 40 µL 20% acetic acid for 10 min, and 35 µL of the solution is transferred to a 384-well plate for optical density measurement at 595 nm (TECAN Infinite M200). Cells fixed without pre-washing are used as positive control (reference).

Example 11—Cell Culture on $FN_{CC}$ Silk Matrices

After purification, solutions of $FN_{CC}$-silk protein (SEQ ID NO: 13) were used to coat cell culture plates (Sarstedt, hydrophobic plates for suspension cells). Briefly, the protein solutions were diluted to 0.1 mg/ml in Tris buffer, and allowed to incubate at room temperature for 30 minutes before removal and wash.

Cells were harvested using trypsination (TrpLE) and seeded onto the FNcc-silk coatings at suitable cell density (3-10 000 cells/cm2). Cell growth was monitored with Alamar Blue cell viability assay (Molecular Probes) regularly (every 2-3 day). At the end point, after 7-14 days, Live/dead staining was performed. The following cell types showed positive growth profile and a majority (>80%) of viable cells at the end point:

Human Skeletal Muscle Satellite Cells
Human Dermal Microvascular Endothelial Cells
Human Mesenchymal stem cells
Mouse Mesenchymal stem cells
Human Dermal fibroblasts
HaCaT Keratinocytes
MIN6-m9 pancreatic cell line.

The invention claimed is:

1. An immobilized protein or an immobilized peptide comprising:
    a cell-binding motif with selectivity for integrins, wherein the cell-binding motif comprises an amino acid sequence as follows:

wherein
    each of $X^1$, $X^2$, $X^3$, $X^4$ and $X^5$ are amino acid residues independently selected from the group consisting of: G, A, V, S, T, D, E, M, P, N and Q; and
    $C^1$ and $C^2$ are connected via a disulphide bond.

2. The immobilized protein or the immobilized peptide according to claim 1, wherein
    each of $X^1$ and $X^3$ are amino acid residues independently selected from the group consisting of: G, S, T, M, N and Q; and
    each of $X^2$, $X^4$ and $X^5$ are amino acid residues independently selected from the group consisting of: G, A, V, S, T, P, N and Q.

3. The immobilized protein or the immobilized peptide according to claim 2, wherein
    $X^1$ is selected from the group consisting of: G, S, T, N and Q;
    $X^3$ is selected from the group consisting of: S, T and Q; and
    each of $X^2$, $X^4$ and $X^5$ are amino acid residues independently selected from the group consisting of: G, A, V, S, T, P and N.

4. The immobilized protein or the immobilized peptide according to claim 3, wherein,
    $X^1$ is S or T;
    $X^2$ is G, A or V;
    $X^3$ is S or T;
    $X^4$ is G, A, V or P; and
    $X^5$ is G, A or V.

5. The immobilized protein or the immobilized peptide according to claim 1, wherein $X^2$ is G or A.

6. The immobilized protein or the immobilized peptide according to claim 2, wherein $X^2$ is G.

7. The immobilized protein or the immobilized peptide according to claim 1, wherein $X^3$ is S.

8. The immobilized protein or the immobilized peptide according to claim 1, wherein $X^4$ is G or P.

9. The immobilized protein or the immobilized peptide according to claim 8, wherein $X^4$ is P.

10. The immobilized protein or the immobilized peptide according to claim 1, wherein $X^5$ is G or A.

11. The immobilized protein or the immobilized peptide according to claim 10, wherein $X^5$ is A.

12. The immobilized protein or the immobilized peptide according to claim 1 wherein the cell-binding motif comprises the amino acid sequence CTGRGDSPAC (SEQ ID NO: 10).

13. The immobilized protein or the immobilized peptide according to claim 1, wherein the cell-binding motif has selectivity for α5β1 integrins.

14. A cell scaffold material comprising:
    a protein polymer which comprises the immobilized protein according to claim 1 as a repeating unit.

15. The cell scaffold material according to claim 14, wherein the protein polymer is in a physical form selected from the group consisting of film, coating, foam, fiber and fiber-mesh.

16. The cell scaffold material according to claim 14, wherein the protein polymer is in a physical form of a free-standing matrix.

17. A method for the cultivation of cells, comprising the steps of:
    providing a sample of cells;
    applying the sample to a cell scaffold material; and
    maintaining the cell scaffold material having the cells applied thereto under conditions suitable for cell culture,
    wherein the cell scaffold material comprises a protein polymer, which comprises the immobilized protein according to claim 1 as a repeating structural unit.

18. The method according to claim 17, wherein the cells display α5β1 integrins on their cell surface, and wherein the cell-binding motif of the immobilized protein has selectivity for α5β1 integrins.

19. The method according to claim 17, wherein the cells are selected from the group consisting of skeletal muscle cells, endothelial cells, stem cells, fibroblasts, keratinocytes and cell lines.

* * * * *

SEQUENCE LISTING

```
<160> NUMBER OF SEQ ID NOS: 60

<210> SEQ ID NO 1
<211> LENGTH: 789
<212> TYPE: DNA
<213> ORGANISM: Euprosthenops australis

<400> SEQUENCE: 1
ggtccgaatt caggtcaagg aggatatggt ggactaggtc aaggagggta tggacaaggt    60
gcaggaagtt ctgcagccgc tgccgccgcc gcagcagccg ccgcagcagg tggacaaggt   120
ggacaaggtc aaggaggata tggacaaggt tcaggaggtt ctgcagccgc cgccgccgcc   180
gcagcagcag cagcagctgc agcagctgga cgaggtcaag gaggatatgg ccaaggttct   240
ggaggtaatg ctgctgccgc agccgctgcc gccgccgccg ccgctgcagc agccggacag   300
ggaggtcaag gtggatatgg tagacaaagc caaggtgctg gttccgctgc tgctgctgct   360
gctgctgctg ccgctgctgc tgctgcagga tctggacaag gtggatacgg tggacaaggt   420
caaggaggtt atggtcagag tagtgcttct gcttcagctg ctgcgtcagc tgctagtact   480
gtagctaatt cggtgagtcg cctctcatcg ccttccgcag tatctcgagt ttcttcagca   540
gtttctagct tggtttcaaa tggtcaagtg aatatggcag cgttacctaa tatcatttcc   600
aacatttctt cttctgtcag tgcatctgct cctggtgctt ctggatgtga ggtcatagtg   660
caagctctac tcgaagtcat cactgctctt gttcaaatcg ttagttcttc tagtgttgga   720
tatattaatc catctgctgt gaaccaaatt actaatgttg ttgctaatgc catggctcaa   780
gtaatgggc                                                           789

<210> SEQ ID NO 2
<211> LENGTH: 263
<212> TYPE: PRT
<213> ORGANISM: Euprosthenops australis
<220> FEATURE:
```

```
<221> NAME/KEY: DOMAIN
<222> LOCATION: (1)..(158)
<223> OTHER INFORMATION: REP fragment
<220> FEATURE:
<221> NAME/KEY: DOMAIN
<222> LOCATION: (159)..(165)
<223> OTHER INFORMATION: Spacer fragment
<220> FEATURE:
<221> NAME/KEY: DOMAIN
<222> LOCATION: (166)..(263)
<223> OTHER INFORMATION: CT fragment

<400> SEQUENCE: 2

Gly Pro Asn Ser Gly Gln Gly Tyr Gly Gly Leu Gly Gln Gly Gly
1               5                   10                  15

Tyr Gly Gln Gly Ala Gly Ser Ser Ala Ala Ala Ala Ala Ala Ala
                20                  25                  30

Ala Ala Ala Ala Gly Gly Gln Gly Gly Gln Gly Gln Gly Tyr Gly
            35                  40                  45

Gln Gly Ser Gly Gly Ser Ala Ala Ala Ala Ala Ala Ala Ala Ala
    50                  55                  60

Ala Ala Ala Ala Ala Gly Arg Gly Gln Gly Gly Tyr Gly Gln Gly Ser
65                  70                  75                  80

Gly Gly Asn Ala Ala Ala Ala Ala Ala Ala Ala Ala Ala Ala Ala
                85                  90                  95

Ala Ala Gly Gln Gly Gly Gln Gly Gly Tyr Gly Arg Gln Ser Gln Gly
                100                 105                 110

Ala Gly Ser Ala Ala Ala Ala Ala Ala Ala Ala Ala Ala Ala Ala
            115                 120                 125

Ala Gly Ser Gly Gln Gly Gly Tyr Gly Gly Gln Gly Gln Gly Gly Tyr
        130                 135                 140

Gly Gln Ser Ser Ala Ser Ala Ser Ala Ala Ser Ala Ala Ser Thr
145                 150                 155                 160

Val Ala Asn Ser Val Ser Arg Leu Ser Ser Pro Ser Ala Val Ser Arg
                165                 170                 175

Val Ser Ser Ala Val Ser Ser Leu Val Ser Asn Gly Gln Val Asn Met
            180                 185                 190

Ala Ala Leu Pro Asn Ile Ile Ser Asn Ile Ser Ser Val Ser Ala
            195                 200                 205

Ser Ala Pro Gly Ala Ser Gly Cys Glu Val Ile Val Gln Ala Leu Leu
    210                 215                 220

Glu Val Ile Thr Ala Leu Val Gln Ile Val Ser Ser Ser Ser Val Gly
225                 230                 235                 240

Tyr Ile Asn Pro Ser Ala Val Asn Gln Ile Thr Asn Val Val Ala Asn
                245                 250                 255

Ala Met Ala Gln Val Met Gly
            260

<210> SEQ ID NO 3
<211> LENGTH: 98
<212> TYPE: PRT
<213> ORGANISM: Euprosthenops australis

<400> SEQUENCE: 3

Ser Arg Leu Ser Ser Pro Ser Ala Val Ser Arg Val Ser Ser Ala Val
1               5                   10                  15

Ser Ser Leu Val Ser Asn Gly Gln Val Asn Met Ala Ala Leu Pro Asn
            20                  25                  30
```

-continued

```
Ile Ile Ser Asn Ile Ser Ser Val Ser Ala Ser Ala Pro Gly Ala
            35                  40                  45

Ser Gly Cys Glu Val Ile Val Gln Ala Leu Leu Glu Val Ile Thr Ala
 50                  55                  60

Leu Val Gln Ile Val Ser Ser Ser Val Gly Tyr Ile Asn Pro Ser
 65                  70                  75                  80

Ala Val Asn Gln Ile Thr Asn Val Val Ala Asn Ala Met Ala Gln Val
                 85                  90                  95

Met Gly

<210> SEQ ID NO 4
<211> LENGTH: 100
<212> TYPE: PRT
<213> ORGANISM: Artificial Sequence
<220> FEATURE:
<223> OTHER INFORMATION: Consensus sequence derived from known MaSp1 and
      MaSp2 proteins
<220> FEATURE:
<221> NAME/KEY: MISC_FEATURE
<222> LOCATION: (1)..(71)
<223> OTHER INFORMATION: Sequence length present in known species
      variants
<220> FEATURE:
<221> NAME/KEY: VARIANT
<222> LOCATION: (7)..(7)
<223> OTHER INFORMATION: Glu

<400> SEQUENCE: 4

Ser Arg Leu Ser Ser Pro Gln Ala Ser Ser Arg Val Ser Ala Val
 1               5                  10                  15

Ser Asn Leu Val Ser Ser Gly Pro Thr Asn Ser Ala Ala Leu Ser Asn
                 20                  25                  30

Thr Ile Ser Asn Val Val Ser Gln Ile Ser Ala Ser Asn Pro Gly Leu
            35                  40                  45

Ser Gly Cys Asp Val Leu Val Gln Ala Leu Leu Glu Val Val Ser Ala
 50                  55                  60

Leu Val His Ile Leu Gly Ser Ser Ile Gly Gln Val Asn Tyr Gly
 65                  70                  75                  80

Ser Ala Gly Gln Ala Thr Gln Ile Val Gly Gln Ser Val Ala Gln Ala
                 85                  90                  95

Leu Gly Glu Phe
            100

<210> SEQ ID NO 5
<211> LENGTH: 1110
<212> TYPE: PRT
<213> ORGANISM: Euprosthenops australis
<220> FEATURE:
<221> NAME/KEY: REPEAT
<222> LOCATION: (7)..(19)
<220> FEATURE:
<221> NAME/KEY: REPEAT
<222> LOCATION: (20)..(42)
<220> FEATURE:
<221> NAME/KEY: REPEAT
<222> LOCATION: (43)..(56)
<220> FEATURE:
<221> NAME/KEY: REPEAT
<222> LOCATION: (57)..(70)
<220> FEATURE:
<221> NAME/KEY: REPEAT
<222> LOCATION: (71)..(83)
<220> FEATURE:
<221> NAME/KEY: REPEAT
<222> LOCATION: (84)..(106)
<220> FEATURE:
```

```
<221> NAME/KEY: REPEAT
<222> LOCATION: (107)..(120)
<220> FEATURE:
<221> NAME/KEY: REPEAT
<222> LOCATION: (121)..(134)
<220> FEATURE:
<221> NAME/KEY: REPEAT
<222> LOCATION: (135)..(147)
<220> FEATURE:
<221> NAME/KEY: REPEAT
<222> LOCATION: (148)..(170)
<220> FEATURE:
<221> NAME/KEY: REPEAT
<222> LOCATION: (171)..(183)
<220> FEATURE:
<221> NAME/KEY: REPEAT
<222> LOCATION: (184)..(197)
<220> FEATURE:
<221> NAME/KEY: REPEAT
<222> LOCATION: (198)..(211)
<220> FEATURE:
<221> NAME/KEY: REPEAT
<222> LOCATION: (212)..(234)
<220> FEATURE:
<221> NAME/KEY: REPEAT
<222> LOCATION: (235)..(248)
<220> FEATURE:
<221> NAME/KEY: REPEAT
<222> LOCATION: (249)..(265)
<220> FEATURE:
<221> NAME/KEY: REPEAT
<222> LOCATION: (266)..(279)
<220> FEATURE:
<221> NAME/KEY: REPEAT
<222> LOCATION: (280)..(293)
<220> FEATURE:
<221> NAME/KEY: REPEAT
<222> LOCATION: (294)..(306)
<220> FEATURE:
<221> NAME/KEY: REPEAT
<222> LOCATION: (307)..(329)
<220> FEATURE:
<221> NAME/KEY: REPEAT
<222> LOCATION: (330)..(342)
<220> FEATURE:
<221> NAME/KEY: REPEAT
<222> LOCATION: (343)..(356)
<220> FEATURE:
<221> NAME/KEY: REPEAT
<222> LOCATION: (357)..(370)
<220> FEATURE:
<221> NAME/KEY: REPEAT
<222> LOCATION: (371)..(393)
<220> FEATURE:
<221> NAME/KEY: REPEAT
<222> LOCATION: (394)..(406)
<220> FEATURE:
<221> NAME/KEY: REPEAT
<222> LOCATION: (407)..(420)
<220> FEATURE:
<221> NAME/KEY: REPEAT
<222> LOCATION: (421)..(434)
<220> FEATURE:
<221> NAME/KEY: REPEAT
<222> LOCATION: (435)..(457)
<220> FEATURE:
<221> NAME/KEY: REPEAT
<222> LOCATION: (458)..(470)
<220> FEATURE:
<221> NAME/KEY: REPEAT
<222> LOCATION: (471)..(488)
<220> FEATURE:
<221> NAME/KEY: REPEAT
<222> LOCATION: (489)..(502)
<220> FEATURE:
<221> NAME/KEY: REPEAT
<222> LOCATION: (503)..(516)
<220> FEATURE:
<221> NAME/KEY: REPEAT
```

-continued

```
<222> LOCATION: (517)..(529)
<220> FEATURE:
<221> NAME/KEY: REPEAT
<222> LOCATION: (530)..(552)
<220> FEATURE:
<221> NAME/KEY: REPEAT
<222> LOCATION: (553)..(566)
<220> FEATURE:
<221> NAME/KEY: REPEAT
<222> LOCATION: (567)..(580)
<220> FEATURE:
<221> NAME/KEY: REPEAT
<222> LOCATION: (581)..(594)
<220> FEATURE:
<221> NAME/KEY: REPEAT
<222> LOCATION: (595)..(617)
<220> FEATURE:
<221> NAME/KEY: REPEAT
<222> LOCATION: (618)..(630)
<220> FEATURE:
<221> NAME/KEY: REPEAT
<222> LOCATION: (631)..(647)
<220> FEATURE:
<221> NAME/KEY: REPEAT
<222> LOCATION: (648)..(661)
<220> FEATURE:
<221> NAME/KEY: REPEAT
<222> LOCATION: (662)..(675)
<220> FEATURE:
<221> NAME/KEY: REPEAT
<222> LOCATION: (676)..(688)
<220> FEATURE:
<221> NAME/KEY: REPEAT
<222> LOCATION: (689)..(711)
<220> FEATURE:
<221> NAME/KEY: REPEAT
<222> LOCATION: (712)..(725)
<220> FEATURE:
<221> NAME/KEY: REPEAT
<222> LOCATION: (726)..(739)
<220> FEATURE:
<221> NAME/KEY: REPEAT
<222> LOCATION: (740)..(752)
<220> FEATURE:
<221> NAME/KEY: REPEAT
<222> LOCATION: (753)..(775)
<220> FEATURE:
<221> NAME/KEY: REPEAT
<222> LOCATION: (776)..(789)
<220> FEATURE:
<221> NAME/KEY: REPEAT
<222> LOCATION: (790)..(803)
<220> FEATURE:
<221> NAME/KEY: REPEAT
<222> LOCATION: (804)..(816)
<220> FEATURE:
<221> NAME/KEY: REPEAT
<222> LOCATION: (817)..(839)
<220> FEATURE:
<221> NAME/KEY: REPEAT
<222> LOCATION: (840)..(853)
<220> FEATURE:
<221> NAME/KEY: REPEAT
<222> LOCATION: (854)..(867)
<220> FEATURE:
<221> NAME/KEY: REPEAT
<222> LOCATION: (868)..(880)
<220> FEATURE:
<221> NAME/KEY: REPEAT
<222> LOCATION: (881)..(903)
<220> FEATURE:
<221> NAME/KEY: REPEAT
<222> LOCATION: (904)..(917)
<220> FEATURE:
<221> NAME/KEY: REPEAT
<222> LOCATION: (918)..(931)
<220> FEATURE:
<221> NAME/KEY: REPEAT
<222> LOCATION: (932)..(945)
```

```
<220> FEATURE:
<221> NAME/KEY: REPEAT
<222> LOCATION: (946)..(968)
<220> FEATURE:
<221> NAME/KEY: REPEAT
<222> LOCATION: (969)..(981)
<220> FEATURE:
<221> NAME/KEY: REPEAT
<222> LOCATION: (982)..(998)
<220> FEATURE:
<221> NAME/KEY: REPEAT
<222> LOCATION: (999)..(1013)
<220> FEATURE:
<221> NAME/KEY: REPEAT
<222> LOCATION: (1014)..(1027)
<220> FEATURE:
<221> NAME/KEY: REPEAT
<222> LOCATION: (1028)..(1042)
<220> FEATURE:
<221> NAME/KEY: REPEAT
<222> LOCATION: (1043)..(1059)
<220> FEATURE:
<221> NAME/KEY: REPEAT
<222> LOCATION: (1060)..(1073)
<220> FEATURE:
<221> NAME/KEY: REPEAT
<222> LOCATION: (1074)..(1092)

<400> SEQUENCE: 5

Gln Gly Ala Gly Gly Asn Ala Ala Ala Ala Ala Ala Ala Ala Ala
1               5                   10                  15

Ala Ala Ala Gly Gln Gly Gly Gln Gly Gly Tyr Gly Gly Leu Gly Gln
                20                  25                  30

Gly Gly Tyr Gly Gln Gly Ala Gly Ser Ser Ala Ala Ala Ala Ala
            35                  40                  45

Ala Ala Ala Ala Ala Ala Ala Ala Gly Arg Gly Gln Gly Gly Tyr Gly
        50                  55                  60

Gln Gly Ser Gly Gly Asn Ala Ala Ala Ala Ala Ala Ala Ala Ala
65                  70                  75                  80

Ala Ala Ser Gly Gln Gly Gly Gln Gly Gly Gln Gly Gln Gly Gln
                85                  90                  95

Gly Gly Tyr Gly Gln Gly Ala Gly Ser Ser Ala Ala Ala Ala Ala
            100                 105                 110

Ala Ala Ala Ala Ala Ala Ala Ala Gly Gln Gly Gln Gly Arg Tyr Gly
        115                 120                 125

Gln Gly Ala Gly Gly Asn Ala Ala Ala Ala Ala Ala Ala Ala Ala
            130                 135                 140

Ala Ala Ala Gly Gln Gly Gly Gln Gly Gly Gln Gly Gly Leu Gly Gln
145                 150                 155                 160

Gly Gly Tyr Gly Gln Gly Ala Gly Ser Ser Ala Ala Ala Ala Ala
                165                 170                 175

Ser Ala Ala Ala Ala Ala Ala Gly Arg Gly Gln Gly Gly Tyr Gly Gln
            180                 185                 190

Gly Ala Gly Gly Asn Ala Ala Ala Ala Ala Ala Ala Ala Ala Ala
            195                 200                 205

Ala Ala Ala Gly Gln Gly Gly Gln Gly Gly Tyr Gly Gly Leu Gly Gln
        210                 215                 220

Gly Gly Tyr Gly Gln Gly Ala Gly Ser Ser Ala Ala Ala Ala Ala
225                 230                 235                 240

Ala Ala Ala Ala Ala Ala Ala Gly Gly Gln Gly Gln Gly Gln Gly
                245                 250                 255

Arg Tyr Gly Gln Gly Ala Gly Ser Ser Ala Ala Ala Ala Ala Ala
```

-continued

```
                260                 265                 270
Ala Ala Ala Ala Ala Ala Gly Gln Gly Gln Gly Gly Tyr Gly Gln
        275                 280                 285
Gly Ala Gly Gly Asn Ala Ala Ala Ala Ala Ala Ala Ala Ala Ala
        290                 295                 300
Ala Ala Gly Gln Gly Gln Gly Gly Gln Gly Gly Leu Gly Gln Gly
    305                 310                 315                 320
Gly Tyr Gly Gln Gly Ala Gly Ser Ser Ala Ala Ala Ala Ala Ala
                325                 330                 335
Ala Ala Ala Ala Ala Ala Gly Arg Gly Gln Gly Gly Tyr Gly Gln Gly
            340                 345                 350
Ala Gly Gly Asn Ala Ala Ala Ala Ala Ala Ala Ala Glu Ala Ala
            355                 360                 365
Ala Ala Gly Gln Gly Gly Gln Gly Gly Tyr Gly Gly Leu Gly Gln Gly
            370                 375                 380
Gly Tyr Gly Gln Gly Ala Gly Ser Ser Ala Ala Ala Ala Ala Ala
    385                 390                 395                 400
Ala Ala Ala Ala Ala Ala Gly Arg Gly Gln Gly Gly Tyr Gly Gln Gly
                405                 410                 415
Ala Gly Gly Asn Ala Ala Ala Ala Ala Ala Ala Ala Ala Ala Ala
            420                 425                 430
Ala Ala Gly Gln Gly Gly Gln Gly Gly Tyr Gly Gly Leu Gly Gln Gly
            435                 440                 445
Gly Tyr Gly Gln Gly Ala Gly Ser Ser Ala Ala Ala Ala Ala Ala
        450                 455                 460
Ala Ala Ala Ala Ala Ala Gly Gly Gln Gly Gly Gln Gly Gln Gly Arg
465                 470                 475                 480
Tyr Gly Gln Gly Ala Gly Ser Ser Ala Ala Ala Ala Ala Ala Ala
                485                 490                 495
Ala Ala Ala Ala Ala Ala Gly Arg Gly Gln Gly Gly Tyr Gly Gln Gly
                500                 505                 510
Ser Gly Gly Asn Ala Ala Ala Ala Ala Ala Ala Ala Ala Ala Ala
            515                 520                 525
Ser Gly Gln Gly Ser Gln Gly Gly Gln Gly Gly Gln Gly Gly Gly
        530                 535                 540
Tyr Gly Gln Gly Ala Gly Ser Ser Ala Ala Ala Ala Ala Ala Ala
545                 550                 555                 560
Ala Ala Ala Ala Ala Ser Gly Arg Gly Gln Gly Gly Tyr Gly Gln Gly
                565                 570                 575
Ala Gly Gly Asn Ala Ala Ala Ala Ala Ala Ala Ala Ala Ala Ala
            580                 585                 590
Ala Ala Gly Gln Gly Gly Gln Gly Gly Tyr Gly Gly Leu Gly Gln Gly
            595                 600                 605
Gly Tyr Gly Gln Gly Ala Gly Ser Ser Ala Ala Ala Ala Ala Ala
            610                 615                 620
Ala Ala Ala Ala Ala Gly Gly Gln Gly Gly Gln Gly Gln Gly Gly Tyr
    625                 630                 635                 640
Gly Gln Gly Ala Gly Ser Ser Ala Ala Ala Ala Ala Ala Ala Ala
                645                 650                 655
Ala Ala Ala Ala Ala Gly Arg Gly Gln Gly Gly Tyr Gly Gln Gly Ser
            660                 665                 670
Gly Gly Asn Ala Ala Ala Ala Ala Ala Ala Ala Ala Ala Ala Ser
        675                 680                 685
```

```
Gly Gln Gly Gly Gln Gly Gly Gln Gly Gly Gln Gly Gly Tyr
    690             695             700
Gly Gln Gly Ala Gly Ser Ser Ala Ala Ala Ala Ala Ala Ala Ala
705             710             715                 720
Ala Ala Ala Ala Ala Gly Gln Gly Gln Gly Gly Tyr Gly Gln Gly Ala
            725             730             735
Gly Gly Asn Ala Ala Ala Ala Ala Ala Ala Ala Ala Ala
        740             745             750
Gly Gln Gly Gly Gln Gly Gly Gln Gly Gly Leu Gly Gln Gly Gly Tyr
        755             760             765
Gly Gln Gly Ala Gly Ser Ser Ala Ala Ala Ala Ala Ala Ala Ala
        770             775             780
Ala Ala Ala Ala Ala Gly Arg Gly Gln Gly Gly Tyr Gly Gln Gly Val
785             790             795                 800
Gly Gly Asn Ala Ala Ala Ala Ala Ala Ala Ala Ala Ala
        805             810             815
Gly Gln Gly Gly Gln Gly Gly Gln Gly Gly Leu Gly Gln Gly Gly Tyr
        820             825             830
Gly Gln Gly Ala Gly Ser Ser Ala Ala Ala Ala Ala Ala Ala Ala
        835             840             845
Ala Ala Ala Ala Ala Gly Arg Gly Gln Gly Gly Tyr Gly Gln Gly Ser
850             855             860
Gly Gly Asn Ala Ala Ala Ala Ala Ala Ala Ala Ala Ala Ser
865             870             875             880
Gly Gln Gly Ser Gln Gly Gly Gln Gly Gly Gln Gly Gly Tyr
        885             890             895
Gly Gln Gly Ala Gly Ser Ser Ala Ala Ala Ala Ala Ala Ala Ala
        900             905             910
Ala Ala Ala Ala Ser Gly Arg Gly Gln Gly Gly Tyr Gly Gln Gly Ala
            915             920             925
Gly Gly Asn Ala Ala Ala Ala Ala Ala Ala Ala Ala Ala Ala
        930             935             940
Ala Gly Gln Gly Gly Gln Gly Gly Tyr Gly Gly Leu Gly Gln Gly Gly
945             950             955                 960
Tyr Gly Gln Gly Ala Gly Ser Ser Ala Ala Ala Ala Ala Ala Ala
            965             970             975
Ala Ala Ala Ala Gly Gly Gln Gly Gly Gln Gly Gln Gly Gly Tyr Gly
            980             985             990
Gln Gly Ser Gly Gly Ser Ala Ala Ala Ala Ala Ala Ala Ala Ala
        995             1000            1005
Ala Ala Ala Ala Ala Gly Arg Gly Gln Gly Gly Tyr Gly Gln Gly
        1010            1015            1020
Ser Gly Gly Asn Ala Ala Ala Ala Ala Ala Ala Ala Ala Ala
        1025            1030            1035
Ala Ala Ala Ala Gly Gln Gly Gly Gln Gly Gly Tyr Gly Arg Gln
        1040            1045            1050
Ser Gln Gly Ala Gly Ser Ala Ala Ala Ala Ala Ala Ala Ala
        1055            1060            1065
Ala Ala Ala Ala Ala Gly Ser Gly Gln Gly Gly Tyr Gly Gly Gln
        1070            1075            1080
Gly Gln Gly Gly Tyr Gly Gln Ser Ser Ala Ser Ala Ser Ala Ala
        1085            1090            1095
```

```
Ala Ser  Ala Ala Ser Thr Val  Ala Asn Ser Val Ser
    1100              1105              1110
```

<210> SEQ ID NO 6
<211> LENGTH: 23
<212> TYPE: PRT
<213> ORGANISM: Artificial Sequence
<220> FEATURE:
<223> OTHER INFORMATION: Consensus sequence derived from internal
      repeats of Euprosthenops australis MaSp1
<220> FEATURE:
<221> NAME/KEY: VARIANT
<222> LOCATION: (4)..(4)
<223> OTHER INFORMATION: Ser
<220> FEATURE:
<221> NAME/KEY: VARIANT
<222> LOCATION: (8)..(8)
<223> OTHER INFORMATION: Tyr
<220> FEATURE:
<221> NAME/KEY: VARIANT
<222> LOCATION: (11)..(11)
<223> OTHER INFORMATION: Gln

<400> SEQUENCE: 6

```
Gly Gln Gly Gly Gln Gly Gly Gln Gly Gly Leu Gly Gln Gly Gly Tyr
1               5                   10                  15

Gly Gln Gly Ala Gly Ser Ser
            20
```

<210> SEQ ID NO 7
<211> LENGTH: 17
<212> TYPE: PRT
<213> ORGANISM: Artificial Sequence
<220> FEATURE:
<223> OTHER INFORMATION: Consensus sequence derived from internal
      repeats of Euprosthenops australis MaSp1
<220> FEATURE:
<221> NAME/KEY: VARIANT
<222> LOCATION: (9)..(9)
<223> OTHER INFORMATION: Arg
<220> FEATURE:
<221> NAME/KEY: VARIANT
<222> LOCATION: (14)..(14)
<223> OTHER INFORMATION: Ser
<220> FEATURE:
<221> NAME/KEY: VARIANT
<222> LOCATION: (16)..(16)
<223> OTHER INFORMATION: Gly

<400> SEQUENCE: 7

```
Gly Gln Gly Gly Gln Gly Gln Gly Gly Tyr Gly Gln Gly Ala Gly Ser
1               5                   10                  15

Ser
```

<210> SEQ ID NO 8
<211> LENGTH: 14
<212> TYPE: PRT
<213> ORGANISM: Artificial Sequence
<220> FEATURE:
<223> OTHER INFORMATION: Consensus sequence derived from internal
      repeats of Euprosthenops australis MaSp1
<220> FEATURE:
<221> NAME/KEY: VARIANT
<222> LOCATION: (2)..(2)
<223> OTHER INFORMATION: Gln
<220> FEATURE:
<221> NAME/KEY: VARIANT
<222> LOCATION: (6)..(6)
<223> OTHER INFORMATION: Arg
<220> FEATURE:
<221> NAME/KEY: VARIANT
<222> LOCATION: (11)..(11)

```
<223> OTHER INFORMATION: Ser
<220> FEATURE:
<221> NAME/KEY: VARIANT
<222> LOCATION: (11)..(11)
<223> OTHER INFORMATION: Val

<400> SEQUENCE: 8

Gly Arg Gly Gln Gly Gly Tyr Gly Gln Gly Ala Gly Gly Asn
1               5                   10

<210> SEQ ID NO 9
<211> LENGTH: 10
<212> TYPE: PRT
<213> ORGANISM: Homo sapiens

<400> SEQUENCE: 9

Val Thr Gly Arg Gly Asp Ser Pro Ala Ser
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Modified from Homo sapiens
<220> FEATURE:
<221> NAME/KEY: DISULFID
<222> LOCATION: (1)..(10)

<400> SEQUENCE: 10

Cys Thr Gly Arg Gly Asp Ser Pro Ala Cys
1               5                   10

<210> SEQ ID NO 11
<211> LENGTH: 10
<212> TYPE: PRT
<213> ORGANISM: Artificial Sequence
<220> FEATURE:
<223> OTHER INFORMATION: modified from Homo sapiens

<400> SEQUENCE: 11

Ser Thr Gly Arg Gly Asp Ser Pro Ala Ser
1               5                   10

<210> SEQ ID NO 12
<211> LENGTH: 12
<212> TYPE: PRT
<213> ORGANISM: Artificial Sequence
<220> FEATURE:
<223> OTHER INFORMATION: linear RGD cell-binding motif

<400> SEQUENCE: 12

Gly Pro Asn Ser Arg Gly Asp Ala Gly Ala Ala Ser
1               5                   10

<210> SEQ ID NO 13
<211> LENGTH: 277
<212> TYPE: PRT
<213> ORGANISM: Artificial Sequence
<220> FEATURE:
<223> OTHER INFORMATION: Fusion protein
<220> FEATURE:
<221> NAME/KEY: DISULFID
<222> LOCATION: (5)..(14)

<400> SEQUENCE: 13

Gly Pro Asn Ser Cys Thr Gly Arg Gly Asp Ser Pro Ala Cys Gly Ser
1               5                   10                  15
```

-continued

```
Ala Ser Gly Gln Gly Gly Tyr Gly Gly Leu Gly Gln Gly Gly Tyr Gly
            20                  25                  30

Gln Gly Ala Gly Ser Ser Ala Ala Ala Ala Ala Ala Ala Ala Ala Ala
        35                  40                  45

Ala Ala Gly Gly Gln Gly Gln Gly Gln Gly Gly Tyr Gly Gln Gly
    50                  55                  60

Ser Gly Gly Ser Ala Ala Ala Ala Ala Ala Ala Ala Ala Ala Ala Ala
65                  70                  75                  80

Ala Ala Ala Gly Arg Gly Gln Gly Gly Tyr Gly Gln Gly Ser Gly Gly
                85                  90                  95

Asn Ala Ala Ala Ala Ala Ala Ala Ala Ala Ala Ala Ala Ala
                100                 105                 110

Gly Gln Gly Gly Gln Gly Gly Tyr Gly Arg Gln Ser Gln Gly Ala Gly
            115                 120                 125

Ser Ala Ala Ala Ala Ala Ala Ala Ala Ala Ala Ala Ala Ala Gly
        130                 135                 140

Ser Gly Gln Gly Gly Tyr Gly Gly Gln Gly Gly Tyr Gly Gln
145                 150                 155                 160

Ser Ser Ala Ser Ala Ser Ala Ala Ser Ala Ala Ser Thr Val Ala
                165                 170                 175

Asn Ser Val Ser Arg Leu Ser Ser Pro Ser Ala Val Ser Arg Val Ser
            180                 185                 190

Ser Ala Val Ser Ser Leu Val Ser Asn Gly Gln Val Asn Met Ala Ala
        195                 200                 205

Leu Pro Asn Ile Ile Ser Asn Ile Ser Ser Val Ser Ala Ser Ala
    210                 215                 220

Pro Gly Ala Ser Gly Cys Glu Val Ile Val Gln Ala Leu Leu Glu Val
225                 230                 235                 240

Ile Thr Ala Leu Val Gln Ile Val Ser Ser Ser Val Gly Tyr Ile
                245                 250                 255

Asn Pro Ser Ala Val Asn Gln Ile Thr Asn Val Val Ala Asn Ala Met
            260                 265                 270

Ala Gln Val Met Gly
            275

<210> SEQ ID NO 14
<211> LENGTH: 277
<212> TYPE: PRT
<213> ORGANISM: Artificial Sequence
<220> FEATURE:
<223> OTHER INFORMATION: Fusion protein

<400> SEQUENCE: 14

Gly Pro Asn Ser Ser Thr Gly Arg Gly Asp Ser Pro Ala Ser Gly Ser
1               5                   10                  15

Ala Ser Gly Gln Gly Gly Tyr Gly Gly Leu Gly Gln Gly Gly Tyr Gly
            20                  25                  30

Gln Gly Ala Gly Ser Ser Ala Ala Ala Ala Ala Ala Ala Ala Ala Ala
        35                  40                  45

Ala Ala Gly Gly Gln Gly Gln Gly Gln Gly Gly Tyr Gly Gln Gly
    50                  55                  60

Ser Gly Gly Ser Ala Ala Ala Ala Ala Ala Ala Ala Ala Ala Ala Ala
65                  70                  75                  80

Ala Ala Ala Gly Arg Gly Gln Gly Gly Tyr Gly Gln Gly Ser Gly Gly
                85                  90                  95
```

```
Asn Ala Ala Ala Ala Ala Ala Ala Ala Ala Ala Ala
            100                 105                 110

Gly Gln Gly Gly Gln Gly Gly Tyr Gly Arg Gln Ser Gln Gly Ala Gly
            115                 120                 125

Ser Ala Ala Ala Ala Ala Ala Ala Ala Ala Ala Gly
130                 135                 140

Ser Gly Gln Gly Gly Tyr Gly Gly Gln Gly Gln Gly Tyr Gly Gln
145                 150                 155                 160

Ser Ser Ala Ser Ala Ser Ala Ala Ser Ala Ala Ser Thr Val Ala
                165                 170                 175

Asn Ser Val Ser Arg Leu Ser Ser Pro Ser Ala Val Ser Arg Val Ser
            180                 185                 190

Ser Ala Val Ser Ser Leu Val Ser Asn Gly Gln Val Asn Met Ala Ala
            195                 200                 205

Leu Pro Asn Ile Ile Ser Asn Ile Ser Ser Val Ser Ala Ser Ala
210                 215                 220

Pro Gly Ala Ser Gly Cys Glu Val Ile Val Gln Ala Leu Leu Glu Val
225                 230                 235                 240

Ile Thr Ala Leu Val Gln Ile Val Ser Ser Ser Ser Val Gly Tyr Ile
                245                 250                 255

Asn Pro Ser Ala Val Asn Gln Ile Thr Asn Val Val Ala Asn Ala Met
            260                 265                 270

Ala Gln Val Met Gly
        275

<210> SEQ ID NO 15
<211> LENGTH: 277
<212> TYPE: PRT
<213> ORGANISM: Artificial Sequence
<220> FEATURE:
<223> OTHER INFORMATION: Fusion protein

<400> SEQUENCE: 15

Gly Pro Asn Ser Val Thr Gly Arg Gly Asp Ser Pro Ala Ser Gly Ser
1               5                   10                  15

Ala Ser Gly Gln Gly Gly Tyr Gly Gly Leu Gly Gln Gly Gly Tyr Gly
            20                  25                  30

Gln Gly Ala Gly Ser Ser Ala Ala Ala Ala Ala Ala Ala Ala Ala
            35                  40                  45

Ala Ala Gly Gly Gln Gly Gly Gln Gly Gln Gly Gly Tyr Gly Gln Gly
    50                  55                  60

Ser Gly Gly Ser Ala Ala Ala Ala Ala Ala Ala Ala Ala Ala Ala
65                  70                  75                  80

Ala Ala Ala Gly Arg Gly Gln Gly Gly Tyr Gly Gln Gly Ser Gly Gly
                85                  90                  95

Asn Ala Ala Ala Ala Ala Ala Ala Ala Ala Ala Ala Ala
            100                 105                 110

Gly Gln Gly Gly Gln Gly Gly Tyr Gly Arg Gln Ser Gln Gly Ala Gly
            115                 120                 125

Ser Ala Ala Ala Ala Ala Ala Ala Ala Ala Ala Gly
130                 135                 140

Ser Gly Gln Gly Gly Tyr Gly Gly Gln Gly Gln Gly Tyr Gly Gln
145                 150                 155                 160

Ser Ser Ala Ser Ala Ser Ala Ala Ser Ala Ala Ser Thr Val Ala
                165                 170                 175
```

```
Asn Ser Val Ser Arg Leu Ser Ser Pro Ser Ala Val Ser Arg Val Ser
            180                 185                 190

Ser Ala Val Ser Ser Leu Val Ser Asn Gly Gln Val Asn Met Ala Ala
        195                 200                 205

Leu Pro Asn Ile Ile Ser Asn Ile Ser Ser Val Ser Ala Ser Ala
    210                 215                 220

Pro Gly Ala Ser Gly Cys Glu Val Ile Val Gln Ala Leu Leu Glu Val
225                 230                 235                 240

Ile Thr Ala Leu Val Gln Ile Val Ser Ser Ser Val Gly Tyr Ile
                245                 250                 255

Asn Pro Ser Ala Val Asn Gln Ile Thr Asn Val Val Ala Asn Ala Met
            260                 265                 270

Ala Gln Val Met Gly
        275

<210> SEQ ID NO 16
<211> LENGTH: 271
<212> TYPE: PRT
<213> ORGANISM: Artificial Sequence
<220> FEATURE:
<223> OTHER INFORMATION: Fusion protein

<400> SEQUENCE: 16

Gly Pro Asn Ser Arg Gly Asp Ala Gly Ala Ser Gly Gln Gly Gly
1               5                   10                  15

Tyr Gly Gly Leu Gly Gln Gly Gly Tyr Gly Gln Gly Ala Gly Ser Ser
                20                  25                  30

Ala Ala Ala Ala Ala Ala Ala Ala Ala Ala Ala Gly Gly Gln Gly
            35                  40                  45

Gly Gln Gly Gln Gly Gly Tyr Gly Gln Gly Ser Gly Ser Ala Ala
        50                  55                  60

Ala Ala Ala Ala Ala Ala Ala Ala Ala Ala Ala Ala Gly Arg Gly
65                  70                  75                  80

Gln Gly Gly Tyr Gly Gln Gly Ser Gly Gly Asn Ala Ala Ala Ala
                85                  90                  95

Ala Ala Ala Ala Ala Ala Ala Ala Ala Gly Gln Gly Gly Gln Gly
            100                 105                 110

Gly Tyr Gly Arg Gln Ser Gln Gly Ala Gly Ser Ala Ala Ala Ala
                115                 120                 125

Ala Ala Ala Ala Ala Ala Ala Ala Gly Ser Gly Gln Gly Gly Tyr
        130                 135                 140

Gly Gly Gln Gly Gln Gly Gly Tyr Gly Gln Ser Ser Ala Ser Ala Ser
145                 150                 155                 160

Ala Ala Ala Ser Ala Ala Ser Thr Val Ala Asn Ser Val Ser Arg Leu
                165                 170                 175

Ser Ser Pro Ser Ala Val Ser Arg Val Ser Ser Ala Val Ser Ser Leu
            180                 185                 190

Val Ser Asn Gly Gln Val Asn Met Ala Ala Leu Pro Asn Ile Ile Ser
        195                 200                 205

Asn Ile Ser Ser Val Ser Ala Ser Ala Pro Gly Ala Ser Gly Cys
    210                 215                 220

Glu Val Ile Val Gln Ala Leu Leu Glu Val Ile Thr Ala Leu Val Gln
225                 230                 235                 240

Ile Val Ser Ser Ser Val Gly Tyr Ile Asn Pro Ser Ala Val Asn
                245                 250                 255
```

Gln Ile Thr Asn Val Val Ala Asn Ala Met Ala Gln Val Met Gly
        260                 265                 270

<210> SEQ ID NO 17
<211> LENGTH: 831
<212> TYPE: DNA
<213> ORGANISM: Artificial Sequence
<220> FEATURE:
<223> OTHER INFORMATION: Fusion protein

<400> SEQUENCE: 17

```
ggtccgaatt catgcacagg tcgtggtgat tctccggcgt gcggatccgc tagcggtcaa      60
ggaggatatg gtggactagg tcaaggaggg tatggacaag gtgcaggaag ttctgcagcc     120
gctgccgccg ccgcagcagc cgccgcagca ggtggacaag gtggacaagg tcaaggagga     180
tatggacaag gttcaggagg ttctgcagcc gccgccgccg ccgcagcagc agcagcagct     240
gcagcagctg gacgaggtca aggaggatat ggccaaggtt ctggaggtaa tgctgctgcc     300
gcagccgctg ccgccgccgc cgccgctgca gcagccggac agggaggtca aggtggatat     360
ggtagacaaa gccaaggtgc tggttccgct gctgctgctg ctgctgctgc tgccgctgct     420
gctgctgcag atctggaca aggtggatac ggtggacaag tcaaggagg ttatggtcag      480
agtagtgctt ctgcttcagc tgctgcgtca gctgctagta ctgtagctaa ttcggtgagt     540
cgcctctcat cgccttccgc agtatctcga gtttcttcag cagtttctag cttggtttca     600
aatggtcaag tgaatatggc agcgttacct aatatcattt ccaacatttc ttcttctgtc     660
agtgcatctg ctcctggtgc ttctggatgt gaggtcatag tgcaagctct actcgaagtc     720
atcactgctc ttgttcaaat cgttagttct tctagtgttg atatattaa ccatctgct       780
gtgaaccaaa ttactaatgt tgttgctaat gccatggctc aagtaatggg c              831
```

<210> SEQ ID NO 18
<211> LENGTH: 831
<212> TYPE: DNA
<213> ORGANISM: Artificial Sequence
<220> FEATURE:
<223> OTHER INFORMATION: Fusion protein

<400> SEQUENCE: 18

```
ggtccgaatt caagcacagg tcgtggtgat tctccggcga gcggatccgc tagcggtcaa      60
ggaggatatg gtggactagg tcaaggaggg tatggacaag gtgcaggaag ttctgcagcc     120
gctgccgccg ccgcagcagc cgccgcagca ggtggacaag gtggacaagg tcaaggagga     180
tatggacaag gttcaggagg ttctgcagcc gccgccgccg ccgcagcagc agcagcagct     240
gcagcagctg gacgaggtca aggaggatat ggccaaggtt ctggaggtaa tgctgctgcc     300
gcagccgctg ccgccgccgc cgccgctgca gcagccggac agggaggtca aggtggatat     360
ggtagacaaa gccaaggtgc tggttccgct gctgctgctg ctgctgctgc tgccgctgct     420
gctgctgcag atctggaca aggtggatac ggtggacaag tcaaggagg ttatggtcag      480
agtagtgctt ctgcttcagc tgctgcgtca gctgctagta ctgtagctaa ttcggtgagt     540
cgcctctcat cgccttccgc agtatctcga gtttcttcag cagtttctag cttggtttca     600
aatggtcaag tgaatatggc agcgttacct aatatcattt ccaacatttc ttcttctgtc     660
agtgcatctg ctcctggtgc ttctggatgt gaggtcatag tgcaagctct actcgaagtc     720
atcactgctc ttgttcaaat cgttagttct tctagtgttg atatattaa ccatctgct       780
gtgaaccaaa ttactaatgt tgttgctaat gccatggctc aagtaatggg c              831
```

<210> SEQ ID NO 19
<211> LENGTH: 831
<212> TYPE: DNA
<213> ORGANISM: Artificial Sequence
<220> FEATURE:
<223> OTHER INFORMATION: Fusion protein

<400> SEQUENCE: 19

```
ggtccgaatt cagttacagg tcgtggtgat tctccggcga gcggatccgc tagcggtcaa        60
ggaggatatg gtggactagg tcaaggaggg tatggacaag gtgcaggaag ttctgcagcc       120
gctgccgccg ccgcagcagc cgccgcagca ggtggacaag gtggacaagg tcaaggagga       180
tatggacaag gttcaggagg ttctgcagcc gccgccgccg ccgcagcagc agcagcagct       240
gcagcagctg gacgaggtca aggaggatat ggccaaggtt ctggaggtaa tgctgctgcc       300
gcagccgctg ccgccgccgc cgccgctgca gcagccggac agggaggtca aggtggatat       360
ggtagacaaa gccaaggtgc tggttccgct gctgctgctg ctgctgctgc tgccgctgct       420
gctgctgcag atctggaca aggtggatac ggtggacaag gtcaaggagg ttatggtcag        480
agtagtgctt ctgcttcagc tgctgcgtca gctgctagta ctgtagctaa ttcggtgagt       540
cgcctctcat cgccttccgc agtatctcga gtttcttcag cagtttctag cttggtttca       600
aatggtcaag tgaatatggc agcgttacct aatatcattt ccaacatttc ttcttctgtc       660
agtgcatctg ctcctggtgc ttctggatgt gaggtcatag tgcaagctct actcgaagtc       720
atcactgctc ttgttcaaat cgttagttct tctagtgttg atatattaa tccatctgct        780
gtgaaccaaa ttactaatgt tgttgctaat gccatggctc aagtaatggg c                 831
```

<210> SEQ ID NO 20
<211> LENGTH: 813
<212> TYPE: DNA
<213> ORGANISM: Artificial Sequence
<220> FEATURE:
<223> OTHER INFORMATION: Fusion protein

<400> SEQUENCE: 20

```
ggtccgaatt cacgcggcga tgcaggagcg gctagcggtc aaggaggata tggtggacta        60
ggtcaaggag ggtatggaca agtgcagga agttctgcag ccgctgccgc cgccgcagca       120
gccgccgcag caggtggaca aggtggacaa ggtcaaggag gatatggaca aggttcagga       180
ggttctgcag ccgccgccgc cgccgcagca gcagcagcag ctgcagcagc tggacgaggt       240
caaggaggat atggccaagg ttctggaggt aatgctgctg ccgcagccgc tgccgccgcc       300
gccgccgctg cagcagccgg acagggaggt caaggtggat atggtagaca aagccaaggt       360
gctggttccg ctgctgctgc tgctgctgct gctgccgctg ctgctgctgc aggatctgga       420
caaggtggat acggtggaca aggtcaagga ggttatggtc agagtagtgc ttctgcttca       480
gctgctgcgt cagctgctag tactgtagct aattcggtga gtcgcctctc atcgccttcc       540
gcagtatctc gagtttcttc agcagtttct agcttggttt caaatggtca agtgaatatg       600
gcagcgttac ctaatatcat ttccaacatt tcttcttctg tcagtgcatc tgctcctggt       660
gcttctggat gtgaggtcat agtgcaagct ctactcgaag tcatcactgc tcttgttcaa       720
atcgttagtt cttctagtgt tggatatatt aatccatctg ctgtgaacca aattactaat       780
gttgttgcta atgccatggc tcaagtaatg ggc                                     813
```

<210> SEQ ID NO 21

```
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: DISULFID
<222> LOCATION: (6)..(15)

<400> SEQUENCE: 21

Gly Gly Gly Gly Gly Cys Thr Gly Arg Gly Asp Ser Pro Ala Cys
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: Synthetic peptide

<400> SEQUENCE: 22

Gly Gly Gly Gly Gly Val Thr Gly Arg Gly Asp Ser Pro Ala Ser
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: Synthetic peptide

<400> SEQUENCE: 23

Gly Gly Gly Gly Gly Ser Thr Gly Arg Gly Asp Ser Pro Ala Ser
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: DISULFID
<222> LOCATION: (6)..(15)

<400> SEQUENCE: 24

Gly Gly Gly Gly Gly Cys Asp Trp Arg Gly Asp Asn Gln Phe Cys
1               5                   10                  15

<210> SEQ ID NO 25
<211> LENGTH: 18
<212> TYPE: PRT
<213> ORGANISM: Euprosthenops australis

<400> SEQUENCE: 25

Ala Ser Ala Ser Ala Ala Ala Ser Ala Ala Ser Thr Val Ala Asn Ser
1               5                   10                  15

Val Ser

<210> SEQ ID NO 26
<211> LENGTH: 8
<212> TYPE: PRT
<213> ORGANISM: Euprosthenops australis

<400> SEQUENCE: 26

Ala Ser Ala Ala Ser Ala Ala Ala
1               5
```

```
<210> SEQ ID NO 27
<211> LENGTH: 8
<212> TYPE: PRT
<213> ORGANISM: Euprosthenops australis

<400> SEQUENCE: 27

Gly Ser Ala Met Gly Gln Gly Ser
1               5

<210> SEQ ID NO 28
<211> LENGTH: 5
<212> TYPE: PRT
<213> ORGANISM: Euprosthenops australis

<400> SEQUENCE: 28

Ser Ala Ser Ala Gly
1               5

<210> SEQ ID NO 29
<211> LENGTH: 100
<212> TYPE: PRT
<213> ORGANISM: Euprosthenops sp

<400> SEQUENCE: 29

Ser Arg Leu Ser Ser Pro Glu Ala Ser Ser Arg Val Ser Ser Ala Val
1               5                   10                  15

Ser Asn Leu Val Ser Ser Gly Pro Thr Asn Ser Ala Ala Leu Ser Ser
                20                  25                  30

Thr Ile Ser Asn Val Val Ser Gln Ile Gly Ala Ser Asn Pro Gly Leu
            35                  40                  45

Ser Gly Cys Asp Val Leu Val Gln Ala Leu Leu Glu Val Val Ser Ala
        50                  55                  60

Leu Ile His Ile Leu Gly Ser Ser Ile Gly Gln Val Asn Tyr Gly
65                  70                  75                  80

Ser Ala Gly Gln Ala Thr Gln Leu Val Gly Gln Ser Val Tyr Gln Ala
                85                  90                  95

Leu Gly Glu Phe
            100

<210> SEQ ID NO 30
<211> LENGTH: 98
<212> TYPE: PRT
<213> ORGANISM: Euprosthenops australis

<400> SEQUENCE: 30

Ser Arg Leu Ser Ser Pro Ser Ala Val Ser Arg Val Ser Ser Ala Val
1               5                   10                  15

Ser Ser Leu Val Ser Asn Gly Gln Val Asn Met Ala Ala Leu Pro Asn
                20                  25                  30

Ile Ile Ser Asn Ile Ser Ser Ser Val Ser Ala Ser Ala Pro Gly Ala
            35                  40                  45

Ser Gly Cys Glu Val Ile Val Gln Ala Leu Leu Glu Val Ile Thr Ala
        50                  55                  60

Leu Val Gln Ile Val Ser Ser Ser Val Gly Tyr Ile Asn Pro Ser
65                  70                  75                  80

Ala Val Asn Gln Ile Thr Asn Val Val Ala Asn Ala Met Ala Gln Val
                85                  90                  95

Met Gly
```

<210> SEQ ID NO 31
<211> LENGTH: 99
<212> TYPE: PRT
<213> ORGANISM: Argiope trifasciata

<400> SEQUENCE: 31

Ser Arg Leu Ser Ser Pro Gly Ala Ala Ser Arg Val Ser Ser Ala Val
1               5                   10                  15

Thr Ser Leu Val Ser Ser Gly Gly Pro Thr Asn Ser Ala Ala Leu Ser
            20                  25                  30

Asn Thr Ile Ser Asn Val Val Ser Gln Ile Ser Ser Ser Asn Pro Gly
        35                  40                  45

Leu Ser Gly Cys Asp Val Leu Val Gln Ala Leu Leu Glu Ile Val Ser
    50                  55                  60

Ala Leu Val His Ile Leu Gly Ser Ala Asn Ile Gly Gln Val Asn Ser
65                  70                  75                  80

Ser Gly Val Gly Arg Ser Ala Ser Ile Val Gly Gln Ser Ile Asn Gln
                85                  90                  95

Ala Phe Ser

<210> SEQ ID NO 32
<211> LENGTH: 89
<212> TYPE: PRT
<213> ORGANISM: Cyrtophora moluccensis

<400> SEQUENCE: 32

Ser His Leu Ser Ser Pro Glu Ala Ser Ser Arg Val Ser Ser Ala Val
1               5                   10                  15

Ser Asn Leu Val Ser Ser Gly Ser Thr Asn Ser Ala Ala Leu Pro Asn
            20                  25                  30

Thr Ile Ser Asn Val Val Ser Gln Ile Ser Ser Ser Asn Pro Gly Leu
        35                  40                  45

Ser Gly Cys Asp Val Leu Val Gln Ala Leu Leu Glu Val Val Ser Ala
    50                  55                  60

Leu Ile His Ile Leu Gly Ser Ser Ile Gly Gln Val Asn Tyr Gly
65                  70                  75                  80

Ser Ala Gly Gln Ala Thr Gln Ile Val
                85

<210> SEQ ID NO 33
<211> LENGTH: 98
<212> TYPE: PRT
<213> ORGANISM: Latrodectus geometricus

<400> SEQUENCE: 33

Ser Ala Leu Ala Ala Pro Ala Thr Ser Ala Arg Ile Ser Ser His Ala
1               5                   10                  15

Ser Thr Leu Leu Ser Asn Gly Pro Thr Asn Pro Ala Ser Ile Ser Asn
            20                  25                  30

Val Ile Ser Asn Ala Val Ser Gln Ile Ser Ser Ser Asn Pro Gly Ala
        35                  40                  45

Ser Ser Cys Asp Val Leu Val Gln Ala Leu Leu Glu Leu Val Thr Ala
    50                  55                  60

Leu Leu Thr Ile Ile Gly Ser Ser Asn Val Gly Asn Val Asn Tyr Asp
65                  70                  75                  80

Ser Ser Gly Gln Tyr Ala Gln Val Val Gln Ser Val Gln Asn Ala

-continued

```
                85                  90                  95

Phe Val

<210> SEQ ID NO 34
<211> LENGTH: 98
<212> TYPE: PRT
<213> ORGANISM: Latrodectus hesperus

<400> SEQUENCE: 34

Ser Ala Leu Ser Ala Pro Ala Thr Ser Ala Arg Ile Ser Ser His Ala
1               5                   10                  15

Ser Ala Leu Leu Ser Ser Gly Pro Thr Asn Pro Ala Ser Ile Ser Asn
            20                  25                  30

Val Ile Ser Asn Ala Val Ser Gln Ile Ser Ser Ser Asn Pro Gly Ala
        35                  40                  45

Ser Ala Cys Asp Val Leu Val Gln Ala Leu Leu Glu Leu Val Thr Ala
    50                  55                  60

Leu Leu Thr Ile Ile Gly Ser Ser Asn Ile Gly Ser Val Asn Tyr Asp
65                  70                  75                  80

Ser Ser Gly Gln Tyr Ala Gln Val Val Thr Gln Ser Val Gln Asn Val
                85                  90                  95

Phe Gly

<210> SEQ ID NO 35
<211> LENGTH: 93
<212> TYPE: PRT
<213> ORGANISM: Macrothele holsti

<400> SEQUENCE: 35

Ser His Leu Ser Ser Pro Glu Ala Ser Ser Arg Val Ser Ser Ala Val
1               5                   10                  15

Ser Asn Leu Val Ser Gly Gly Ser Thr Asn Ser Ala Ala Leu Pro Asn
            20                  25                  30

Thr Ile Ser Asn Val Val Ser Gln Ile Ser Ser Ser Asn Pro Gly Leu
        35                  40                  45

Ser Gly Cys Asp Val Leu Val Gln Ala Leu Leu Glu Val Val Ser Ala
    50                  55                  60

Leu Ile His Ile Leu Gly Ser Ser Ile Gly Gln Val Asp Tyr Gly
65                  70                  75                  80

Ser Ala Gly Gln Ala Thr Gln Ile Val Gly Gln Ser Ala
                85                  90

<210> SEQ ID NO 36
<211> LENGTH: 98
<212> TYPE: PRT
<213> ORGANISM: Nephila clavipes

<400> SEQUENCE: 36

Ser Arg Leu Ser Ser Pro Gln Ala Ser Ser Arg Val Ser Ala Val
1               5                   10                  15

Ser Asn Leu Val Ala Ser Gly Pro Thr Asn Ser Ala Ala Leu Ser Ser
            20                  25                  30

Thr Ile Ser Asn Val Val Ser Gln Ile Gly Ala Ser Asn Pro Gly Leu
        35                  40                  45

Ser Gly Cys Asp Val Leu Ile Gln Ala Leu Leu Glu Val Val Ser Ala
    50                  55                  60

Leu Ile Gln Ile Leu Gly Ser Ser Ser Ile Gly Gln Val Asn Tyr Gly
```

```
                65                  70                  75                  80
Ser Ala Gly Gln Ala Thr Gln Ile Val Gly Gln Ser Val Tyr Gln Ala
                    85                  90                  95

Leu Gly

<210> SEQ ID NO 37
<211> LENGTH: 89
<212> TYPE: PRT
<213> ORGANISM: Nephila pilipes

<400> SEQUENCE: 37

Ser Arg Leu Ser Ser Pro Glu Ala Ser Ser Arg Val Ser Ser Ala Val
1               5                   10                  15

Ser Asn Leu Val Ser Ser Gly Pro Thr Asn Ser Ala Ala Leu Ser Asn
                20                  25                  30

Thr Ile Ser Asn Val Val Ser Gln Ile Ser Ser Asn Pro Gly Leu
            35                  40                  45

Ser Gly Cys Asp Val Leu Val Gln Ala Leu Leu Glu Val Val Ser Ala
        50                  55                  60

Leu Ile His Ile Leu Gly Ser Ser Ile Gly Gln Val Asn Tyr Gly
65                  70                  75                  80

Ser Ala Gly Gln Ala Thr Gln Ile Val
                85

<210> SEQ ID NO 38
<211> LENGTH: 87
<212> TYPE: PRT
<213> ORGANISM: Nephila madagascariensis

<400> SEQUENCE: 38

Ser Arg Leu Ser Ser Pro Gln Ala Ser Ser Arg Val Ser Ser Ala Val
1               5                   10                  15

Ser Asn Leu Val Ala Ser Gly Pro Thr Asn Ser Ala Ala Leu Ser Ser
                20                  25                  30

Thr Ile Ser Asn Ala Val Ser Gln Ile Gly Ala Ser Asn Pro Gly Leu
            35                  40                  45

Ser Gly Cys Asp Val Leu Ile Gln Ala Leu Leu Glu Val Val Ser Ala
        50                  55                  60

Leu Ile His Ile Leu Gly Ser Ser Ile Gly Gln Val Asn Tyr Gly
65                  70                  75                  80

Ser Ala Gly Gln Ala Thr Gln
                85

<210> SEQ ID NO 39
<211> LENGTH: 87
<212> TYPE: PRT
<213> ORGANISM: Nephila senegalensis

<400> SEQUENCE: 39

Ser Arg Leu Ser Ser Pro Glu Ala Ser Ser Arg Val Ser Ser Ala Val
1               5                   10                  15

Ser Asn Leu Val Ser Ser Gly Pro Thr Asn Ser Ala Ala Leu Ser Ser
                20                  25                  30

Thr Ile Ser Asn Val Val Ser Gln Ile Gly Ala Ser Asn Pro Gly Leu
            35                  40                  45

Ser Gly Cys Asp Val Leu Ile Gln Ala Leu Leu Glu Val Val Ser Ala
        50                  55                  60
```

```
Leu Val His Ile Leu Gly Ser Ser Ile Gly Gln Val Asn Tyr Gly
 65                  70                  75                  80

Ser Ala Gly Gln Ala Thr Gln
                 85
```

<210> SEQ ID NO 40
<211> LENGTH: 89
<212> TYPE: PRT
<213> ORGANISM: Octonoba varians

<400> SEQUENCE: 40

```
Ser Arg Leu Ser Ser Pro Glu Ala Ser Ser Arg Val Ser Ser Ala Val
  1               5                  10                  15

Ser Asn Leu Val Ser Ser Gly Pro Thr Asn Ser Ala Ala Leu Ser Asn
                 20                  25                  30

Thr Ile Ser Asn Val Val Ser Gln Ile Ser Ser Ser Asn Pro Gly Leu
             35                  40                  45

Ser Gly Cys Asp Val Leu Val Gln Ala Leu Leu Glu Val Val Ser Ala
 50                  55                  60

Pro Ile His Ile Leu Gly Ser Ser Ile Gly Gln Val Asn Tyr Gly
 65                  70                  75                  80

Ser Ala Gly Gln Ala Thr Gln Ile Val
                 85
```

<210> SEQ ID NO 41
<211> LENGTH: 89
<212> TYPE: PRT
<213> ORGANISM: Psechrus sinensis

<400> SEQUENCE: 41

```
Ser Arg Leu Ser Ser Pro Glu Ala Ser Ser Arg Val Ser Ser Ala Val
  1               5                  10                  15

Ser Asn Leu Val Ser Ser Gly Pro Thr Asn Ser Ala Ala Leu Pro Asn
                 20                  25                  30

Thr Ile Ser Asn Val Val Ser Gln Ile Ser Ser Ser Asn Pro Gly Leu
             35                  40                  45

Ser Gly Cys Asp Val Leu Val Gln Ala Leu Leu Glu Val Val Ser Ala
 50                  55                  60

Leu Ile His Ile Leu Gly Ser Ser Ile Gly Gln Val Asn Tyr Gly
 65                  70                  75                  80

Ser Ala Gly Gln Ala Thr Gln Ile Val
                 85
```

<210> SEQ ID NO 42
<211> LENGTH: 88
<212> TYPE: PRT
<213> ORGANISM: Tetragnatha kauaiensis

<400> SEQUENCE: 42

```
Ser Leu Leu Ser Ser Pro Ala Ser Asn Ala Arg Ile Ser Ser Ala Val
  1               5                  10                  15

Ser Ala Leu Ala Ser Gly Ala Ala Ser Gly Pro Gly Tyr Leu Ser Ser
                 20                  25                  30

Val Ile Ser Asn Val Val Ser Gln Val Ser Ser Asn Ser Gly Gly Leu
             35                  40                  45

Val Gly Cys Asp Thr Leu Val Gln Ala Leu Leu Glu Ala Ala Ala Ala
 50                  55                  60

Leu Val His Val Leu Ala Ser Ser Ser Gly Gly Gln Val Asn Leu Asn
```

```
                65                  70                  75                  80
Thr Ala Gly Tyr Thr Ser Gln Leu
                85

<210> SEQ ID NO 43
<211> LENGTH: 88
<212> TYPE: PRT
<213> ORGANISM: Tetragnatha versicolor

<400> SEQUENCE: 43

Ser Arg Leu Ser Ser Pro Ala Ser Asn Ala Arg Ile Ser Ser Ala Val
1               5                   10                  15

Ser Ala Leu Ala Ser Gly Gly Ala Ser Ser Pro Gly Tyr Leu Ser Ser
                20                  25                  30

Ile Ile Ser Asn Val Val Ser Gln Val Ser Ser Asn Asn Asp Gly Leu
                35                  40                  45

Ser Gly Cys Asp Thr Val Val Gln Ala Leu Leu Glu Val Ala Ala Ala
                50                  55                  60

Leu Val His Val Leu Ala Ser Ser Asn Ile Gly Gln Val Asn Leu Asn
65              70                  75                  80

Thr Ala Gly Tyr Thr Ser Gln Leu
                85

<210> SEQ ID NO 44
<211> LENGTH: 89
<212> TYPE: PRT
<213> ORGANISM: Araneus bicentenarius

<400> SEQUENCE: 44

Ser Arg Leu Ser Ser Ala Ala Ser Ser Arg Val Ser Ser Ala Val
1               5                   10                  15

Ser Ser Leu Val Ser Ser Gly Pro Thr Thr Pro Ala Ala Leu Ser Asn
                20                  25                  30

Thr Ile Ser Ser Ala Val Ser Gln Ile Ser Ala Ser Asn Pro Gly Leu
                35                  40                  45

Ser Gly Cys Asp Val Leu Val Gln Ala Leu Leu Glu Val Val Ser Ala
                50                  55                  60

Leu Val His Ile Leu Gly Ser Ser Val Gly Gln Ile Asn Tyr Gly
65              70                  75                  80

Ala Ser Ala Gln Tyr Ala Gln Met Val
                85

<210> SEQ ID NO 45
<211> LENGTH: 97
<212> TYPE: PRT
<213> ORGANISM: Argiope amoena

<400> SEQUENCE: 45

Arg Leu Ser Ser Pro Gln Ala Ser Ser Arg Val Ser Ser Ala Val Ser
1               5                   10                  15

Thr Leu Val Ser Ser Gly Pro Thr Asn Pro Ala Ser Leu Ser Asn Ala
                20                  25                  30

Ile Gly Ser Val Val Ser Gln Val Ser Ala Ser Asn Pro Gly Leu Pro
                35                  40                  45

Ser Cys Asp Val Leu Val Gln Ala Leu Leu Glu Ile Val Ser Ala Leu
                50                  55                  60

Val His Ile Leu Gly Ser Ser Ser Ile Gly Gln Ile Asn Tyr Ser Ala
65              70                  75                  80
```

```
Ser Ser Gln Tyr Ala Arg Leu Val Gly Gln Ser Ile Ala Gln Ala Leu
                85                  90                  95

Gly

<210> SEQ ID NO 46
<211> LENGTH: 82
<212> TYPE: PRT
<213> ORGANISM: Argiope aurantia

<400> SEQUENCE: 46

Ser Arg Leu Ser Ser Pro Gln Ala Ser Ser Arg Val Ser Ser Ala Val
1               5                   10                  15

Ser Thr Leu Val Ser Ser Gly Pro Thr Asn Pro Ala Ala Leu Ser Asn
                20                  25                  30

Ala Ile Ser Ser Val Val Ser Gln Val Ser Ala Ser Asn Pro Gly Leu
            35                  40                  45

Ser Gly Cys Asp Val Leu Val Gln Ala Leu Leu Glu Leu Val Ser Ala
        50                  55                  60

Leu Val His Ile Leu Gly Ser Ser Ile Gly Gln Ile Asn Tyr Ala
65                  70                  75                  80

Ala Ser

<210> SEQ ID NO 47
<211> LENGTH: 98
<212> TYPE: PRT
<213> ORGANISM: Argiope trifasciata

<400> SEQUENCE: 47

Ser Arg Leu Ser Ser Pro Gln Ala Ser Ser Arg Val Ser Ser Ala Val
1               5                   10                  15

Ser Thr Leu Val Ser Ser Gly Pro Thr Asn Pro Ala Ser Leu Ser Asn
                20                  25                  30

Ala Ile Ser Ser Val Val Ser Gln Val Ser Ser Asn Pro Gly Leu
            35                  40                  45

Ser Gly Cys Asp Val Leu Val Gln Ala Leu Leu Glu Ile Val Ser Ala
        50                  55                  60

Leu Val His Ile Leu Gly Ser Ser Ile Gly Gln Ile Asn Tyr Ala
65                  70                  75                  80

Ala Ser Ser Gln Tyr Ala Gln Leu Val Gly Gln Ser Leu Thr Gln Ala
                85                  90                  95

Leu Gly

<210> SEQ ID NO 48
<211> LENGTH: 89
<212> TYPE: PRT
<213> ORGANISM: Gasteracantha mammosa

<400> SEQUENCE: 48

Ser Arg Leu Ser Ser Pro Gln Ala Gly Ala Arg Val Ser Ser Ala Val
1               5                   10                  15

Ser Ala Leu Val Ala Ser Gly Pro Thr Ser Pro Ala Ala Val Ser Ser
                20                  25                  30

Ala Ile Ser Asn Val Ala Ser Gln Ile Ser Ala Ser Asn Pro Gly Leu
            35                  40                  45

Ser Gly Cys Asp Val Leu Val Gln Ala Leu Leu Glu Ile Val Ser Ala
        50                  55                  60
```

```
Leu Val Ser Ile Leu Ser Ala Ser Ile Gly Gln Ile Asn Tyr Gly
 65                  70                  75                  80

Ala Ser Gly Gln Tyr Ala Ala Met Ile
                 85
```

<210> SEQ ID NO 49
<211> LENGTH: 90
<212> TYPE: PRT
<213> ORGANISM: Latrodectus geometricus

<400> SEQUENCE: 49

```
Ser Ala Leu Ser Ser Pro Thr Thr His Ala Arg Ile Ser Ser His Ala
 1               5                  10                  15

Ser Thr Leu Leu Ser Ser Gly Pro Thr Asn Ser Ala Ala Ile Ser Asn
                20                  25                  30

Val Ile Ser Asn Ala Val Ser Gln Val Ser Ala Ser Asn Pro Gly Ser
            35                  40                  45

Ser Ser Cys Asp Val Leu Val Gln Ala Leu Leu Glu Leu Ile Thr Ala
    50                  55                  60

Leu Ile Ser Ile Val Asp Ser Ser Asn Ile Gly Gln Val Asn Tyr Gly
 65                  70                  75                  80

Ser Ser Gly Gln Tyr Ala Gln Met Val Gly
                 85                  90
```

<210> SEQ ID NO 50
<211> LENGTH: 98
<212> TYPE: PRT
<213> ORGANISM: Latrodectus hesperus

<400> SEQUENCE: 50

```
Ser Ala Leu Ser Ser Pro Thr Thr His Ala Arg Ile Ser Ser His Ala
 1               5                  10                  15

Ser Thr Leu Leu Ser Ser Gly Pro Thr Asn Ala Ala Ala Leu Ser Asn
                20                  25                  30

Val Ile Ser Asn Ala Val Ser Gln Val Ser Ala Ser Asn Pro Gly Ser
            35                  40                  45

Ser Ser Cys Asp Val Leu Val Gln Ala Leu Leu Glu Ile Ile Thr Ala
    50                  55                  60

Leu Ile Ser Ile Leu Asp Ser Ser Ser Val Gly Gln Val Asn Tyr Gly
 65                  70                  75                  80

Ser Ser Gly Gln Tyr Ala Gln Ile Val Gly Gln Ser Met Gln Gln Ala
                 85                  90                  95

Met Gly
```

<210> SEQ ID NO 51
<211> LENGTH: 97
<212> TYPE: PRT
<213> ORGANISM: Nephila clavipes

<400> SEQUENCE: 51

```
Ser Arg Leu Ala Ser Pro Asp Ser Gly Ala Arg Val Ala Ser Ala Val
 1               5                  10                  15

Ser Asn Leu Val Ser Ser Gly Pro Thr Ser Ser Ala Ala Leu Ser Ser
                20                  25                  30

Val Ile Ser Asn Ala Val Ser Gln Ile Gly Ala Ser Asn Pro Gly Leu
            35                  40                  45

Ser Gly Cys Asp Val Leu Ile Gln Ala Leu Leu Glu Ile Val Ser Ala
    50                  55                  60
```

```
Cys Val Thr Ile Leu Ser Ser Ser Ile Gly Gln Val Asn Tyr Gly
 65                  70                  75                  80

Ala Ala Ser Gln Phe Ala Gln Val Val Gly Gln Ser Val Leu Ser Ala
                 85                  90                  95

Phe

<210> SEQ ID NO 52
<211> LENGTH: 82
<212> TYPE: PRT
<213> ORGANISM: Nephila madagascariensis

<400> SEQUENCE: 52

Ser Arg Leu Ala Ser Pro Asp Ser Gly Ala Arg Val Ala Ser Ala Val
  1               5                  10                  15

Ser Asn Leu Val Ser Ser Gly Pro Thr Ser Ser Ala Ala Leu Ser Ser
                 20                  25                  30

Val Ile Ser Asn Ala Val Ser Gln Ile Gly Ala Ser Asn Pro Gly Leu
             35                  40                  45

Ser Gly Cys Asp Val Leu Ile Gln Ala Leu Leu Glu Ile Val Ser Ala
 50                  55                  60

Cys Val Thr Ile Leu Ser Ser Ser Ile Gly Gln Val Asn Tyr Gly
 65                  70                  75                  80

Ala Ala

<210> SEQ ID NO 53
<211> LENGTH: 82
<212> TYPE: PRT
<213> ORGANISM: Nephila senegalensis
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (56)..(56)
<223> OTHER INFORMATION: Xaa can be any naturally occurring amino acid

<400> SEQUENCE: 53

Ser Arg Leu Ala Ser Pro Asp Ser Gly Ala Arg Val Ala Ser Ala Val
  1               5                  10                  15

Ser Asn Leu Val Ser Ser Gly Pro Thr Ser Ser Ala Ala Leu Ser Ser
                 20                  25                  30

Val Ile Xaa Asn Ala Val Ser Gln Ile Gly Ala Ser Asn Pro Gly Leu
             35                  40                  45

Ser Gly Cys Asp Val Leu Ile Xaa Ala Leu Leu Glu Ile Val Ser Ala
 50                  55                  60

Cys Val Thr Ile Leu Ser Ser Ser Ile Gly Gln Val Asn Tyr Gly
 65                  70                  75                  80

Ala Ala

<210> SEQ ID NO 54
<211> LENGTH: 71
<212> TYPE: PRT
<213> ORGANISM: Dolomedes tenebrosus

<400> SEQUENCE: 54

Ser Arg Leu Ser Ser Pro Glu Ala Ala Ser Arg Val Ser Ser Ala Val
  1               5                  10                  15

Ser Ser Leu Val Ser Asn Gly Gln Val Asn Val Asp Ala Leu Pro Ser
```

```
            20                  25                  30

Ile Ile Ser Asn Leu Ser Ser Ile Ser Ala Ser Ala Thr Thr Ala
        35                  40                  45

Ser Asp Cys Glu Val Leu Val Gln Val Leu Glu Val Val Ser Ala
    50                  55                  60

Leu Val Gln Ile Val Cys Ser
65                  70

<210> SEQ ID NO 55
<211> LENGTH: 97
<212> TYPE: PRT
<213> ORGANISM: Dolomedes tenebrosus

<400> SEQUENCE: 55

Ser Arg Leu Ser Ser Pro Gln Ala Ala Ser Arg Val Ser Ser Ala Val
1               5                   10                  15

Ser Ser Leu Val Ser Asn Gly Gln Val Asn Val Ala Ala Leu Pro Ser
            20                  25                  30

Ile Ile Ser Ser Leu Ser Ser Ser Ile Ser Ala Ser Ser Thr Ala Ala
        35                  40                  45

Ser Asp Cys Glu Val Leu Val Gln Val Leu Leu Glu Ile Val Ser Ala
    50                  55                  60

Leu Val Gln Ile Val Ser Ser Ala Asn Val Gly Tyr Ile Asn Pro Glu
65                  70                  75                  80

Ala Ser Gly Ser Leu Asn Ala Val Gly Ser Ala Leu Ala Ala Ala Met
                85                  90                  95

Gly

<210> SEQ ID NO 56
<211> LENGTH: 93
<212> TYPE: PRT
<213> ORGANISM: Araneus diadematus

<400> SEQUENCE: 56

Asn Arg Leu Ser Ser Ala Gly Ala Ala Ser Arg Val Ser Ser Asn Val
1               5                   10                  15

Ala Ala Ile Ala Ser Ala Gly Ala Ala Leu Pro Asn Val Ile Ser
            20                  25                  30

Asn Ile Tyr Ser Gly Val Leu Ser Ser Gly Val Ser Ser Ser Glu Ala
        35                  40                  45

Leu Ile Gln Ala Leu Leu Glu Val Ile Ser Ala Leu Ile His Val Leu
    50                  55                  60

Gly Ser Ala Ser Ile Gly Asn Val Ser Ser Val Gly Val Asn Ser Ala
65                  70                  75                  80

Leu Asn Ala Val Gln Asn Ala Val Gly Ala Tyr Ala Gly
                85                  90

<210> SEQ ID NO 57
<211> LENGTH: 98
<212> TYPE: PRT
<213> ORGANISM: Araneus diadematus

<400> SEQUENCE: 57

Ser Arg Leu Ser Ser Pro Ser Ala Ala Ala Arg Val Ser Ser Ala Val
1               5                   10                  15

Ser Leu Val Ser Asn Gly Gly Pro Thr Ser Pro Ala Ala Leu Ser Ser
            20                  25                  30
```

```
Ser Ile Ser Asn Val Val Ser Gln Ile Ser Ala Ser Asn Pro Gly Leu
         35                  40                  45

Ser Gly Cys Asp Ile Leu Val Gln Ala Leu Leu Glu Ile Ile Ser Ala
 50                  55                  60

Leu Val His Ile Leu Gly Ser Ala Asn Ile Gly Pro Val Asn Ser Ser
 65                  70                  75                  80

Ser Ala Gly Gln Ser Ala Ser Ile Val Gly Gln Ser Val Tyr Arg Ala
                 85                  90                  95

Leu Ser

<210> SEQ ID NO 58
<211> LENGTH: 98
<212> TYPE: PRT
<213> ORGANISM: Araneus diadematus

<400> SEQUENCE: 58

Ser Arg Leu Ser Ser Pro Ala Ala Ser Ser Arg Val Ser Ser Ala Val
 1               5                  10                  15

Ser Ser Leu Val Ser Ser Gly Pro Thr Lys His Ala Ala Leu Ser Asn
             20                  25                  30

Thr Ile Ser Ser Val Val Ser Gln Val Ser Ala Ser Asn Pro Gly Leu
         35                  40                  45

Ser Gly Cys Asp Val Leu Val Gln Ala Leu Leu Glu Val Val Ser Ala
 50                  55                  60

Leu Val Ser Ile Leu Gly Ser Ser Ser Ile Gly Gln Ile Asn Tyr Gly
 65                  70                  75                  80

Ala Ser Ala Gln Tyr Thr Gln Met Val Gly Gln Ser Val Ala Gln Ala
                 85                  90                  95

Leu Ala

<210> SEQ ID NO 59
<211> LENGTH: 94
<212> TYPE: PRT
<213> ORGANISM: Araneus diadematus

<400> SEQUENCE: 59

Ser Val Tyr Leu Arg Leu Gln Pro Arg Leu Glu Val Ser Ser Ala Val
 1               5                  10                  15

Ser Ser Leu Val Ser Ser Gly Pro Thr Asn Gly Ala Ala Val Ser Gly
             20                  25                  30

Ala Leu Asn Ser Leu Val Ser Gln Ile Ser Ala Ser Asn Pro Gly Leu
         35                  40                  45

Ser Gly Cys Asp Ala Leu Val Gln Ala Leu Leu Glu Leu Val Ser Ala
 50                  55                  60

Leu Val Ala Ile Leu Ser Ser Ala Ser Ile Gly Gln Val Asn Val Ser
 65                  70                  75                  80

Ser Val Ser Gln Ser Thr Gln Met Ile Ser Gln Ala Leu Ser
                 85                  90

<210> SEQ ID NO 60
<211> LENGTH: 10
<212> TYPE: PRT
<213> ORGANISM: Homo sapiens

<400> SEQUENCE: 60

Ser Thr Gly Arg Gly Asp Ser Pro Ala Val
 1               5                  10
```